(12) United States Patent
Mitelberg et al.

(10) Patent No.: US 8,128,592 B2
(45) Date of Patent: Mar. 6, 2012

(54) METHODS AND SYSTEMS FOR PERFORMING SUBMUCOSAL MEDICAL PROCEDURES

(75) Inventors: Vladimir Mitelberg, Austin, TX (US); Donald K. Jones, Dripping Springs, TX (US); David Y. Yuan, Austin, TX (US); Brett E. Naglreiter, Austin, TX (US); J. Landon Gilkey, Austin, TX (US); Christopher J. Gostout, Rochester, MN (US); Pankaj J. Pasricha, Houston, TX (US)

(73) Assignees: Apollo Endosurgery, Inc., Austin, TX (US); Mayo Foundation for Medical Education and Research, Rochester, MN (US); The Board of Regents of the University of Texas System, Austin, TX (US)

( * ) Notice: Subject to any disclaimer, the term of this patent is extended or adjusted under 35 U.S.C. 154(b) by 757 days.

(21) Appl. No.: 11/775,996

(22) Filed: Jul. 11, 2007

(65) Prior Publication Data
US 2009/0018602 A1    Jan. 15, 2009

(51) Int. Cl.
*A61M 31/00* (2006.01)
(52) U.S. Cl. ........ 604/93.01; 607/40; 606/192; 604/506
(58) Field of Classification Search .................... 607/40; 604/506, 93.01; 606/192
See application file for complete search history.

(56) References Cited

U.S. PATENT DOCUMENTS

| | | |
|---|---|---|
| 3,039,468 A | 6/1962 | Price |
| 3,910,279 A | 10/1975 | Okada et al. |
| 3,980,861 A | 9/1976 | Fukunaga |
| 4,222,380 A | 9/1980 | Terayama |
| 4,271,839 A | 6/1981 | Fogarty et al. |
| 4,418,692 A | 12/1983 | Guay |
| 4,445,892 A | 5/1984 | Hussein et al. |
| 4,630,609 A * | 12/1986 | Chin .............................. 606/194 |
| 4,655,219 A | 4/1987 | Petruzzi |
| 4,779,611 A | 10/1988 | Grotters et al. |
| 4,819,633 A | 4/1989 | Bauer et al. |
| 4,887,598 A | 12/1989 | Berke |
| 4,907,591 A | 3/1990 | Vasconcellos et al. |
| 5,009,659 A | 4/1991 | Hamlin et al. |
| 5,014,708 A | 5/1991 | Hayashi et al. |
| 5,078,716 A | 1/1992 | Doll |
| 5,080,660 A | 1/1992 | Buelna |
| 5,135,484 A | 8/1992 | Wright |
| 5,150,717 A | 9/1992 | Rosen et al. |
| 5,158,543 A | 10/1992 | Lazarus |
| 5,159,925 A | 11/1992 | Neuwirth et al. |
| 5,195,507 A | 3/1993 | Bilweis |
| 5,196,024 A | 3/1993 | Barath |

(Continued)

FOREIGN PATENT DOCUMENTS
WO    WO02/089655    11/2002
(Continued)

*Primary Examiner* — Max Hindenburg
*Assistant Examiner* — Renee Danega
(74) *Attorney, Agent, or Firm* — Gordon & Jacobson, PC

(57) ABSTRACT

Instruments, systems and methods are provided for performing submucosal medical procedures in a desired area of the digestive tract using endoscopy. Instruments include a safe access needle injection instrument, a submucosal tunneling instrument, a submucosal dissection instrument, a mucosal resection device. Systems include a combination of one or more of such instruments with or without injectable agents. Embodiments of various methods for performing the procedures are also provided.

11 Claims, 47 Drawing Sheets

U.S. PATENT DOCUMENTS

| | | | |
|---|---|---|---|
| 5,226,908 A | 7/1993 | Yoon | |
| 5,290,284 A | 3/1994 | Adair | |
| 5,300,023 A * | 4/1994 | Lowery et al. | 604/515 |
| 5,308,327 A | 5/1994 | Heaven et al. | |
| 5,318,543 A | 6/1994 | Ross et al. | |
| 5,318,564 A | 6/1994 | Eggers | |
| 5,339,799 A | 8/1994 | Kami et al. | |
| 5,370,134 A | 12/1994 | Chin et al. | |
| 5,372,601 A | 12/1994 | Lary | |
| 5,383,889 A * | 1/1995 | Warner et al. | 606/192 |
| 5,395,312 A | 3/1995 | Desai | |
| 5,417,697 A | 5/1995 | Wilk et al. | |
| 5,431,173 A | 7/1995 | Chin et al. | |
| 5,458,583 A | 10/1995 | McNeely et al. | |
| 5,507,744 A | 4/1996 | Tay et al. | |
| 5,507,765 A | 4/1996 | Mott | |
| 5,507,795 A | 4/1996 | Chiang et al. | |
| 5,527,273 A | 6/1996 | Manna et al. | |
| 5,531,699 A | 7/1996 | Tomba et al. | |
| 5,556,405 A | 9/1996 | Lary | |
| 5,570,700 A | 11/1996 | Vogeler | |
| 5,571,130 A | 11/1996 | Simpson et al. | |
| 5,582,609 A | 12/1996 | Swanson et al. | |
| 5,588,951 A | 12/1996 | Zhu et al. | |
| 5,591,183 A * | 1/1997 | Chin | 606/159 |
| 5,599,294 A | 2/1997 | Edwards et al. | |
| 5,599,300 A | 2/1997 | Weaver et al. | |
| 5,628,753 A | 5/1997 | Cracauer et al. | |
| 5,632,746 A | 5/1997 | Midleman et al. | |
| 5,643,305 A | 7/1997 | Al-Tameem | |
| 5,651,788 A | 7/1997 | Fleischer et al. | |
| 5,697,944 A | 12/1997 | Lary | |
| 5,702,438 A | 12/1997 | Avitall | |
| 5,709,224 A | 1/1998 | Behl et al. | |
| 5,713,364 A | 2/1998 | DeBaryshe et al. | |
| 5,718,703 A | 2/1998 | Chin | |
| 5,738,683 A | 4/1998 | Osypka | |
| 5,782,747 A | 7/1998 | Zimmon | |
| 5,782,800 A | 7/1998 | Yoon | |
| 5,800,449 A | 9/1998 | Wales | |
| 5,823,947 A | 10/1998 | Yoon et al. | |
| 5,827,268 A | 10/1998 | Laufer | |
| 5,836,947 A | 11/1998 | Fleischman et al. | |
| 5,868,767 A | 2/1999 | Farley et al. | |
| 5,871,475 A | 2/1999 | Frassica | |
| 5,885,278 A | 3/1999 | Fleischman | |
| 5,887,594 A | 3/1999 | LoCicero, III | |
| 5,891,141 A | 4/1999 | Rydell | |
| 5,913,870 A | 6/1999 | DeFonzo et al. | |
| 5,961,526 A | 10/1999 | Chu et al. | |
| 5,984,939 A | 11/1999 | Yoon | |
| 5,997,536 A | 12/1999 | Osswald et al. | |
| 6,016,452 A | 1/2000 | Kasevich | |
| 6,032,077 A | 2/2000 | Pomeranz | |
| 6,045,570 A | 4/2000 | Epstein et al. | |
| 6,056,763 A | 5/2000 | Parsons | |
| 6,071,283 A | 6/2000 | Nardella et al. | |
| 6,098,629 A | 8/2000 | Johnson et al. | |
| 6,099,518 A | 8/2000 | Adams et al. | |
| 6,117,101 A | 9/2000 | Diederich et al. | |
| 6,117,148 A | 9/2000 | Ravo et al. | |
| 6,132,428 A | 10/2000 | VanDusseldorp | |
| 6,146,401 A | 11/2000 | Yoon et al. | |
| 6,152,920 A | 11/2000 | Thompson et al. | |
| 6,171,319 B1 | 1/2001 | Nobles et al. | |
| 6,190,382 B1 | 2/2001 | Ormsby et al. | |
| 6,190,384 B1 | 2/2001 | Ouchi | |
| 6,193,129 B1 | 2/2001 | Bittner et al. | |
| 6,258,086 B1 | 7/2001 | Ashley et al. | |
| 6,270,501 B1 | 8/2001 | Freiberg et al. | |
| 6,279,809 B1 | 8/2001 | Nicolo | |
| 6,319,230 B1 | 11/2001 | Palasis et al. | |
| 6,324,418 B1 | 11/2001 | Crowley et al. | |
| 6,346,099 B1 | 2/2002 | Altman | |
| 6,354,297 B1 | 3/2002 | Eiseman | |
| 6,358,262 B1 | 3/2002 | Chan et al. | |
| 6,454,727 B1 | 9/2002 | Burbank et al. | |
| 6,475,226 B1 | 11/2002 | Belef et al. | |
| 6,478,794 B1 | 11/2002 | Trapp et al. | |
| 6,494,881 B1 | 12/2002 | Bales et al. | |
| 6,535,764 B2 | 3/2003 | Imran et al. | |
| 6,572,615 B2 | 6/2003 | Schulze et al. | |
| 6,592,608 B2 | 7/2003 | Fisher et al. | |
| 6,623,494 B1 | 9/2003 | Blatter | |
| 6,626,921 B2 | 9/2003 | Blatter et al. | |
| 6,632,231 B2 | 10/2003 | Radisch, Jr. | |
| 6,645,200 B1 | 11/2003 | Koblish et al. | |
| 6,660,003 B1 | 12/2003 | DeVore et al. | |
| 6,689,130 B2 | 2/2004 | Arai et al. | |
| 6,695,810 B2 * | 2/2004 | Peacock et al. | 604/99.04 |
| 6,712,775 B2 | 3/2004 | Burbank et al. | |
| 6,736,822 B2 | 5/2004 | McClellan et al. | |
| 6,736,828 B1 | 5/2004 | Adams et al. | |
| 6,743,244 B2 | 6/2004 | Blatter et al. | |
| 6,764,497 B2 | 7/2004 | Fogarty et al. | |
| 6,770,026 B2 | 8/2004 | Kan et al. | |
| 6,796,963 B2 * | 9/2004 | Carpenter et al. | 604/117 |
| 6,852,091 B2 | 2/2005 | Edwards et al. | |
| 6,852,111 B1 | 2/2005 | Lieber | |
| 6,860,892 B1 | 3/2005 | Tanaka et al. | |
| 6,866,676 B2 | 3/2005 | Kieturakis et al. | |
| 6,893,439 B2 | 5/2005 | Fleischman | |
| 6,899,721 B2 | 5/2005 | Sferco | |
| 6,921,361 B2 | 7/2005 | Suzuki et al. | |
| 6,932,833 B1 | 8/2005 | Sandoval et al. | |
| 6,936,014 B2 | 8/2005 | Vetter et al. | |
| 6,936,024 B1 | 8/2005 | Houser | |
| 6,949,099 B2 | 9/2005 | Shiro et al. | |
| 6,951,566 B2 | 10/2005 | Lary | |
| 6,964,660 B2 | 11/2005 | Maguire et al. | |
| 6,971,989 B2 | 12/2005 | Yossepowitch | |
| 6,994,705 B2 | 2/2006 | Nobis et al. | |
| 7,029,471 B2 | 4/2006 | Thompson et al. | |
| 7,063,682 B1 | 6/2006 | Whayne et al. | |
| 7,063,712 B2 | 6/2006 | Vargas et al. | |
| 7,089,045 B2 | 8/2006 | Fuiamaono et al. | |
| 7,252,665 B2 * | 8/2007 | Starkebaum et al. | 606/41 |
| 2001/0009985 A1 | 7/2001 | Durgin et al. | |
| 2001/0047177 A1 | 11/2001 | Kasten | |
| 2001/0053909 A1 | 12/2001 | Nakada | |
| 2002/0055757 A1 | 5/2002 | Torre et al. | |
| 2002/0077642 A1 | 6/2002 | Patel et al. | |
| 2002/0139379 A1 | 10/2002 | Edwards et al. | |
| 2002/0165589 A1 | 11/2002 | Imran et al. | |
| 2003/0045811 A1 | 3/2003 | Hinchliffe et al. | |
| 2003/0181901 A1 | 9/2003 | Maguire et al. | |
| 2004/0148034 A1 | 7/2004 | Kagan et al. | |
| 2005/0038462 A1 | 2/2005 | Lubock et al. | |
| 2005/0149099 A1 * | 7/2005 | Yamano et al. | 606/192 |
| 2005/0209653 A1 | 9/2005 | Herbert et al. | |
| 2005/0222567 A1 | 10/2005 | Ouchi | |
| 2005/0234294 A1 | 10/2005 | Saadat et al. | |
| 2005/0247320 A1 | 11/2005 | Stack et al. | |
| 2006/0095079 A1 | 5/2006 | Gerber | |
| 2006/0100614 A1 | 5/2006 | Long | |
| 2006/0189889 A1 | 8/2006 | Gertner | |

FOREIGN PATENT DOCUMENTS

| | | |
|---|---|---|
| WO | WO2006/074060 | 7/2006 |

* cited by examiner

FIG. 5A
FIG. 5B
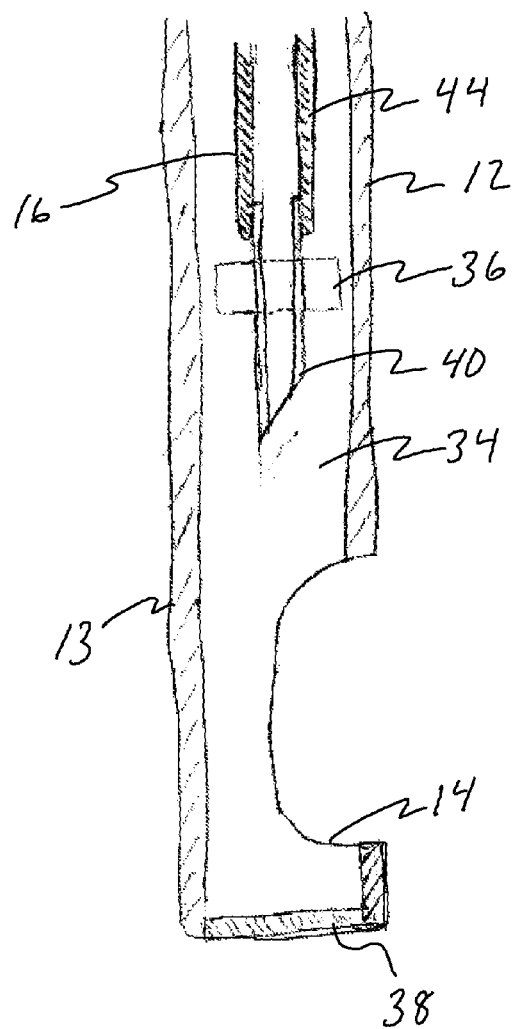
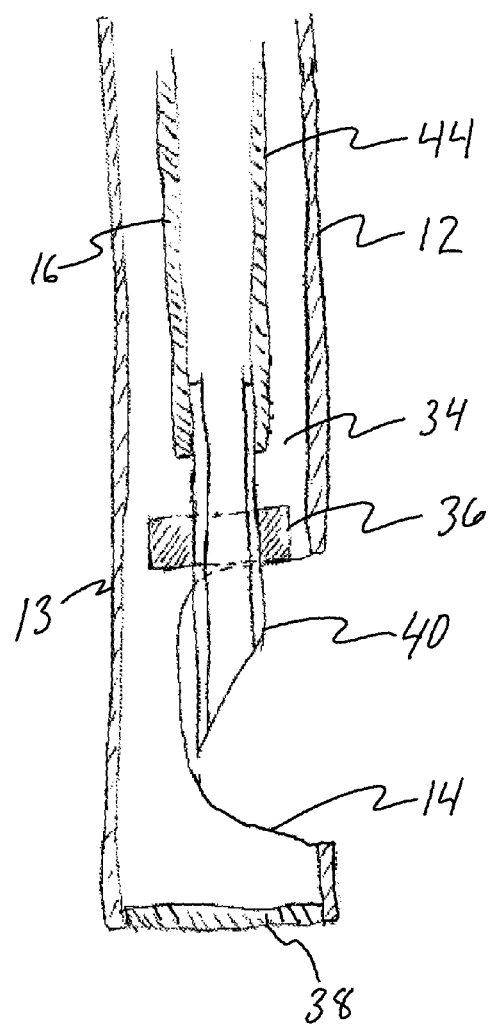

FIG. 7A
FIG. 7B
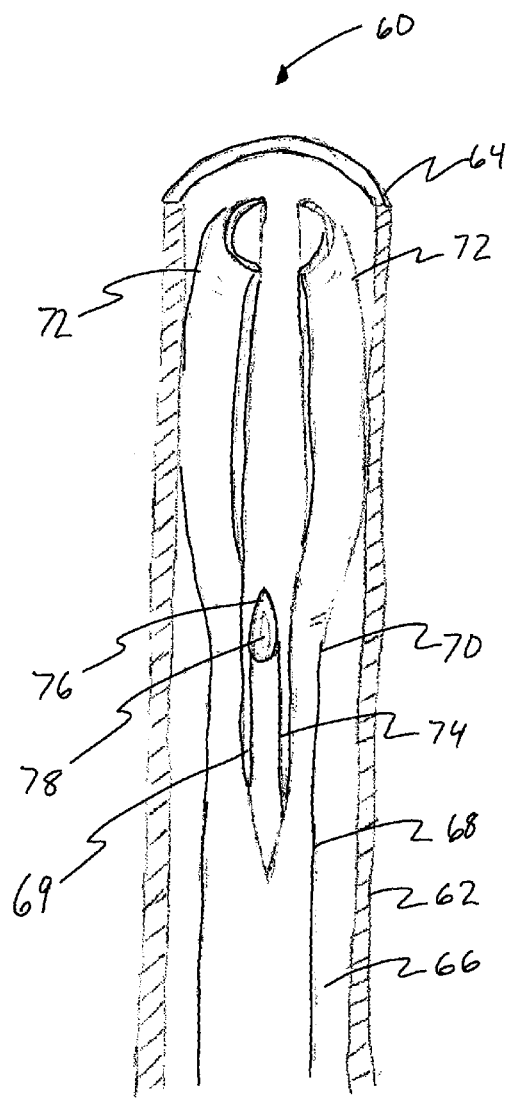
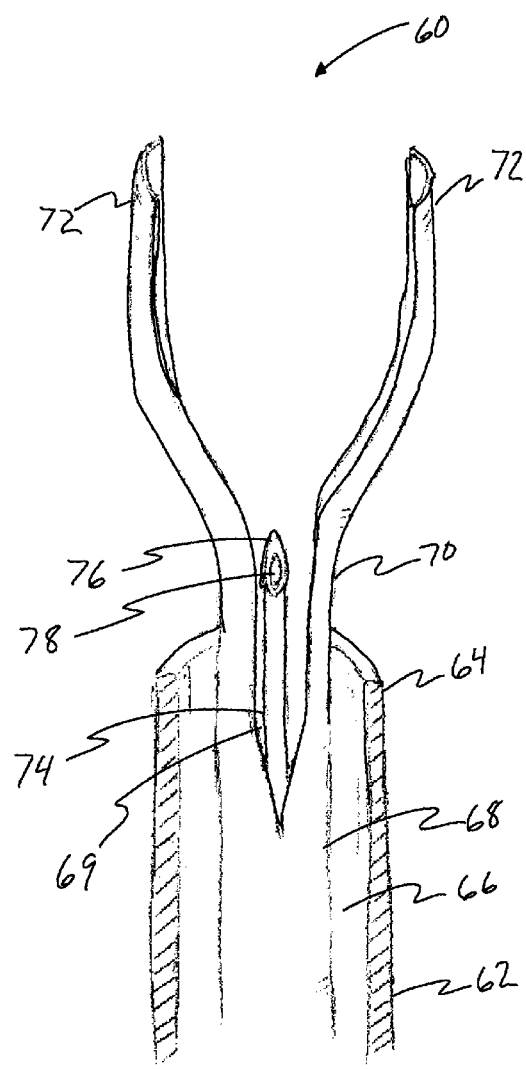

FIG. 15A
FIG. 15B
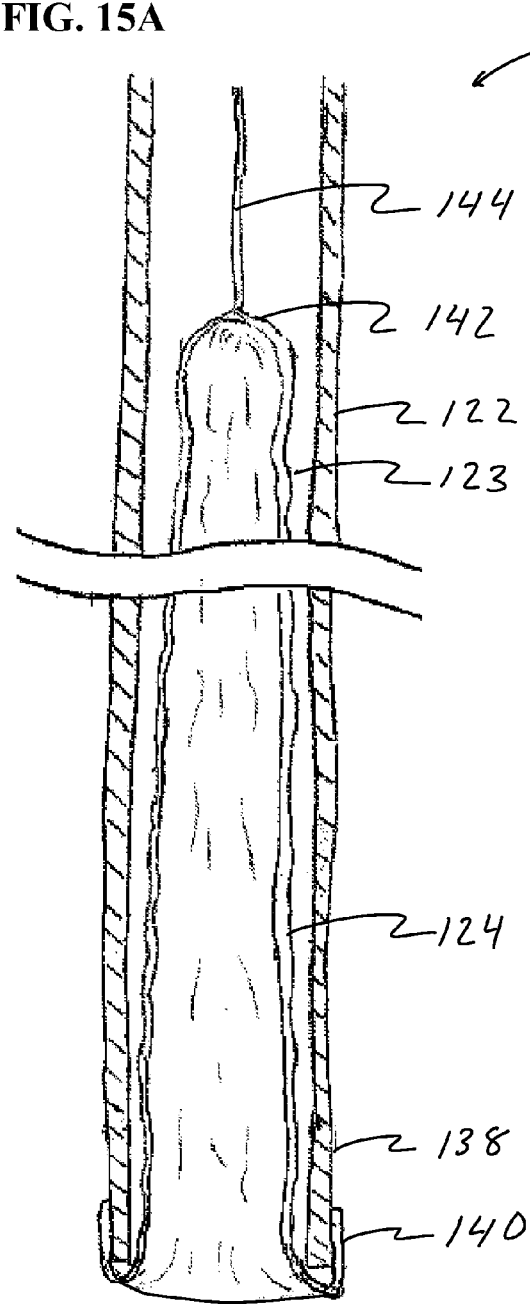
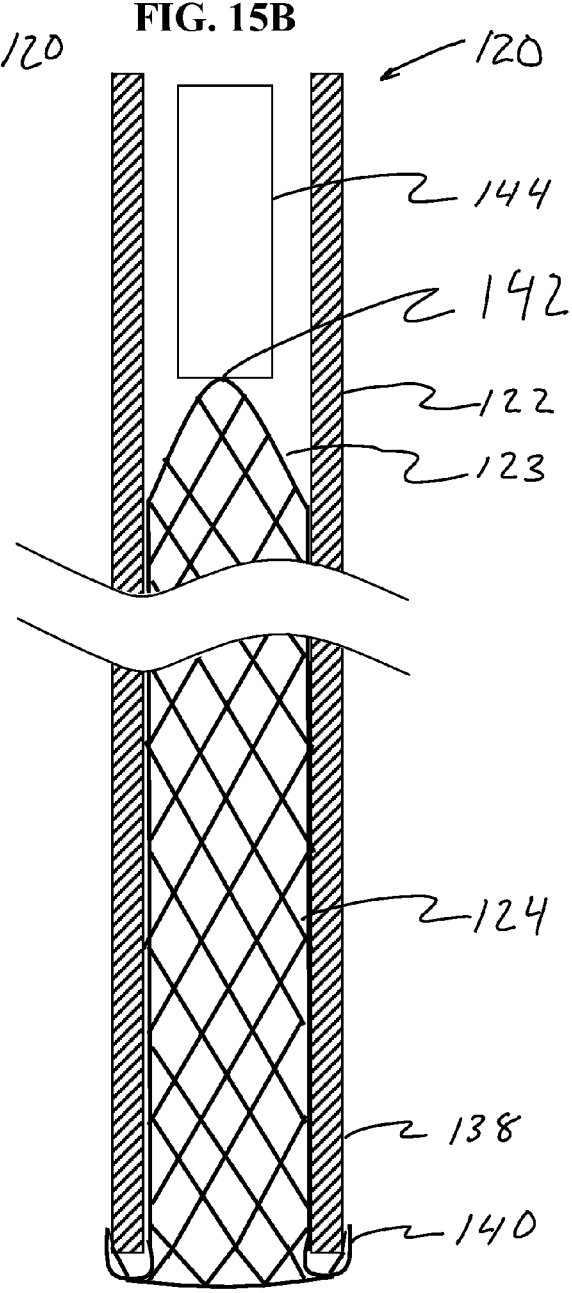

FIG. 29A
FIG. 29B
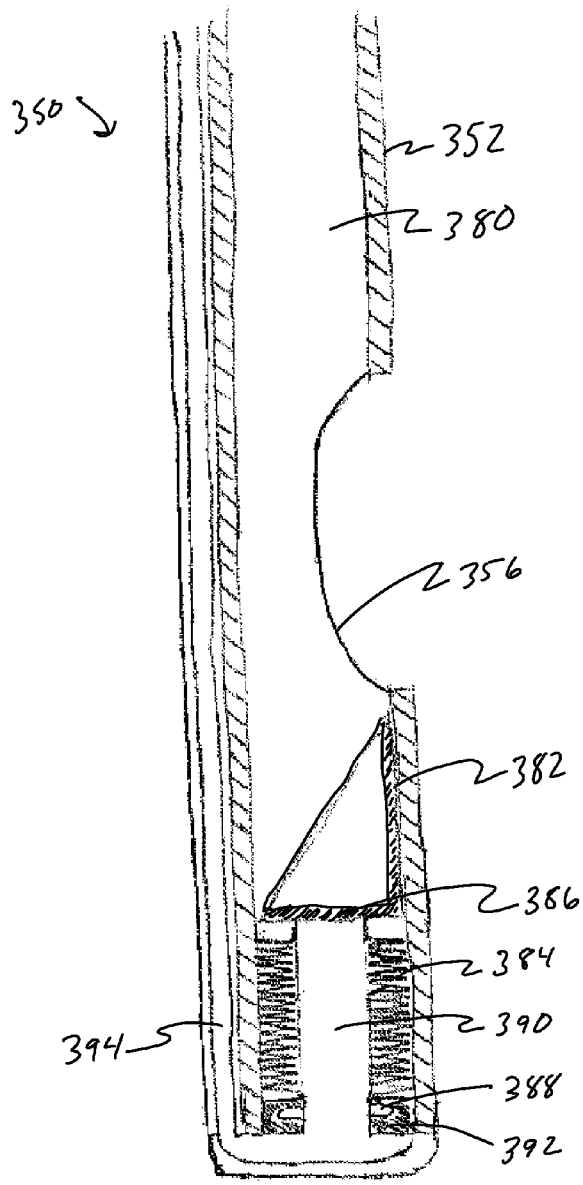
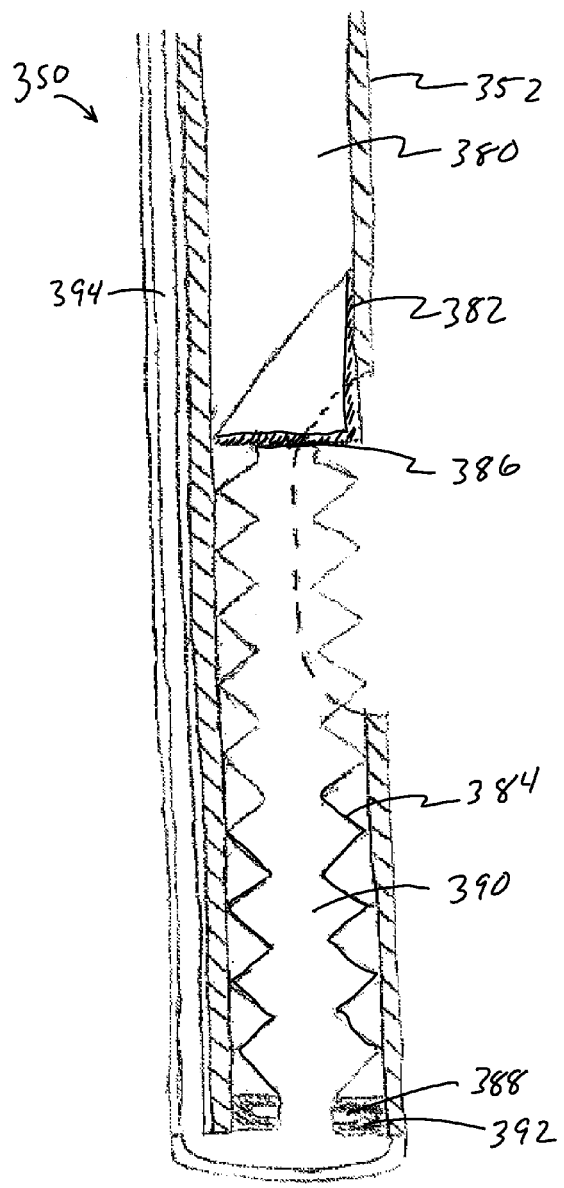

METHODS AND SYSTEMS FOR PERFORMING SUBMUCOSAL MEDICAL PROCEDURES

FIELD OF THE INVENTION

The present invention relates to a safe access needle injection instrument, a submucosal tunneling instrument, a submucosal dissection instrument, a mucosal resection device, a system and a method for performing submucosal medical procedures in a desired area of the digestive tract using an endoscope.

BACKGROUND OF THE INVENTION

The field of gastrointestinal endoscopy has for many years focused on diagnostic and therapeutic techniques to observe, modify and remove tissues located in the digestive tract. General endoscopic procedural techniques such as visualizing, dilating, cutting and manipulating tissue have been accomplished using flexible devices such as endoscopes, balloons, snares and electrosurgical tools well known in the art.

While many of these devices and techniques have been useful in identifying and removing some neoplastic lesions of the mucosal layer as well as providing access to general locations within the digestive tract for the placement of submucosal implants, there are some lesions and areas of the digestive tract which are extremely difficult to resect or access. For example, the en bloc removal of large flat mucosal lesions presents numerous problems for current endoscopic tools and techniques. In addition, to effectively diagnosis some disorders (gastric motility, irritable bowel syndrome, chronic intestinal pseudo-obstruction, etc.) a biopsy of the muscular wall or the myenteric plexus may be necessary. Currently, access to these types of specimens requires full thickness biopsies which can be particularly difficult from an endoscopic approach requiring extremely skilled closure techniques.

There have been some advances in endoscopic techniques to resect flat lesions of the mucosal layer generally termed, Endoscopic Mucosal Resection (EMR). One of these EMR techniques, "lift and cut", involves the injection of saline or other biocompatible solution beneath the lesion in an attempt to raise the lesion thereby changing the geometry to make it suitable for resection using conventional snare devices.

Modifications to this technique are disclosed in U.S. Pat. No. 5,651,788 in which a lesion is identified and an injection catheter is used to inject saline to elevate the lesion. A ligator is attached to the distal end of the endoscope and suction is applied to the lesion to bring the tissue into the ligator. A ligator band is then applied to the tissue to form a banded mushroom-like polyp which is suitable for removal with an electrosurgical snare.

Alternatively U.S. Pat. No. 5,961,526 discloses a coaxial needle and severing snare assembly in which a needle is used to pierce tissue adjacent a target lesion to elevate the lesion with saline. Once the lesion is elevated, the needle is retracted from the tissue and the snare is extended from the needle lumen to surround the lesion. The lesion is then aspirated into an aspiration cylinder adjacent the distal end of the endoscope and the snare is cinched to sever the tissue surrounding the lesion.

While EMR techniques have been shown to be effective in treating some flat neoplastic lesions there are limitations and complications associated with these techniques. A major limitation associated with this technique is the size of the lesion that can be resected. Generally, these EMR techniques are suitable only for resecting mucosal lesions which are less than 2 cm in diameter. While larger or irregular shaped lesions may be resected in a piecemeal fashion, this is undesirable since small portions of the lesion may remain. Another limitation of these techniques includes uncertainty of the area being resected. Once tissue has been suctioned into a cap ligator or aspiration cylinder, the tissue is directly adjacent the visualization means of the endoscope obscuring the field of view. One complication associated with these EMR techniques is in relation to the use of the needle injection system. Manipulating the injection catheter to position the needle through the mucosal layer into the submucosal layer can ultimately result in puncturing the muscular wall of the digestive tract which may lead to infection or peritonitis. Another complication associated with EMR techniques is damage to the underlying muscular layer. Saline and other non-viscous fluids used to elevate the lesion dissipate relatively quickly after injection into the submucosal layer, such that portions of the underlying muscular layer may be included in the suctioned tissue and inadvertently damaged when using the electrosurgical tool for resection.

In order to overcome some of the size, irregular shapes and visualization limitations associated with EMR techniques, a new procedure called Endoscopic Submucosal Dissection (ESD) has been developed. With this procedure the periphery of the target resection area, which includes the lesion, is marked. An injection catheter is used to deliver a viscous fluid within the submucosal layer, which does not readily dissipate, throughout the target resection area. Once the target resection area has been elevated, an incision is made through the mucosal layer at the edge of the resection area using an electrosurgical needle knife. The physician uses the needle knife to cut the mucosal layer along the periphery of the target resection area. Once the boundary of the resection area has been cut, the physician then uses the needle knife to manually cut the submucosal connective tissue binding the mucosal layer to the muscular wall. Once the physician has completed the submucosal dissection, the mucosal layer is free to be removed in one piece. While this procedure allows the physician to resect large, irregular shaped lesions en bloc, it requires a high degree of skill on the part of the physician and is still subject to the complications associated with needle perforations and muscular layer injury.

In performing the ESD method of resecting a neoplastic lesion, as well as, performing a submucosal medical procedure it is apparent that dissecting the connective tissue of the submucosal space is an important step in having a successful outcome. Numerous investigators have attempted to provide ways of dissecting the submucosal connective tissue.

In U.S. Pat. No. 6,098,629 a method of implanting a submucosal esophageal bulking device is disclosed. The patent further discloses the use of a blunt dissecting member to create a submucosal pocket. In addition, the patent discloses the use of a balloon inserted into the submucosal layer to dissect the submucosal tissue when dilated to form a submucosal pocket.

In PCT Patent Application No. WO 02/089655, methods of implanting submucosal gastric implants are disclosed. The application further discloses various configurations of mechanical and electrosurgical dissection instruments for dissecting the connective tissue of the submucosal layer to form a submucosal pocket in which to place a gastric implant. Included in the description of mechanical dissection instruments are various configurations of balloon dissection instruments.

In U.S. Patent Application No. US2005/0149099, a submucosal dissection instrument, system and method are disclosed. The application further discloses an electrosurgical high frequency knife in combination with a submucosal dissection balloon. Included in the method are the steps of sequentially activating the high frequency knife to create a hole and advancing the balloon assembly into the hole with expansion of the balloon dissecting the connective tissue of the submucosal layer. These steps of the method are repeated until all of the connective tissue beneath the lesion is completely dissected.

With most of the aforementioned disclosed submucosal dissection techniques the physician is required to initially advance a significant portion of a dissection instrument into the submucosal layer while the connective tissue is generally intact. These techniques require that a pushing force be transmitted to the tip of the instrument to dissect the submucosal connective tissue. During application of this pushing force there is a risk that the tip of the instrument may injure or perforate the muscular wall or the mucosal layer.

In performing the disclosed method using the electrosurgical high frequency knife the initial hole through the mucosal layer may be visualized endocopically. Once the balloon assembly is advanced into the submucosal incision hole and expanded to create a cavity, further advancement of the high frequency knife to form a second hole must be conducted without visualization. During the second hole formation and subsequent holes, without visual confirmation of the orientation of the high frequency knife there is a risk of perforating the muscular wall or mucosal layer.

SUMMARY OF THE INVENTION

In accordance with one aspect of the present invention there is provided a safe access needle injection instrument for use in a mammal. The safe access needle injection instrument includes an elongated flexible tubular member with proximal and distal ends and a lumen extending therethrough. A tissue holding member is positioned adjacent the distal end of the tubular member. A needle member having proximal and distal ends with a lumen extending therethrough is slidably positioned within the lumen of the tubular member.

The tissue holding member is integrally formed with the tubular member and is in the form of a window member adapted to engage the mucosal tissue within the digestive tract. A seal plug is included within the lumen of the tubular member distal to the window member. When a vacuum source connected to the proximal end of the tubular member is activated the vacuum causes the mucosal tissue to be suctioned within the window member of the tissue holding member.

The needle member is coaxially disposed within the lumen of the tubular member. The distal end of the needle member is operable from a first position proximal to the window member to a second position within the window member by axially advancing the needle member relative to the tubular member. Similarly, the distal end of the needle is operable from a second position within the window member to a first position proximal to the window member by axially retracting the needle member relative to the tubular member. When a vacuum is applied to the tubular member, the mucosal tissue is suctioned within the window member of the tissue holding member. The distal end of the needle member operated from its first position to the second position to thereby pierce the mucosal layer of the tissue and enter the submucosal layer.

In accordance with another aspect of the present invention there is provided a safe access needle injection instrument for use in a mammal. The safe access needle injection instrument includes an elongated flexible tubular sheath member with proximal and distal ends and a lumen extending therethrough. A tissue holding member is positioned adjacent the distal end of the tubular sheath member. A needle member having proximal and distal ends with a lumen extending therethrough is slidably positioned within the lumen of the tubular sheath member.

The tissue holding member takes the form of a pair of operable jaws connected to the distal end of an elongate shaft member. The jaws are adapted to engage the mucosal tissue within the digestive tract. The elongate shaft member is slidably disposed within the lumen of the tubular sheath member. The jaws are operable from an open configuration in which the jaws are biased outwardly when unconstrained, to a closed configuration in which the jaws approach each other when partially or fully constrained. When the tissue holding member is positioned adjacent the distal end of the tubular sheath member and the jaws are unconstrained, proximal movement of the elongate shaft member relative to the distal end of the tubular sheath, causes the jaws to be partially constrained and move from the open configuration to the closed configuration.

The needle member is coaxially disposed within the lumen of the tubular member. The distal end of the needle member is operable from a first position proximal to the tissue holding member jaws to a second position between the tissue holding member jaws, by axially advancing the needle member relative to the elongate shaft member. Similarly, the distal end of the needle is operable from a second position between the tissue holding member jaws to a first position proximal to the tissue holding jaws by axially retracting the needle member relative to the elongate shaft member. When the jaws of the tissue holding member are positioned adjacent the mucosal tissue and are operated from an open to closed configuration, mucosal tissue is grasped and held between the jaws. The distal end of the needle member is then operated from the first position to the second position to thereby pierced the mucosal layer of the tissue and enter the submucosal layer.

In accordance with another aspect of the present invention, the needle member further includes a stop member positioned adjacent the distal end of the needle member. When the distal end of the needle member pierces the mucosal layer, the stop member engages the mucosal tissue to thereby limit the depth to which the needle penetrates through the mucosal layer. Once the stop member engages the mucosal tissue it may also seal around the needle such that fluid injected through the lumen of the needle into the submucosal layer does not exit the puncture site of the needle.

In accordance with a further aspect of the present invention, a method is provided for operating a safe access needle instrument to create a safety bleb beneath the mucosal layer in the digestive tract of a mammal. The method includes the step of providing a safe access needle injection instrument. The safe access needle injection instrument having a tubular member, tissue holding member and a needle member slidably disposed within the lumen of the tubular member. The method also includes the step of inserting the safe access needle injection instrument through a natural orifice into the digestive tract of a mammal. The method additionally includes the step operating the safe access needle injection instrument to engage mucosal tissue with the tissue holding member. The method also includes the step of piercing the mucosal layer with the needle member. The method further includes the step of injecting fluid through the needle member into the submucosal layer.

In accordance with another aspect of the present invention there is provided a safe access dissection system for use in a mammal. The safe access dissection system includes safe access needle injection instrument and an injectable dissection material. The injectable dissection material may take the form of a solution capable of dissolving the submucosal connective tissue. An example of this type of dissolving solution is sodium 2-mercaptoethanesulfanate (MESNA). Additional substances which may dissolve the submucosal connective tissue include acids and enzymes such as a peptase enzyme solution, protease/collagenase, papain, chymotrypsin and acetylcysteine. The injectable dissection material may take the form of a non-pharmacological agent and provide a pure mechanical dissection of the submucosal tissue. The mechanical injectable dissection material includes injectable solutions which solidify upon entering the submucosal space, injectable semisolid gelatins, and injectable gelled microspheres. Solutions which solidify after injection into the submucosal space may be thermosensitive polymer solutions or thermo-reversible polymer gels such as Pluronic 127. Additional injectable solidifying solutions include monomer and polymer solutions like hydrogels and cyanoacrylates which polymerize or crosslink upon contact with tissue or added chemical agents. The semisolid gelatins and gelled microspheres may be formed of natural materials such as collagen and alginates or synthetic materials like polyvinylalcohol (PVA), polyvinylpyrolidone (PVP) and acrylate polymers.

In accordance with a further aspect of the present invention, a method is provided for operating a safe access dissection system to create a dissected safety bleb beneath the mucosal layer in the digestive tract of a mammal. The method includes the step of providing a safe access needle injection instrument and a dissecting material. The safe access needle injection instrument having a tubular member, tissue holding member and a needle member slidably disposed within the lumen of the tubular member. The method also includes the step of inserting the safe access needle injection instrument through a natural orifice into the digestive tract of a mammal. The method additionally includes the step operating the safe access needle injection instrument to engage mucosal tissue with the tissue holding member. The method also includes the step of piercing the mucosal layer with the needle member. The method further includes the step of injecting a dissecting material through the needle member into the submucosal layer where the submucosal connective tissue is dissected, separating the mucosal layer from the muscular layer. The method may additionally include the step of removing the dissecting material from the mammal.

In accordance with an aspect of the present invention, there is provided a submucosal tunneling instrument. The submucosal tunneling instrument includes an elongate tubular member having proximal and distal ends and a lumen extending therethrough and an elongate expandable member located at the distal end of the tubular member. The expandable member has proximal and distal ends wherein the proximal end of the expandable member is connected to the distal end of the tubular member. The expandable member is everted, such that the distal end of the expandable member is positioned within the lumen of the tubular member.

In accordance with an aspect of the present invention, there is provided a submucosal tunneling instrument. The submucosal tunneling instrument includes an elongate tubular member having proximal and distal ends and a lumen extending therethrough and an elongate expandable member located at the distal end of the tubular member. The expandable member has proximal and distal ends wherein the proximal end of the expandable member is connected to the distal end of the tubular member. The expandable member has a first spiral configuration, in which the distal end of the expandable member is positioned within center of the rolled spiral shape, and a second extended configuration in which the proximal and distal ends of the expandable member generally take the form of a straight line shape. The expandable member is operable from a first spiral configuration to a second extended configuration. The expandable member may also include a retaining member which maintains the shape of the expandable member in its first spiral configuration during delivery and positioning of the submucosal tunneling instrument. The retaining member may take the form of a spiral shaped coil member affixed to the balloon. The spiral shaped coil member may be formed from metals or polymers which may be resilient or non-resilient.

In accordance with yet another aspect of the present invention, the submucosal tunneling instrument expandable member takes the form of a balloon. The balloon may be of the compliant or non-compliant type generally known in the art. The balloon may be formed from biocompatible polymer types such as olefins, elastomers, thermoplastic elastomers, vinyls, polyamides, polyimides, polyesters, fluropolymers, copolymers and blends of any of the aforementioned.

In accordance with still another aspect of the present invention, the expandable member takes the form of a tubular framework. The tubular framework may be constructed in different fashions such as a laser cut tube, braided and non braided mesh tubes. The tubular framework may be formed from polymers such as olefins, thermoplastic elastomers, vinyls, polyamides, polyimides, polyesters, fluropolymers, copolymers and blends of any of the aforementioned or metals such as stainless steel, nitinol and other biocompatible metallic alloys.

In accordance with another aspect of the present invention the distal end of the expandable member is connected to the distal end of a tether member. The tether member is slidably disposed with the lumen of the tubular member and has a proximal end which is connected to a handle member. The tether member takes the form of a flexible filament which may include a through lumen. The handle member may be used to adjust the length of the tether member to thereby control the length of the expandable member that is allowed to exit the lumen of the tubular member.

In accordance with a further aspect of the present invention, a method is provided for operating a submucosal tunneling instrument to create a submucosal tunnel beneath the mucosal layer in the digestive tract of a mammal. The method includes the step of creating a safety bleb beneath the mucosal layer. The method also includes the step of providing a submucosal tunneling instrument. The submucosal tunneling instrument has an elongate tubular member, and an everted expandable member located within the distal lumen of the tubular member. The method also includes the step of inserting the submucosal tunneling instrument through a natural orifice into the digestive tract of a mammal. The method additionally includes the step of forming an opening in the mucosal layer of the safety bleb. The method also includes the step of positioning the distal end of the submucosal tunneling instrument through the formed opening in the mucosal layer. The method further includes the step of operating the submucosal tunneling instrument to thereby extend and expand the expandable member from the tubular member, thereby forming a submucosal tunnel. The method then includes the step of removing the submucosal tunneling instrument from the mammal.

In accordance with another aspect of the present invention there is provided a submucosal tunneling system that includes a safe access needle injection instrument, a submucosal tunneling instrument. The submucosal tunneling system may be provided in the form of a kit.

In accordance with still another aspect of the present invention there is provided a submucosal dissecting instrument. The submucosal dissecting instrument includes an elongate tubular shaft member having proximal and distal ends and a lumen extending therethrough and an expandable member located at the distal end of the tubular shaft member. The submucosal dissecting instrument may further include a marker or markers spaced apart known distances on the shaft of the tubular member to visually determine the length to which the distal end of the tubular member has been inserted into a submucosal tunnel. The markers may additionally be made of radio-opaque material to thereby be visible under fluoroscopy.

In accordance with still yet another aspect of the present invention, the expandable member of the submucosal dissecting instrument takes the form of a balloon. The balloon may be of the compliant or non-compliant type generally known in the art. The balloon may be formed from biocompatible polymer types such as olefins, elastomers, thermoplastic elastomers, vinyls, polyamides, polyimides, polyesters, fluoropolymers, copolymers and blends of any of the aforementioned.

In accordance with a further aspect of the present invention, a method is provided for operating a submucosal dissecting instrument to create a large mucosal layer dissected area in the digestive tract of a mammal. The method includes the step of forming an elongate submucosal tunnel beneath the mucosal layer. The method also includes the step of providing a submucosal dissecting instrument. The submucosal dissecting instrument has an elongate tubular member, and an expandable member located at the distal end of the tubular member. The method also includes the step of inserting the submucosal dissecting instrument through a natural orifice into the digestive tract of a mammal. The method additionally includes the step of positioning the distal end of the submucosal dissecting instrument through an opening formed in the mucosal layer into an elongate submucosal tunnel. The method further includes the step of operating the submucosal dissecting instrument to thereby dilate the expandable member at the distal end of the tubular member, thereby forming a large mucosal layer dissected area. The method then includes the step of removing the submucosal dissecting instrument from the mammal.

In accordance with a further aspect of the present invention there is provided a submucosal tunneling and dissecting instrument. The submucosal tunneling and dissecting instrument includes an elongate first tubular member having proximal and distal ends and a lumen extending therethrough and an elongate first expandable member located at the distal end of the first tubular member. The first expandable member has proximal and distal ends wherein the proximal end of the first expandable member is connected to the distal end of the first tubular member. The first expandable member is everted, such that the distal end of the first expandable member is positioned within the lumen of the first tubular member. The submucosal tunneling and dissecting instrument also includes a second elongate tubular member having proximal and distal ends and a lumen extending therethrough and a second expandable member located at the distal end of the second tubular member. The elongate first tubular member is slidably disposed within the lumen of the elongate second tubular member, such that the distal end of the first tubular member may extend from the distal lumen of the second tubular member.

In accordance with another aspect of the present invention there is provided a submucosal dissection system that includes a safe access needle injection instrument, a submucosal tunneling instrument and a submucosal dissecting instrument. The submucosal dissection system may be provided in the form of a kit. The submucosal dissection system may include a submucosal tunneling instrument and a submucosal dissecting instrument which are integrally formed.

In accordance with an aspect of the present invention there is provided a submucosal biopsy instrument suited for obtaining a biopsy beneath the mucosal layer in the digestive tract of a mammal. The submucosal biopsy instrument includes an elongate tubular member with proximal and distal ends and a first lumen. A window member is positioned at the distal end of the elongate tubular member and is also connected to the first lumen of the tubular member. When a vacuum source is applied to the proximal end of the first lumen of the tubular member and the window member is adjacent tissue, tissue is suctioned into the window member. A tissue cutter is also positioned at the distal end of the tubular member adjacent to the window member. The tissue cutter is operable to move from a first position which is distal to the window member to a second position which is proximal to the window member. When tissue is suctioned into the window member, the tissue cutter may be operated to move from the first position to the second position, thereby severing the tissue within the window member from the surrounding tissue.

In accordance with a further aspect of the present invention the tubular member of the submucosal biopsy instrument includes a second lumen. The distal end of the second lumen is connected to an extendable bellows member having a first contracted configuration and a second extended configuration. The bellows member is positioned within the first lumen at the distal end of the tubular member and connected to the distal end of the tissue cutter. When a pressure source is coupled to the proximal end of the second lumen, pressure within the bellows member transitions the bellows member from the first contracted configuration to the second extended configuration, thereby causing the tissue cutter to move from a first position distal to the window member to a second position proximal to the window member.

In accordance with yet a further aspect of the present invention the tubular member of the submucosal biopsy instrument includes a second lumen. The distal end of the second lumen is positioned proximal to the proximal end of the window member. An elongate member having proximal and distal ends is slidably disposed within the second lumen where the distal end is connected to the tissue cutter. The tissue cutter is configured to encircle the distal end of the tubular member. Movement of the proximal end of the elongate member in a proximal direction relative to the proximal end of the tubular member causes the tissue cutter to move from a first position distal to the window member to a second position proximal to the window member. The tissue cutter may take the form of an electrosurgical cutter in which tissue suctioned into the window member may be severed, when high frequency energy is supplied to the tissue cutter and the tissue cutter is moved from the first position to the second position.

In accordance with another aspect of the present invention there is provided a method of performing a submucosal muscular biopsy using a submucosal biopsy instrument in the digestive tract of a mammal. The method includes the step of providing a submucosal biopsy instrument. The method also includes the step of positioning the distal end of the submucosal biopsy instrument through the mucosal layer adjacent the muscular wall. The method additionally includes the step of operating the submucosal biopsy instrument to sever the biopsy specimen from the surrounding tissue. The method also additionally includes the step of removing the specimen from the mammal. The method then includes the step of removing the submucosal biopsy instrument from the patient.

In another aspect of the present invention there is provided a method of performing a submucosal medical procedure for the treatment of Achalasia in a mammal. The method includes the step of forming a submucosal tunnel beneath the mucosal layer in the esophagus encompassing the lower esophageal sphincter. The method includes the step of inserting an endoscope through a mucosal opening into the area beneath the mucosal layer. The method also includes the step of visualizing the circular muscle of the lower esophageal sphincter. The method further includes the step of positioning an incision device through the mucosal layer where the distal end of the incision device is adjacent to the circular muscle. The incision device is of an endoscopic type and may be mechanical or electrosurgical in design. The method additionally includes the step of operating the incision device to make an incision in the circular muscle. The electrosurgical type incision device may include an electrical insulator on the distal tip so that the distal tip does not cut or perforate the esophagus beneath the circular muscle. The method also additionally includes the step of removing the incision device from the mammal. The method then includes closing the mucosal opening.

In accordance with still another aspect of the present invention, there is provided the method of performing a submucosal medical procedure for the treatment of Achalasia that additionally includes the step of forming a large mucosal dissected area encompassing the lower esophageal sphincter, prior to inserting an endoscope beneath the mucosal layer.

In accordance with still another aspect of the present invention there is provided a mucosal layer resection device for removing a target area of mucosal tissue in the digestive tract of a mammal. The mucosal layer resection device includes a tubular sheath having proximal and distal ends and a lumen extending therethrough. The mucosal layer resection device also includes an elongate member having proximal and distal sections and being slidably disposed within a lumen of said sheath. The elongate member has a first state in which the distal section configuration is generally linear and a second state in which the distal section configuration is generally curved. The elongate member is operable between said first and second states. The mucosal layer resection device also includes resection member slidably connected to the distal section of said elongate member such that when the elongate member is in the first or second states, the resection member may slide along a path defined by said distal section of the elongate member. The resection member may take the form of an optical, mechanical or electrosurgical incision device suitable for endoscopic use in cutting tissue.

In accordance with another aspect of the present invention the elongate member of the mucosal layer resection device is tubular having a through lumen extend from the proximal section to the distal section. A slot is formed through the wall of the distal section of the elongate member. The resection member is slidably disposed within the lumen of the distal section of the elongate member. The distal end of the resection member is angled and configured to extend from the lumen through the slot in the wall of the elongate member. When the proximal end of the resection member is pulled proximally, relative to the elongate member, the distal end of the resection member is moved proximally along a path defined by the slot in the distal section of the elongate member. The distal tip of the resection member may additionally include a guard to prevent damage to surrounding tissue. If the resection member takes the form of an electrosurgical incision device the guard may be formed of an electrical insulator.

In accordance with yet another aspect of the present invention there is provided a method for performing a submucosal medical procedure in which a target area of mucosal tissue is resected using a mucosal layer resection device. The method includes the step of forming a large mucosal layer dissected area in the digestive tract of a mammal defining a target area to be resected. The method also includes the step of providing a mucosal layer resection device. The method additionally includes the step of inserting the distal section of the elongate member of a mucosal layer resection device through an opening in the mucosal layer into the submucosal space beneath the target area to be resected. The method additionally also includes the step of positioning the distal section of the elongate member of a mucosal layer resection device to define a path along the submucosal boundary of the target area. The method also includes the step of positioning the distal tip of the resection member to extend through the opening in the mucosal layer. The method further includes the step of operating the mucosal layer resection device to move the proximal end of the resection member proximally thereby causing the distal end of resection member to move proximally along the path defined by the elongate member thus resecting the target area of mucosal tissue from the surrounding mucosal tissue. The method additionally further includes the step removing the mucosal layer resection device from the mammal. The method then includes the step of removing the resected mucosal tissue from the mammal.

BRIEF DESCRIPTION OF THE DRAWINGS

FIG. 5A is a partial cross-sectional view showing a first position of the needle of a safe access needle injection instrument according to an embodiment of a submucosal medical procedure system of the present invention.

FIG. 5B is a partial cross-sectional view showing a second position of the needle of a safe access needle injection instrument according to an embodiment of a submucosal medical procedure system of the present invention.

FIGS. 7A through 7C are partial cross-sectional views of a safe access needle injection instrument according to another embodiment of a submucosal medical procedure system of the present invention.

FIGS. 15A and 15B are cross-sectional views showing a submucosal tunneling instrument of a submucosal medical procedure system in accordance with an embodiment of the present invention.

FIGS. 29A and 29B are cross-sectional views showing a submucosal biopsy instrument according to an embodiment of a submucosal medical procedure system of the present invention.

DETAILED DESCRIPTION OF THE INVENTION

Methods and devices for performing submucosal medical procedures in a desired area of the digestive tract using an endoscope are described.

Figure 1:
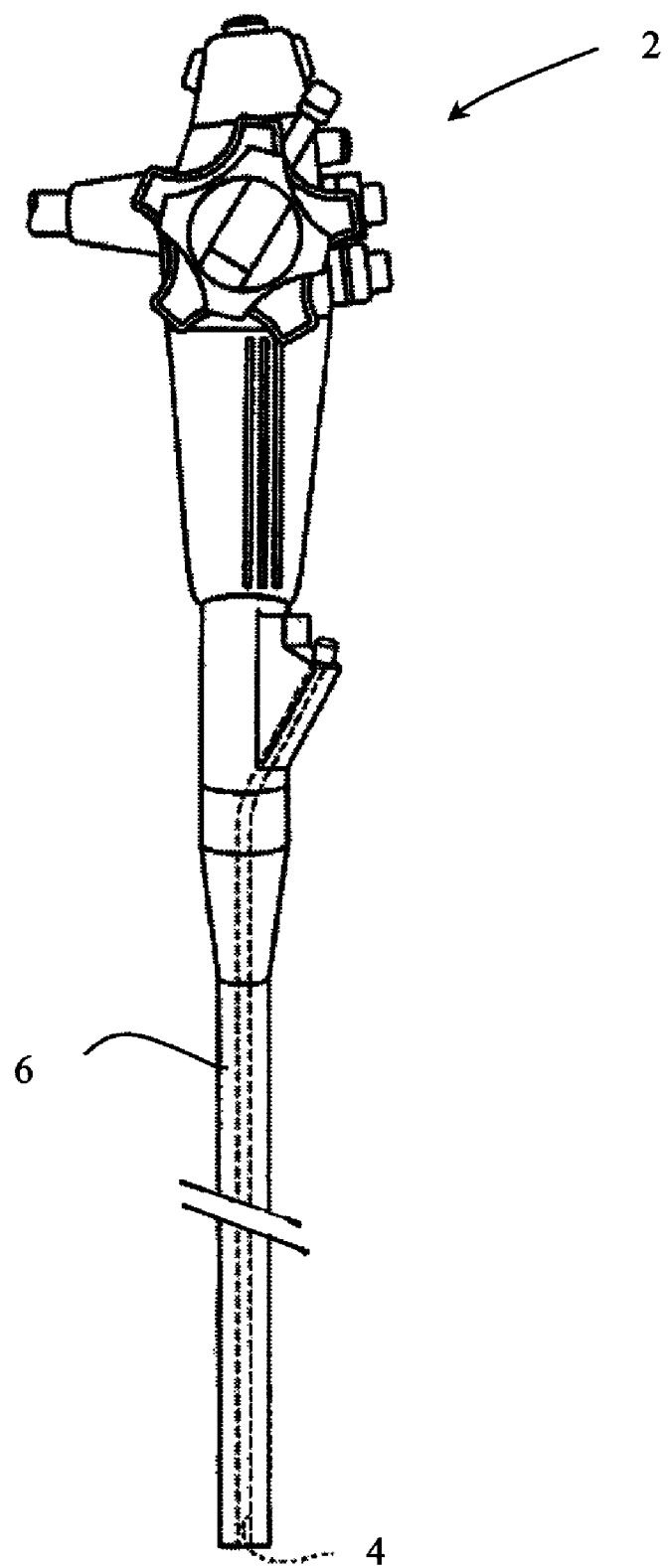
FIG. 1 is a side view of an endoscope of a submucosal medical procedure system according to an embodiment of the present invention.

FIG. 1 illustrates an endoscope 2 of the type used in endoscopic procedures and suitable for use with embodiments of the present invention. The endoscope 2 has a working channel 4 extending from a proximal portion of the endoscope to the distal end of the endoscope. The endoscope 2 also has an insertion section 6 which enters the body of a patient passing through a natural orifice such as the mouth or rectum. The insertion section 6 is generally navigated to a position with the digestive tract when performing a submucosal medical procedure. Devices for use in performing submucosal medical procedures are preferably delivered through working channel 4 of the endoscope 2; however devices may be delivered along side the insertion section 6 of the endoscope.

Figure 2:
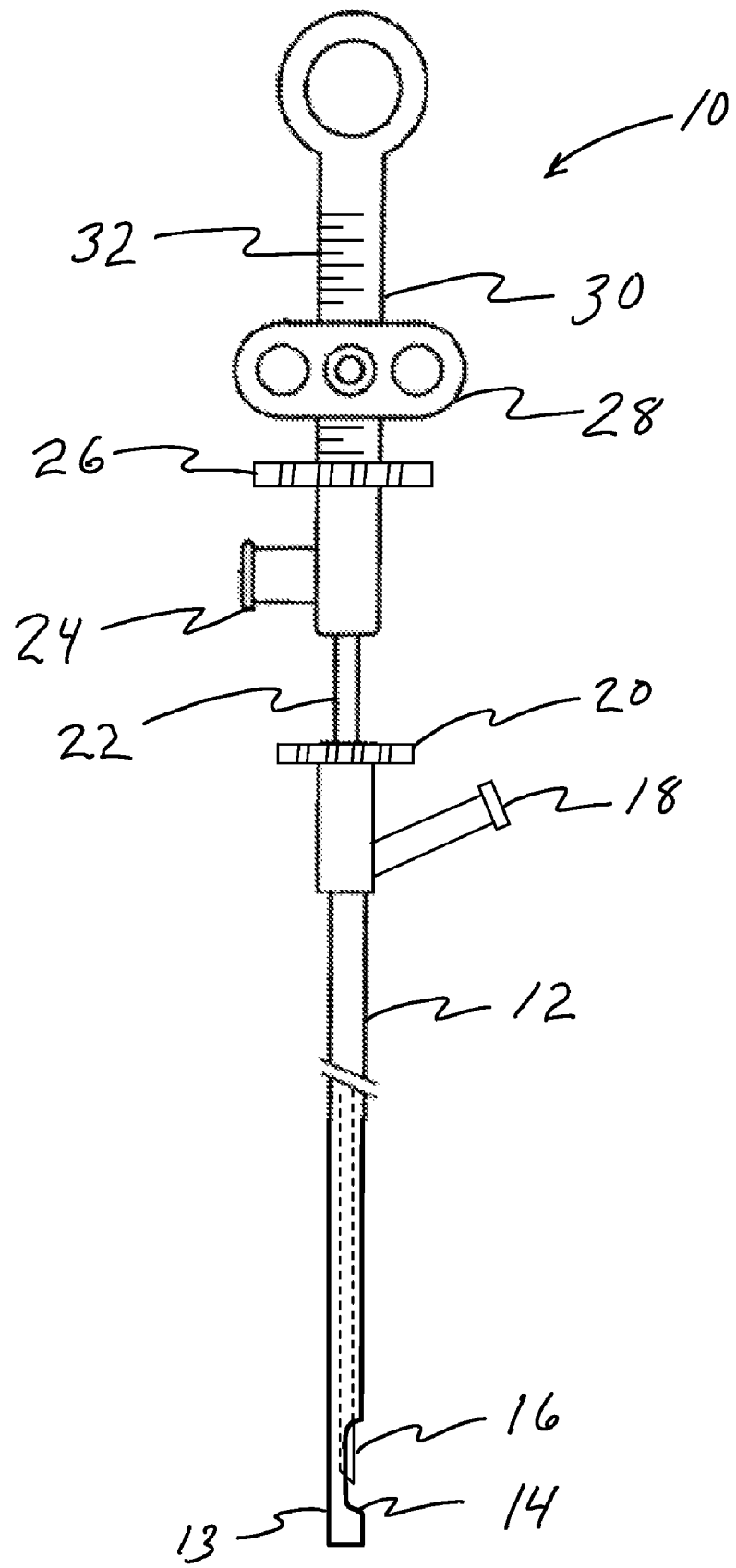
FIG. 2 is a side view of a safe access needle injection instrument according to an embodiment of a submucosal medical procedure system of the present invention.

FIG. 2 illustrates a safe access needle injection instrument 10 which is used to aid the physician in obtaining access to the submucosal layer to perform a submucosal medical procedure. The safe access needle injection instrument 10 includes a tubular shaft 12 having a distal end 13. The diameter of tubular shaft 12 is generally in the range 1 mm to 10 mm with a preferred range of 2.0 to 6.0 mm. Adjacent distal end 13, a portion of the wall of tubular shaft 12 is removed to form window member 14. Alternatively, window member 14 can be formed with a cap element coupled to the distal end of tubular shaft 12. Slidably disposed within the lumen of tubular shaft 12 is needle member 16. The proximal portion of tubular shaft includes vacuum port 18 which is capable of being coupled to a vacuum source such as a syringe or vacuum pump (not shown). Valve assembly 20 provides a releasable seal to tubular shaft 12. A handle assembly 21 is connected to tubular shaft 12 through connector tubing 22. The handle assembly 21 includes needle fluid port 24 and valve assembly 26 for injecting fluid through and sealing around the proximal portion of needle member 16. The proximal portion of needle member 16 is also connected to a needle slide member 28 positioned on handle body 30. The proximal movement of needle slide member 28 on handle body 30 causes needle member 16 to move proximally within tubular shaft 12. Distance markers 32 are located on handle body 30 to gauge the movement of needle member 16 within tubular shaft 12.

Figure 3:
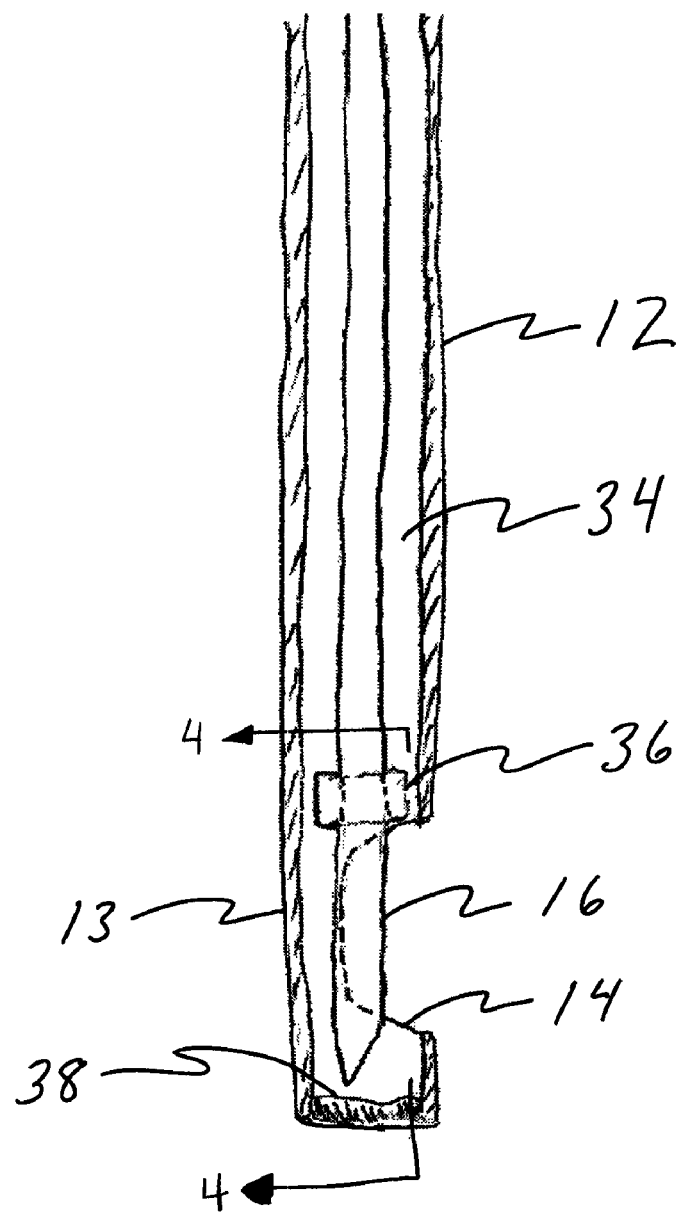
FIG. 3 is a partial cross-sectional view of a safe access needle injection instrument according to an embodiment of a submucosal medical procedure system of the present invention.
Figure 4:
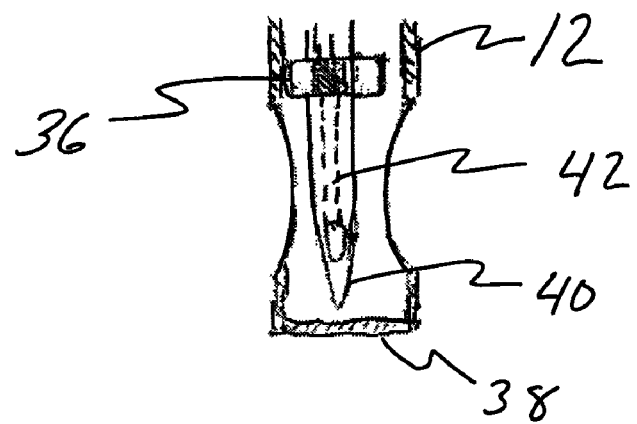
FIG. 4 is a cross-sectional view taken along 4-4 of FIG. 3.

As shown in FIGS. 3 and 4, needle member 16 is positioned within lumen 34 of tubular shaft 12. Located on the exterior of needle member 16 is stop member 36. The distal end 13 of tubular shaft 12 is closed with seal plug 38. Also shown is needle member tip 40 and needle lumen 42. Needle lumen 42 communicates needle tip 40 with needle fluid port 24 so that fluid injected through needle port 24 exits the lumen at needle tip 40.

FIGS. 5A and 5B, illustrate the actuation of needle member 16. Needle member 16 is shown in detail with needle body 44 connected to needle tip 40. Needle body 44 may be constructed of a separate material as shown or integrally formed with needle tip 40. Needle body 44 may be constructed from flexible tubing having good axial pushability. As shown in FIG. 5A, needle member 16 is in a first position in which needle tip 40 is located within lumen 34 proximal to window member 14. This is the preferred position for needle member 16 when tubular shaft 12 is deployed within the body. Upon actuation, needle member 16 is moved to a second position in which needle tip 40 is positioned within window member 14.

Figure 6A:
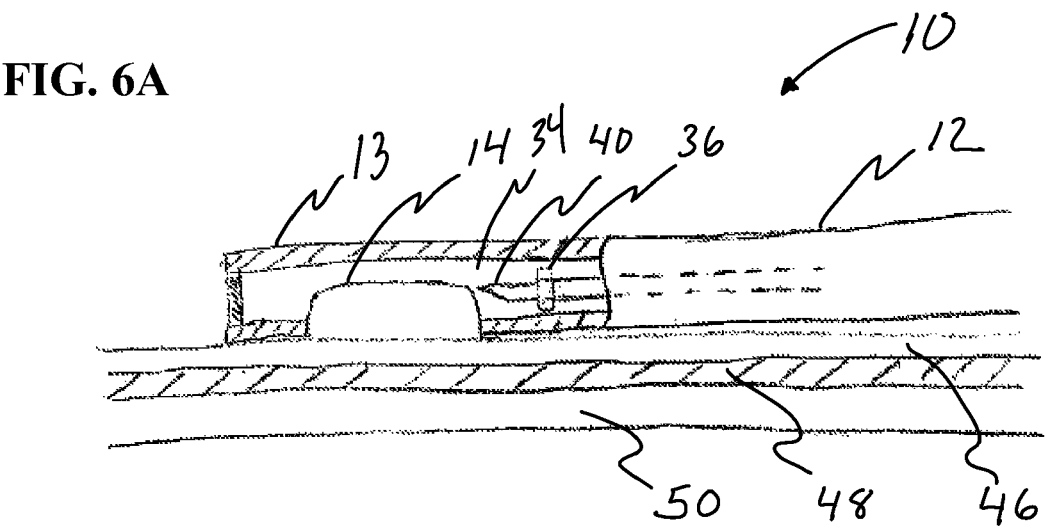
FIG. 6A through 6E are cross-sectional views showing a method creating a submucosal bleb using the safe access needle injection instrument in accordance with an embodiment of the present invention.
Figure 6B:
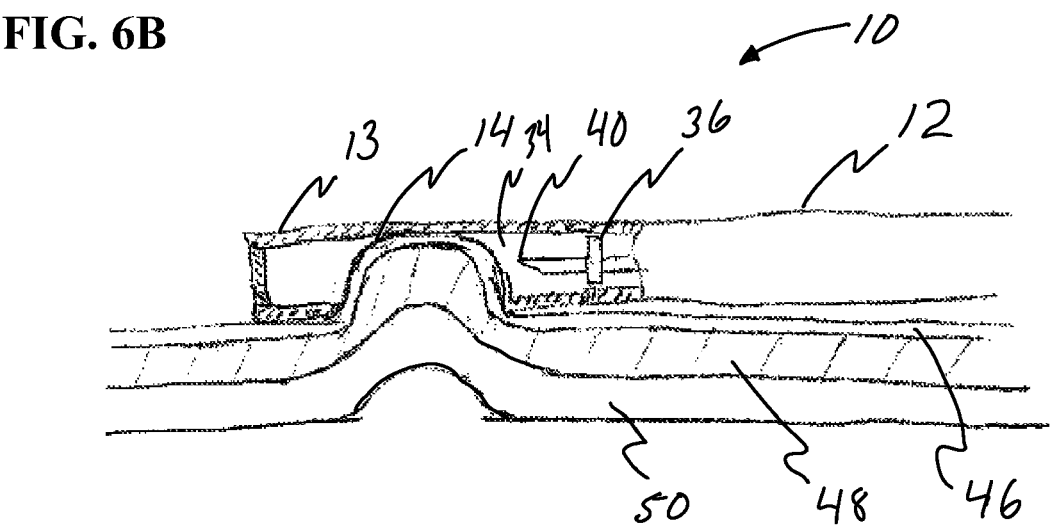
Figure 6C:
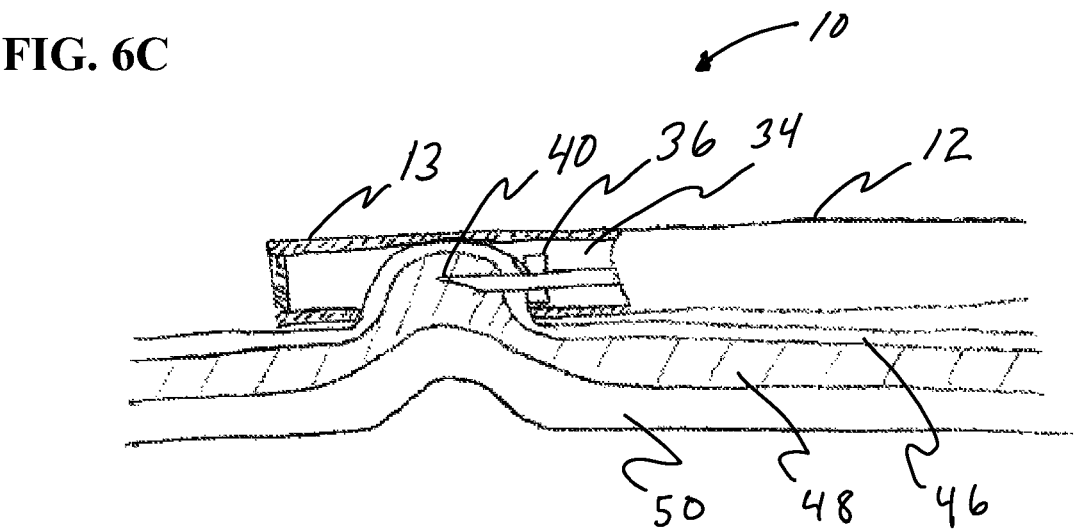
Figure 6D:
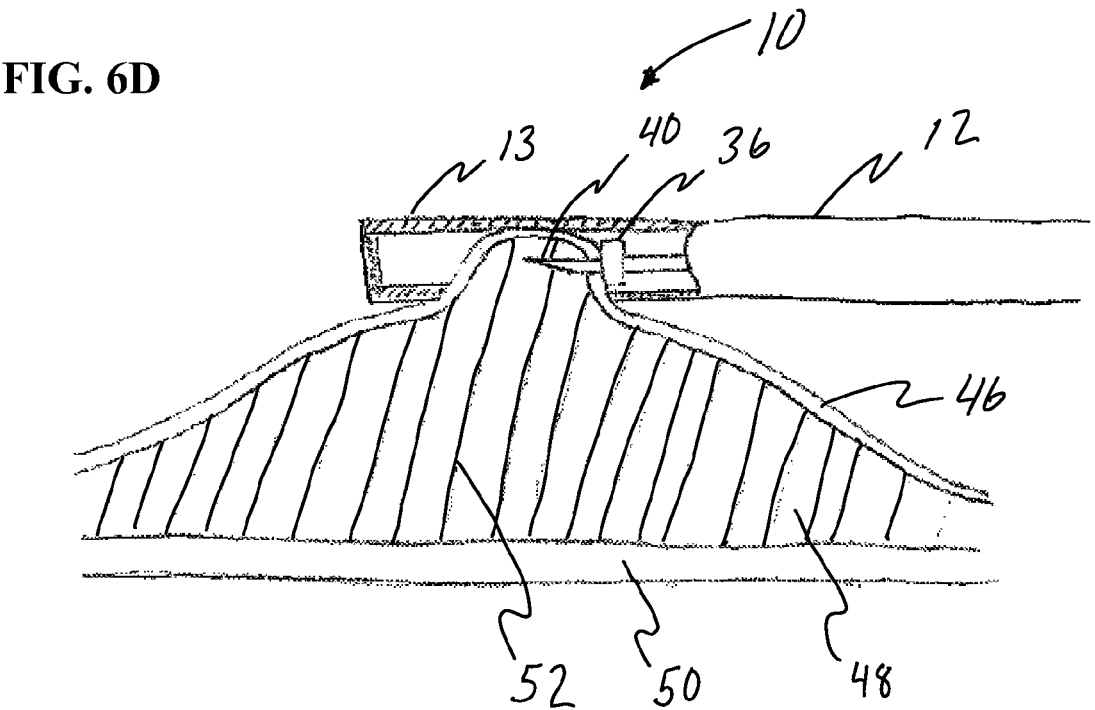
Figure 6E:
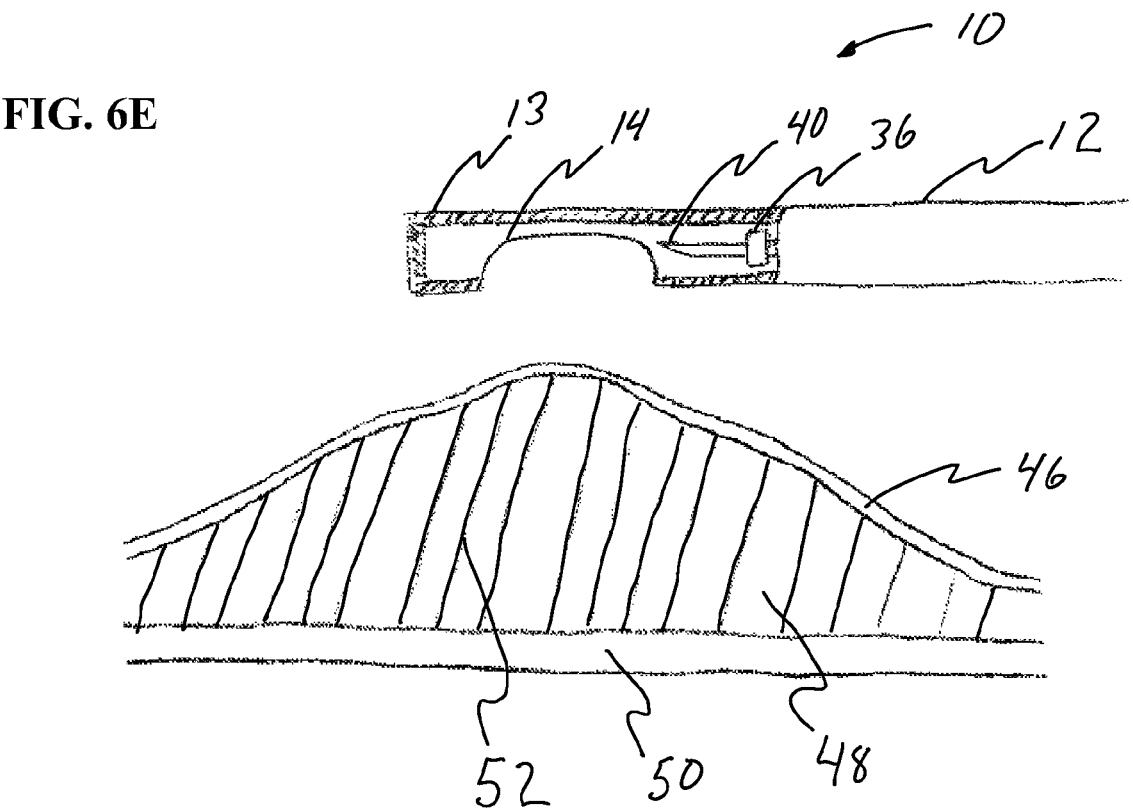

FIGS. 6A through 6E illustrate the operation of safe access needle injection instrument 10. Insertion section 6 of endoscope 2 is passed through a natural orifice in a patient and positioned at a location in the digestive tract in which to perform a submucosal procedure. Safe access needle injection instrument 10 is deployed through the working channel 4 of endoscope 2. As depicted in FIG. 6A the distal potion of safe access needle injection instrument 10 is positioned within the digestive tract adjacent mucosal layer 46. Beneath the mucosal layer are the submucosal layer 48 and the muscular layer 50. Window member 14 is oriented towards mucosal layer 46. Needle member 16 is located in a first position proximal to window member 14. A vacuum source is connected to vacuum port 18, which communicates with lumen 34, and the applied vacuum causes the tissue of the digestive tract to be suctioned into window member 14 as shown in FIG. 6B. The actuation of needle member 16 is shown in FIG. 6C as it is moved to its second position. Distal movement of needle member 16 causes needle tip 40 to move distally relative to tubular shaft 12 to thereby pierce the mucosal layer 46 and enter the submucosal layer 48 of the suctioned tissue. When needle member 16 is moved to its second position, stop member 36 engages the mucosal layer 46. Stop member 36 prevents further distal movement of needle member 16 and provides a seal around needle tip 40. A pressurized fluid source is connected to needle fluid port 24 to deliver fluid through the lumen of needle member 16 to the submucosal layer 48. As fluid enters the submucosal layer 48 from needle tip 40, as illustrated in FIG. 6D, the mucosal layer 46 is elevated forming a submucosal bleb. The fluid used to create the bleb may be of any type suitable for the environment such as solutions containing saline, hypertonic solutions of saline-epinephrine, sodium hyaluronate, poly-N-acetylglucosamine, sodium chondroitin sulfate, chitosans or other biocompatible mucopolysaccharides. Although the mucosal layer 46 is elevated to form the submucosal bleb, the submucosal connective tissue 52 is only stretched and not broken by the infusion of fluid into submucosal layer 48. Once the needle member 16 is returned to its first position and the applied vacuum to lumen 34 is discontinued, the safe access needle injection instrument 10 may be removed from the safety bleb as illustrated in FIG. 6E.

Figure 7C:
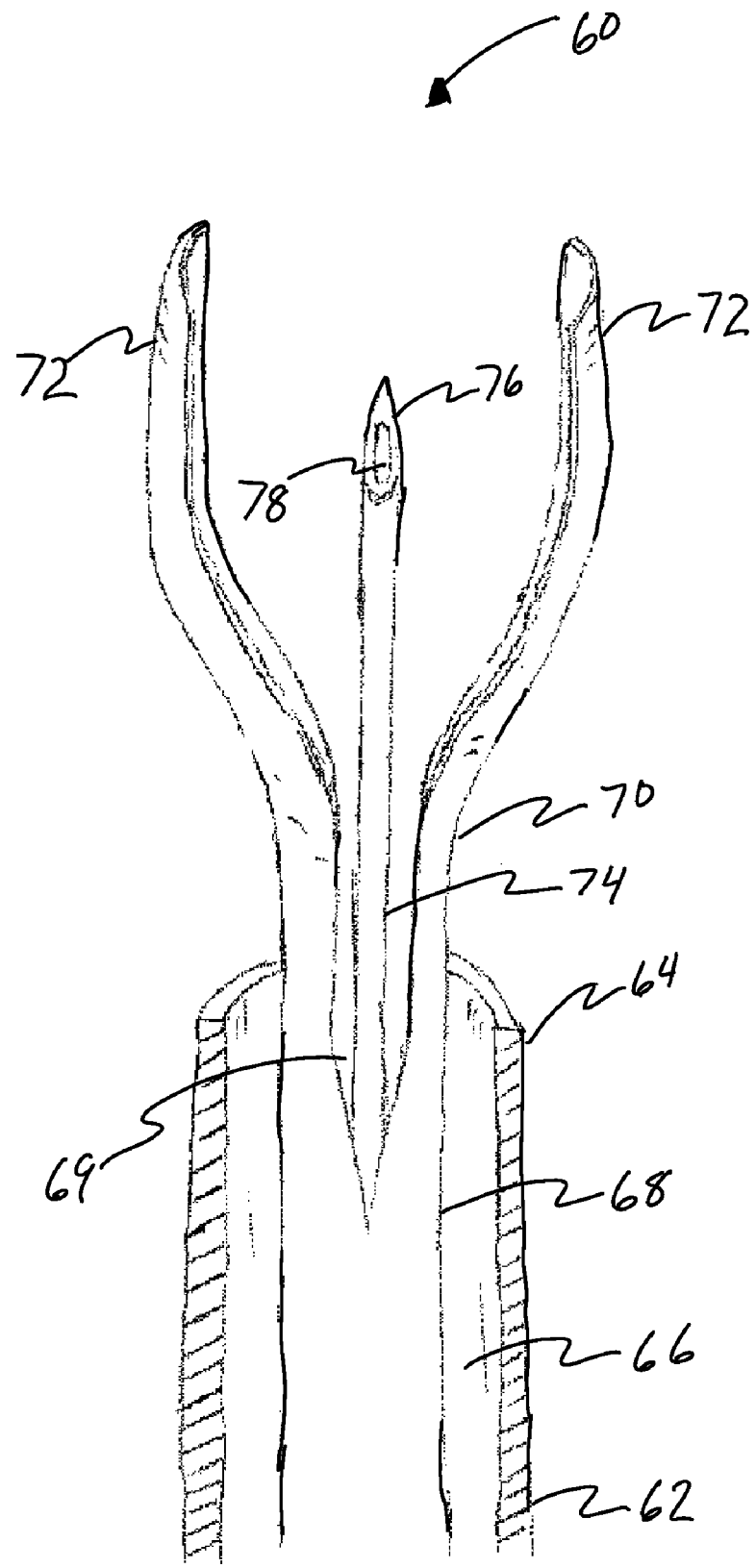

FIGS. 7A through 7C illustrate safe access needle injection instrument 60 which is another preferred embodiment of the present invention to aid the physician in obtaining access to the submucosal space when performing a submucosal medical procedure. Safe access needle injection instrument 60 includes a sheath member 62 having a proximal and distal end 64 and a lumen 66 extending therethrough. Slidably disposed within lumen 66 of sheath member 62, there is an elongate shaft member 68 having a shaft lumen 69 and distal end 70. Located adjacent to distal end 70 of elongated shaft member 68 is a pair of jaw members 72. Jaw members 72 may be formed from the wall of elongated shaft member 68. Preferably the jaw members 72 are formed of a resilient material and biased outwardly in an open configuration when unconstrained. The jaw members 72 may be formed from biocompatible resilient materials such as nitinol, stainless steel and plastics. Needle shaft 74 is slidably disposed within lumen 66 and preferably slidably disposed shaft lumen 69. Needle shaft 74 includes a needle tip 76 and a needle lumen 78. Needle lumen 78 extends from the proximal end of needle shaft 74 to needle tip 76. FIG. 7A illustrates jaw members 72 in a first state in which jaw members 72 are closed and constrained by the walls of sheath member 62 and disposed within lumen 66. Additionally, needle tip 78 of needle shaft 74 is in a first configuration in which needle tip 78 is positioned proximal to jaw members 72. By moving the elongate shaft member 68 distally relative to sheath member 62, jaw members 72 are caused to exit the lumen 66 at distal end 64 of sheath 62. FIG. 7B shows jaw members 72 in a second state in which in which the jaw members 72 are open and unconstrained after exiting lumen 66. FIG. 7C illustrates needle tip 78 of needle shaft 74 positioned in a second configuration in which needle tip 78 is positioned between jaw members 72.

Figure 8A:
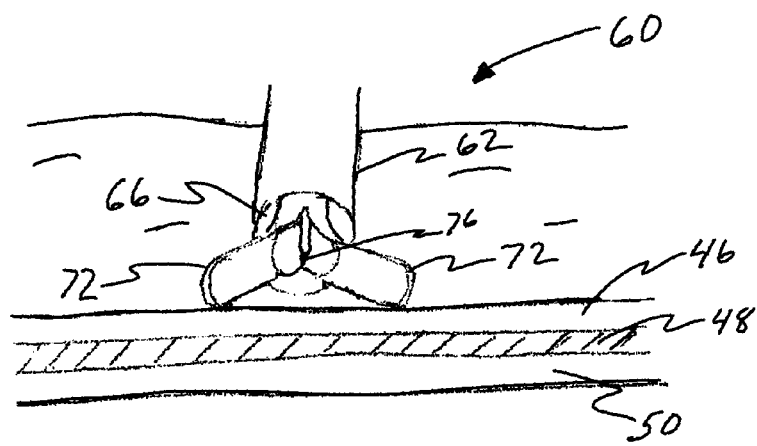
FIGS. 8A through 8E are cross sectional views showing a method creating a submucosal bleb using the safe access needle injection instrument according to another embodiment of present invention.
Figure 8B:
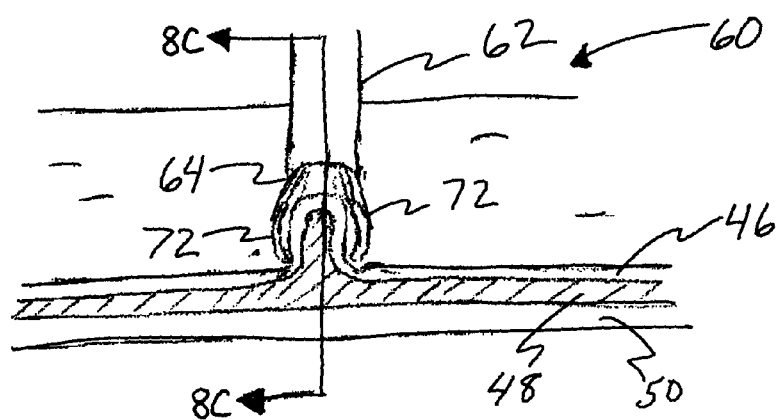
Figure 8C:
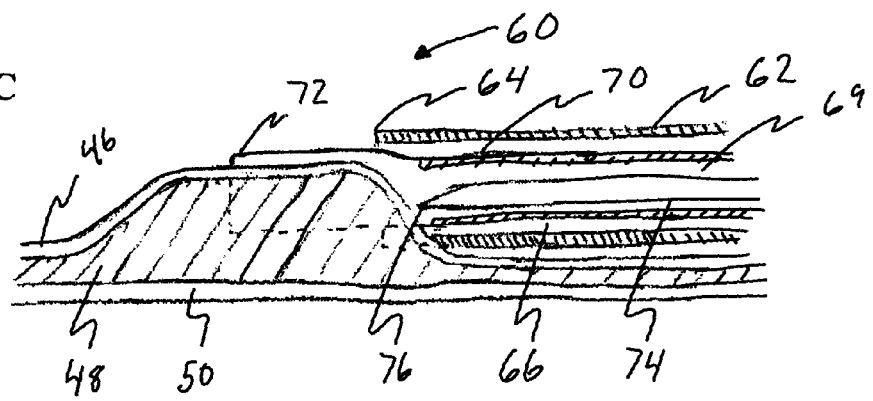
Figure 8D:
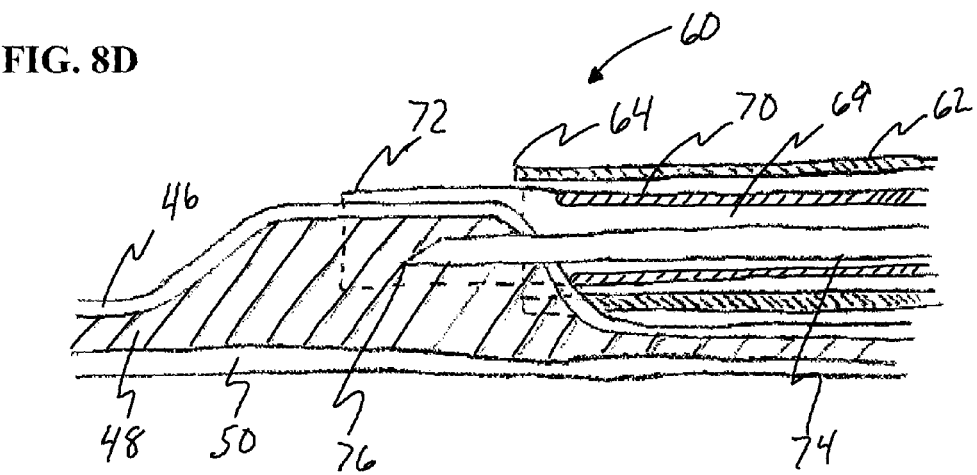
Figure 8E:
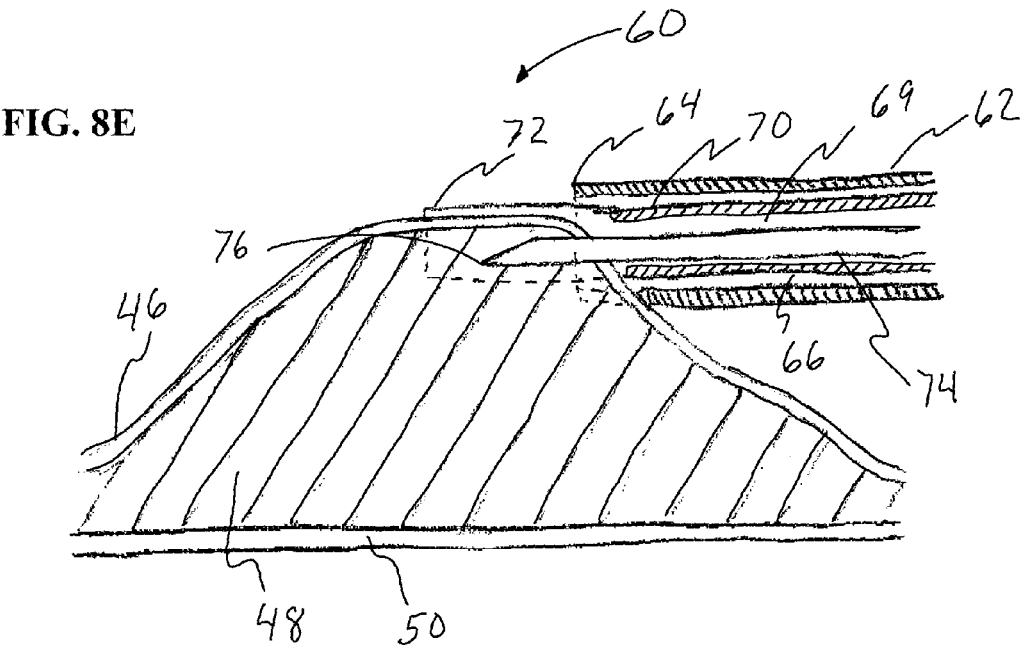

FIGS. 8A through 8E illustrates the operation of safe access needle injection instrument 60. Insertion section 6 of endoscope 2 is passed through a natural orifice in a patient and positioned at a location in the digestive tract in which to perform a submucosal procedure. Safe access needle injection instrument 60 is deployed through the working channel 4 of endoscope 2. As depicted in FIG. 8A the distal potion of safe access needle injection instrument 60 is positioned within the digestive tract adjacent mucosal layer 46. Beneath the mucosal layer are the submucosal layer 48 and the muscular layer 50. Jaw members 72 are positioned on mucosal layer 46. Needle tip 76 is located in a first position proximal to jaw members 72. Distal movement of sheath member 62 relative to the elongate shaft member causes the jaw members 72 to become partially constrained in lumen 66 and move towards a closed position thereby grasping the tissue of the digestive tract as shown in FIG. 8B. FIG. 8C is a cross-section view along section line 8C-8C in FIG. 8B showing the tissue engaged by jaw members 72. The mucosal layer 46 and submucosal layer 48 are firmly held between jaw members 72. Needle tip 76 is moved from the first position proximal to jaw members 72 to the second position between jaw members 72 thereby piercing the mucosal layer 46 and entering the submucosal layer 48 as shown in FIG. 8D. FIG. 8E illustrates the delivery of fluid through needle shaft 74 exiting needle tip 76 into the submucosal layer 48 thereby elevating mucosal layer 46 to form a submucosal bleb. The fluid used to create the bleb may be of any type suitable for the environment such as solutions containing saline, hypertonic solutions of saline-epinephrine, sodium hyaluronate, poly-N-acetylglucosamine, sodium chondroitin sulfate, chitosans or other biocompatible mucopolysaccharides.

Figure 9:
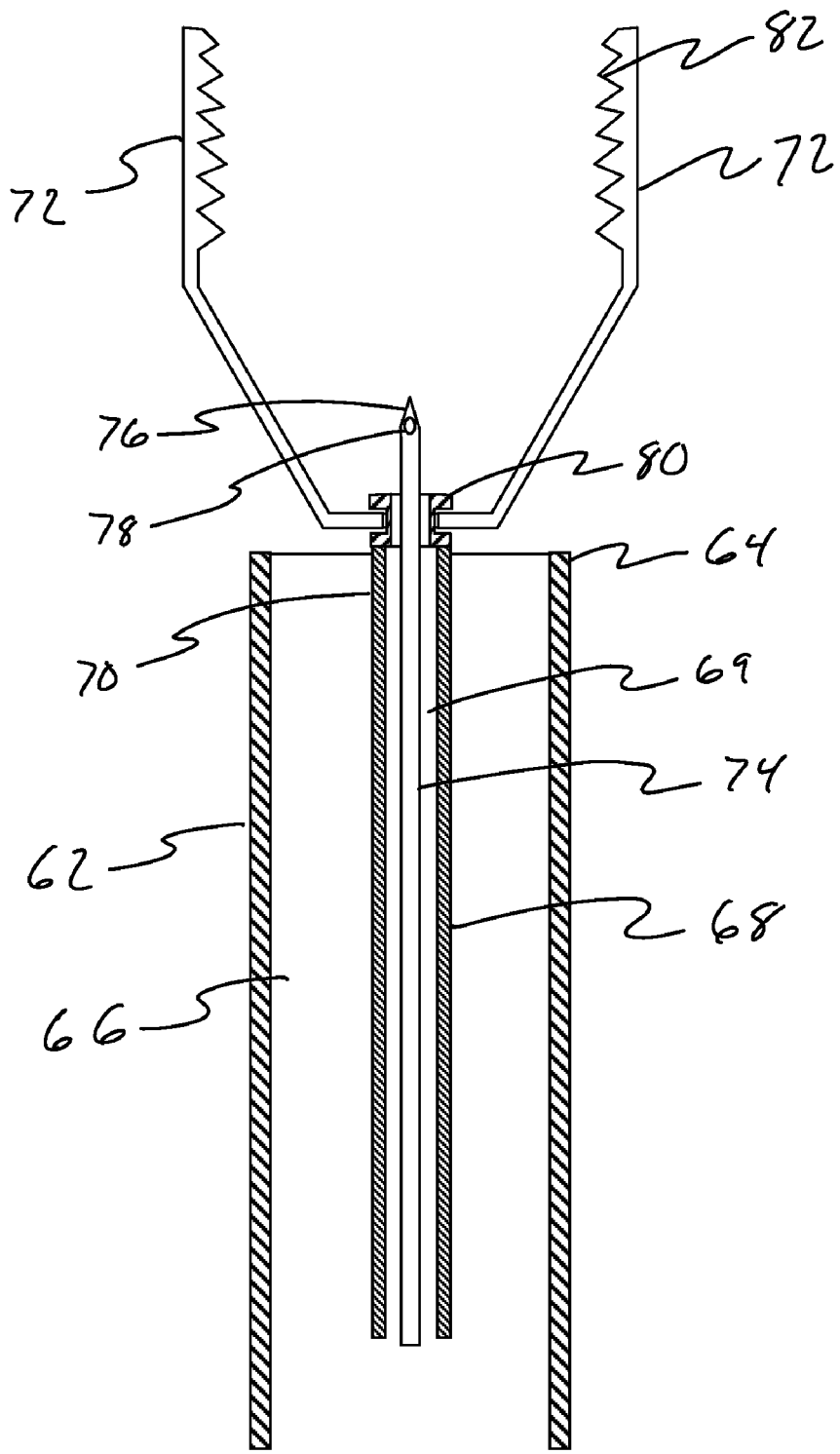
FIG. 9 is partial cross-sectional view of a safe access needle injection instrument according to another embodiment of the present invention.
Figure 10:
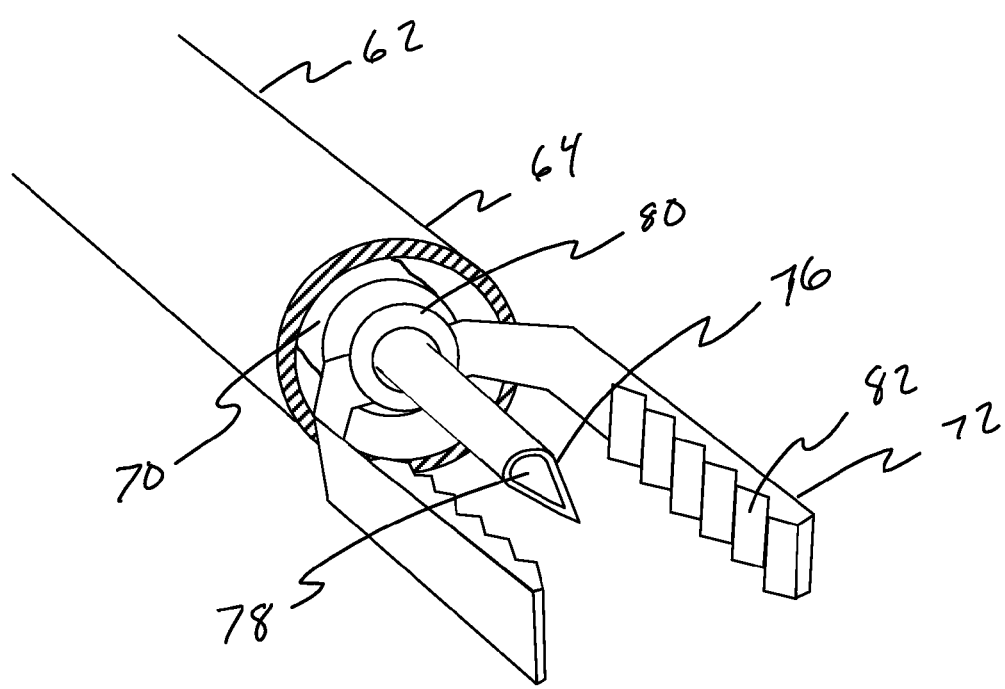
FIG. 10 is a perspective view of a safe access needle injection instrument according to another embodiment of the present invention.

FIGS. 9 and 10 show a variation of safe access needle injection instrument 60 in which jaw members 72 are coupled to distal end 70 of elongate shaft member 68 by a collar member 80. Collar member 80 is joined to distal end 70 by suitable means known in the art such as gluing, soldering or welding. Jaw members 72 are connected to collar member 80 in a way that allows the jaw members 72 to rotate relative to distal end 70 of elongate shaft member 68. The rotational movement of jaw members 72 allows the physician to quickly orient the jaw members 72 relative the surface of the tissue surface within the digestive tract. Although jaw members 72 are connected to collar member 80, proximal movement of elongate shaft member 68 relative to sheath member 62 will cause jaw members 72 to move to a closed position within the lumen 66 of sheath member 62. Collar member 80 includes an aperture through which needle shaft 74 may extend in a slidable fashion. Additionally, jaw members 72 include a tissue grasping surface 82 that facilitates the engagement of tissue within the digestive tract. While tissue grasping surface 82 is shown in the form of a serrated surface, it may also take the form of a knurled surface or a surface containing multiple protrusions or dimples to improve the tissue grasping ability of jaw members 72. Tissue grasping surface 82 may be integrally formed with jaw members 72 or bonded to jaw members 72. Tissue grasping surface 82 may be formed of metals, polymers or composite materials.

Figure 11A:
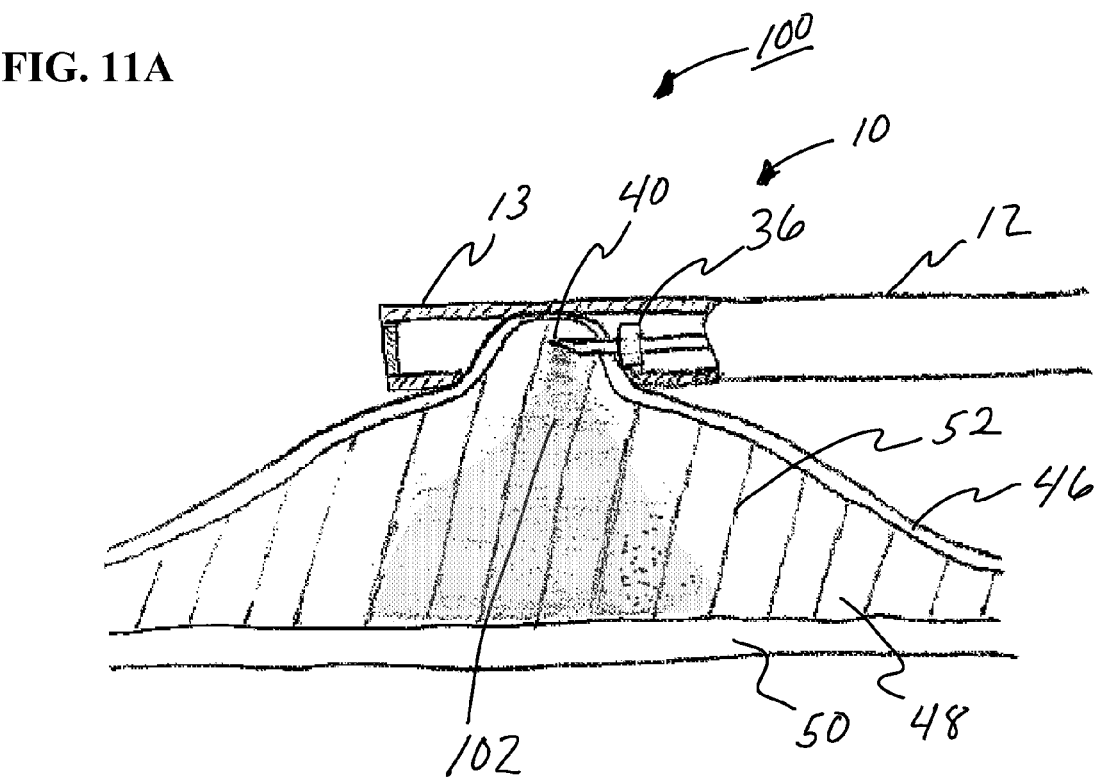
FIGS. 11A and 11B are cross-sectional views showing a method for dissecting a submucosal layer according to an embodiment of the present invention.
Figure 11B:
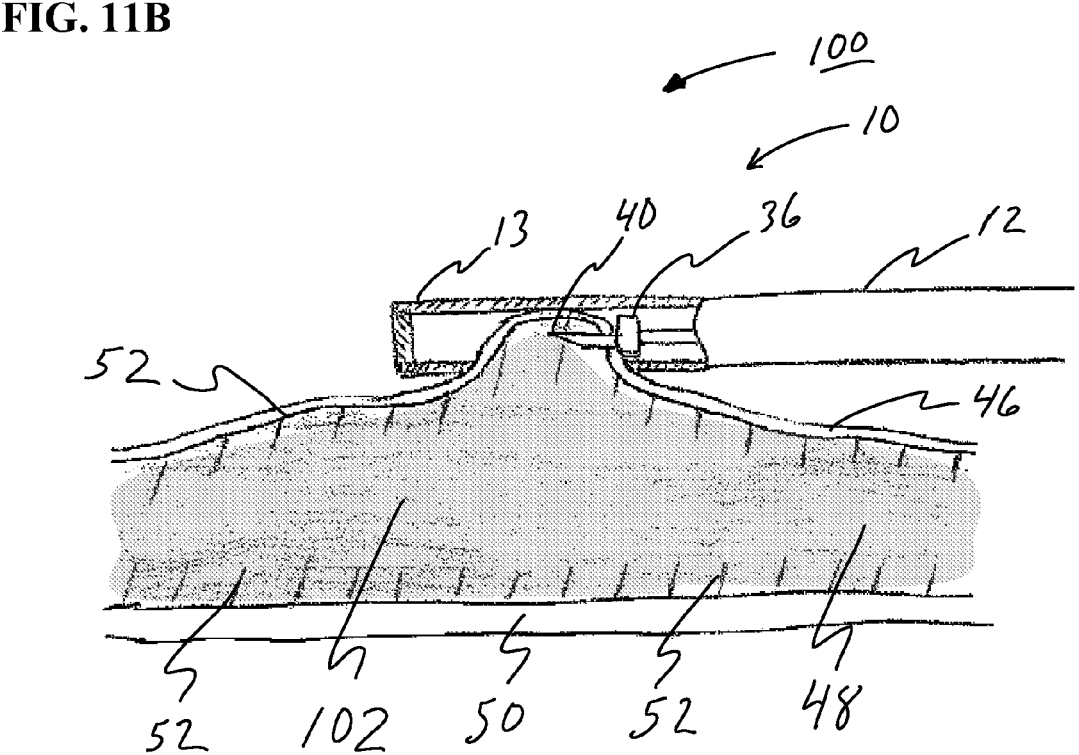

FIGS. 11A and 11B show a safe access dissection system 100 of the present invention that includes a safe access needle injection instrument 10 and an injectable dissection material 102. The injectable dissection material 102 takes the form of a solution capable of dissolving the submucosal connective tissue. An example of this type of dissolving solution is sodium 2-mercaptoethanesulfanate (MESNA). Additional substances which may dissolve the submucosal connective tissue include acids and enzymes such as a peptase enzyme solution, protease/collagenase, papain, chymotrypsin and acetylcysteine. A safe access needle injection instrument 10 is used to create a safety bleb beneath the mucosal layer 46 in the digestive tract of a mammal. Once the safety bleb is formed, the injectable dissection material 102 may be delivered through needle tip 40 into the submucosal layer 48 as shown in FIG. 11A. Injectable dissection material 102 begins to breakdown the stretched submucosal connective tissue 52. Under the force imparted by the distention of the bleb, the submucosal connective tissue 52 breaks, thereby causing the mucosal layer 46 to become detached from muscular layer 50 in bleb region as shown in FIG. 11B.

Figure 12A:
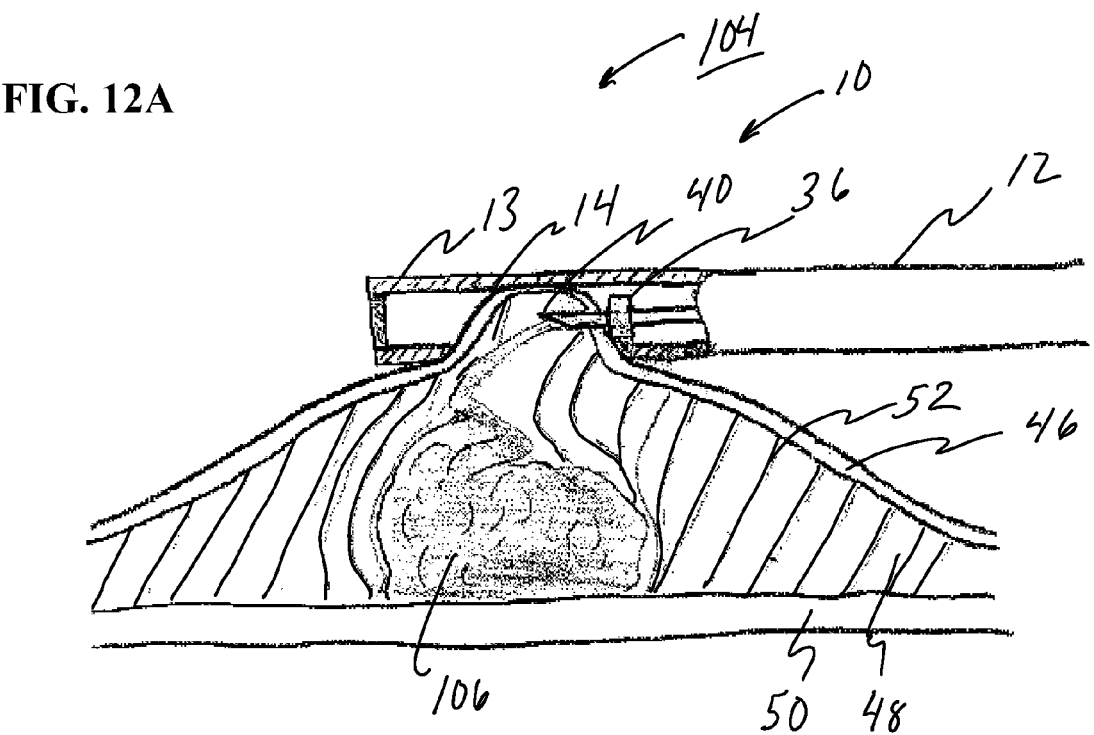
FIGS. 12A and 12B are cross-sectional views showing a method for dissecting a submucosal layer according to another embodiment of the present invention.
Figure 12B:
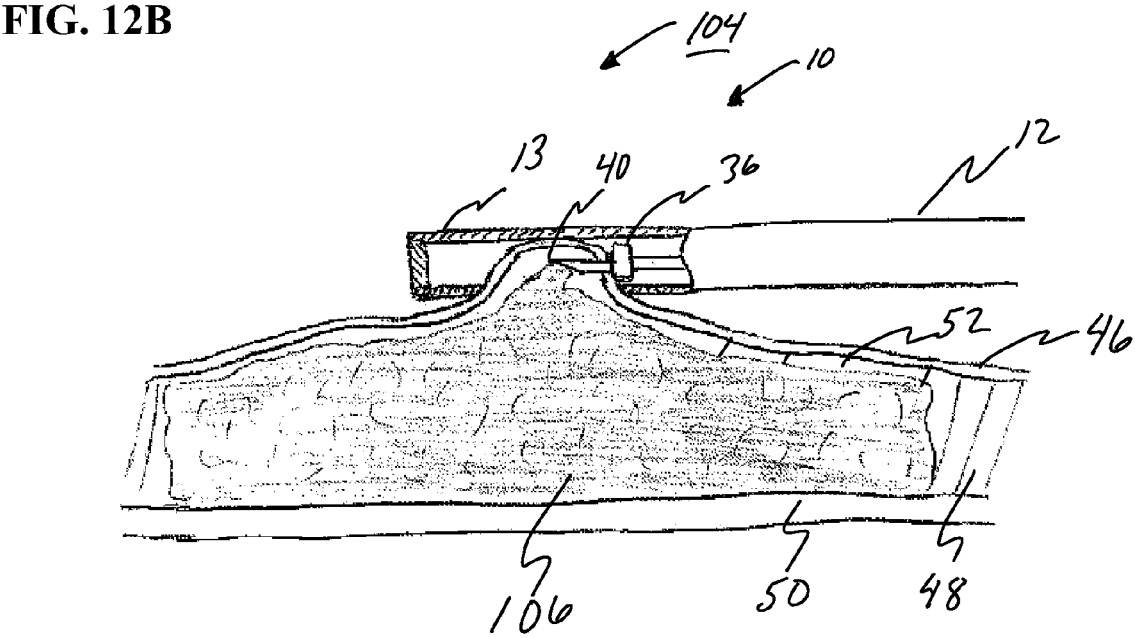

FIGS. 12A and 12B show a safe access dissection system 104 of the present invention that includes a safe access needle injection instrument 10 and an injectable dissection material 106. The injectable dissection material 106 takes the form of a semisolid gelatin capable of mechanically breaking the submucosal connective tissue 52. The semisolid gelatin may be formed using biocompatible commercially available gelatins. Generally, these gelatins are in a powdered form and mixed with warm water. Upon cooling, the gelatin forms a semisolid consistency with physical cross links. The gelatin material is preferably formed within the barrel of a pressurizable syringe since aspiration of this material is difficult. A safe access needle injection instrument 10 is used to create a safety bleb beneath the mucosal layer 46 in the digestive tract of a mammal. Once the safety bleb is formed, the injectable dissection material 106 may be delivered through needle tip 40 into the submucosal layer 48 as shown in FIG. 12A. The mass and semisolid nature of the injectable dissection material 106 begins to apply force to the stretched submucosal connective tissue 52, unlike a saline solution which only permeates the submucosal layer 48. Under the force imparted by the increased volume due to the introduction of the injectable dissection material 106, the submucosal connective tissue 52 breaks, thereby causing the mucosal layer 46 to become detached from muscular layer 50 in bleb region as shown in FIG. 12B. Alternatively, the injectable dissection material 106 may also take the form of injectable solutions which solidify upon entering the submucosal space. Solutions which solidify after injection into the submucosal space may be thermo sensitive polymer solutions such as Pluronic 127. Additional injectable solidifying solutions include monomer and polymer solutions like hydrogels and cyanoacrylates which polymerize or crosslink upon contact with tissue or added chemical agents.

Figure 13A:
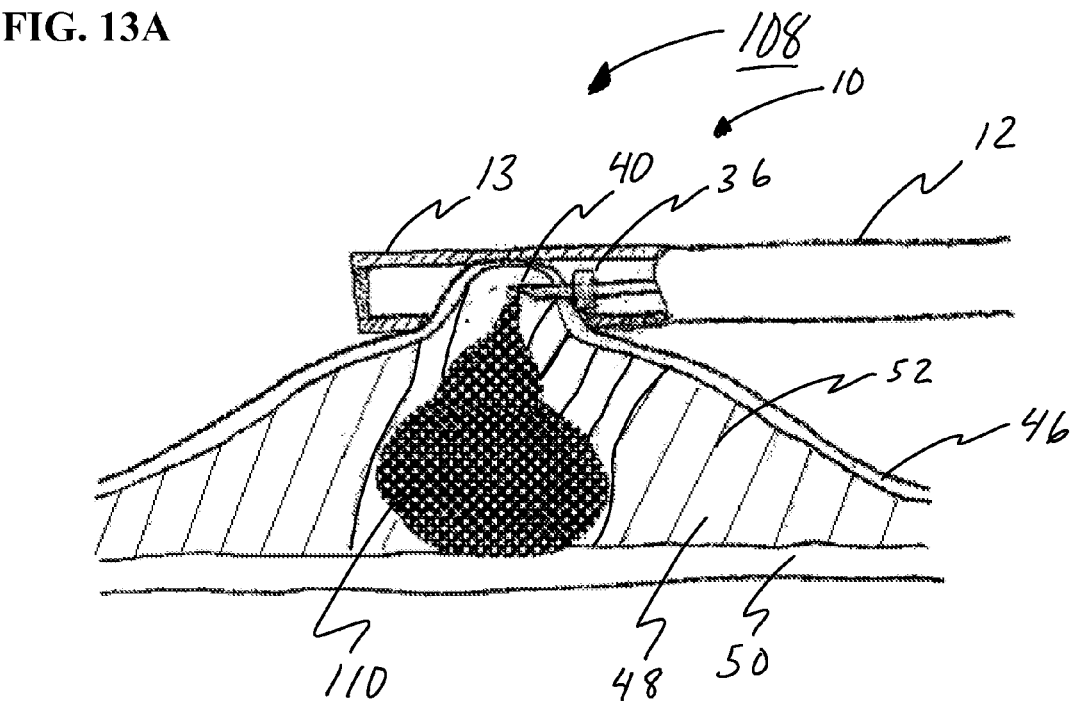
FIGS. 13A and 13B are cross-sectional views showing a method for dissecting a submucosal layer according to yet another embodiment of the present invention.
Figure 13B:
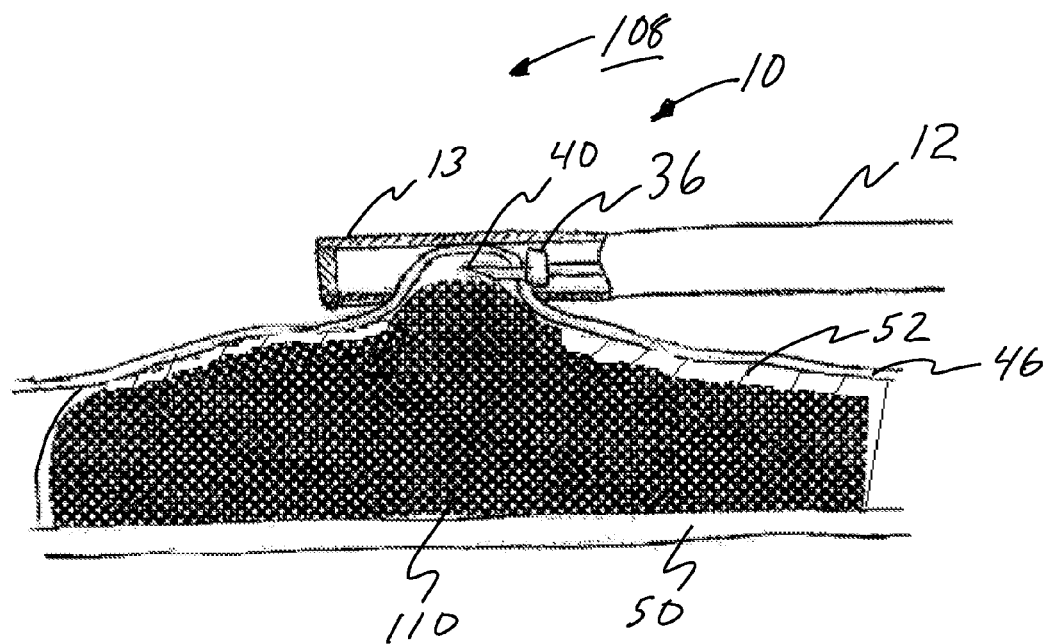

FIGS. 13A and 13B show a safe access dissection system 108 of the present invention that includes a safe access needle injection instrument 10 and an injectable dissection material 110. The injectable dissection material 110 takes the form of gelled microspheres dispersed in a solution capable of mechanically breaking the submucosal connective tissue 52. The microspheres may be formed using biocompatible natural materials such as collagen and alginates or synthetic materials like polyvinylalcohol (PVA), polyvinylpyrolidone (PVP) and acrylate polymers. A safe access needle injection instrument 10 is used to create a safety bleb beneath the mucosal layer 46 in the digestive tract of a mammal. Once the safety bleb is formed, the injectable dissection material 110 may be delivered through needle tip 40 into the submucosal layer 48 as shown in FIG. 13A. The mass and solid nature of the injectable dissection material 110 begins to apply force to the stretched submucosal connective tissue 52, unlike a saline solution which only permeates the submucosal layer 48. Under the force imparted by the increased volume due to the introduction of the injectable dissection material 110, the submucosal connective tissue 52 breaks, thereby causing the mucosal layer 46 to become detached from muscular layer 50 in bleb region as shown in FIG. 13B.

Figure 14:
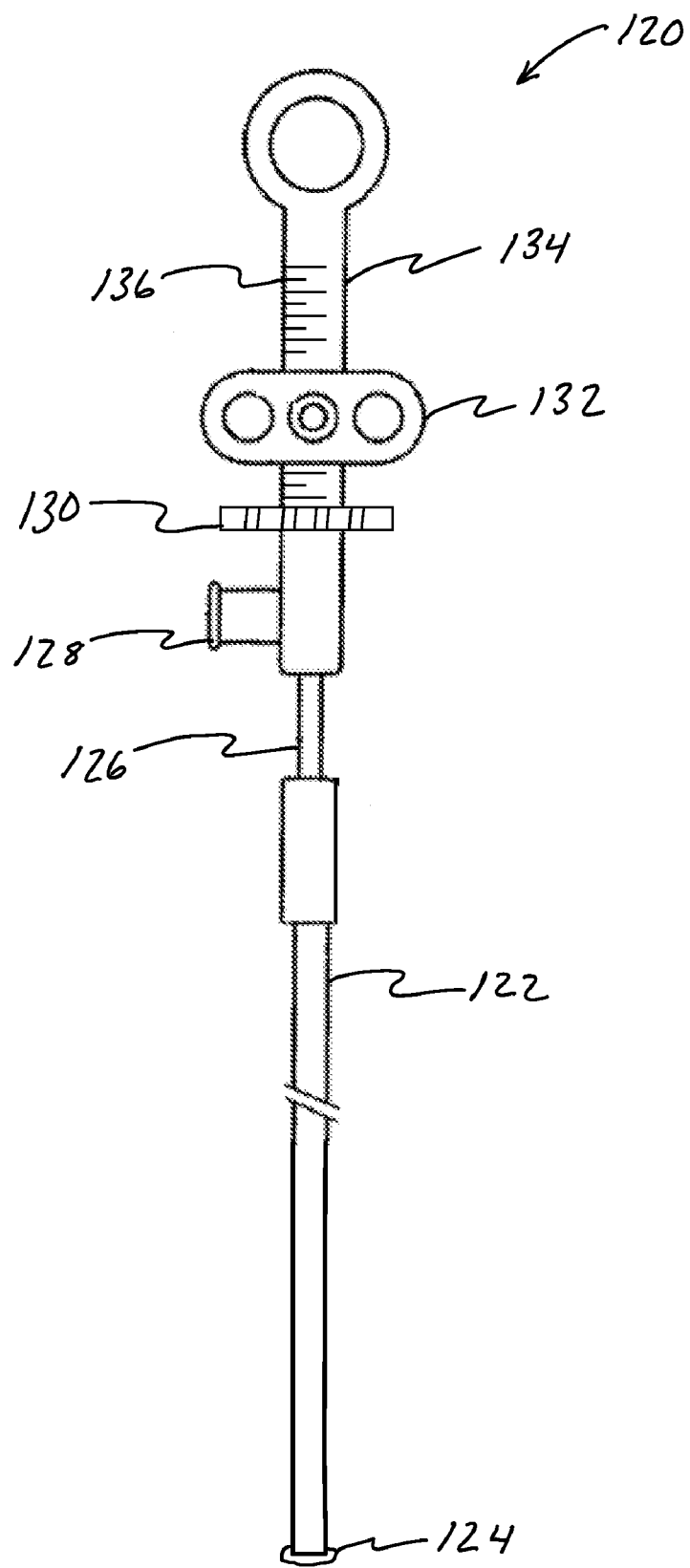
FIG. 14 is a side view showing a submucosal tunneling instrument of a submucosal medical procedure system in accordance with an embodiment of the present invention.

FIG. 14 illustrates a submucosal tunneling instrument 120 for performing a submucosal medical procedure of the present invention. The submucosal tunneling instrument 120 includes a catheter 122 having proximal and distal ends and an expandable member which preferably takes the form of balloon member 124 located adjacent the distal end. The proximal end of catheter 122 is attached to connector tubing 126 to access inflation port 128. Valve assembly 130 provides a seal for fluid introduced into inflation port 128. Tether slide 132 is slidably positioned on handle body 134. Handle body 134 includes distance markers 136 to gauge the movement of tether slide 132.

A cross sectioned view of the distal end of the submucosal tunneling instrument 120 is shown in more detail in FIG. 15A.

Catheter 122 has a distal end 138 and a lumen 123. Located within lumen 123 is balloon member 124. The balloon member 124 is preferably non-compliant of the type generally known in the art, however, balloon member 124 may be of the compliant or semi-compliant type. The balloon member 124 may be formed from biocompatible polymer types such as olefins, elastomers, thermoplastic elastomers, vinyls, polyamides, polyimides, polyesters, fluropolymers, copolymers and blends of any of the aforementioned. The proximal end 140 of balloon member 124 is attached to the distal end 138 of catheter 122. The distal end 142 of balloon member 124 is positioned within the lumen 123 in an everted configuration. A tether member 144 is connected to the distal end 142 of balloon member 124. Tether member 144 is flexible and preferably takes the form of a filament, as shown, however tether member 144 may take the form of a tube. The proximal end of tether member 144 is connected to tether slide 132 through valve assembly 130. Tether member 144 aids in initially positioning balloon member 124 within the lumen 123 of catheter 122. While the aforementioned embodiment of the submucosal tunneling instrument include an expandable member which preferably takes the form of an inflatable balloon, other devices may be suitable for essentially performing the same function. For instance as depicted in an alternate embodiment shown in FIG. 15B, the expandable member 124 may take the form of an expandable elongate braid, mesh or tubular framework in which the proximal end of the expandable member is connected to the distal end of the catheter and the distal end of the expandable member is everted and positioned within the lumen of the catheter. A stiffened tether member 144 located within the lumen of the catheter 122 may be used as a pusher to push the expandable elongate member from the lumen of the catheter in essentially the same way that the balloon expands from the lumen of the catheter. The expandable elongate braid may be formed from resilient materials such as nitinol, spring steels, vitreloy, as well as polymers and composites. The expandable member may take comprise individual wires to form a braid or mesh configuration. Alternatively the expandable member may be laser cut from a tube forming a tubular framework. Preferably the expanded diameter is larger than the outer diameter of the catheter.

Figure 16A:
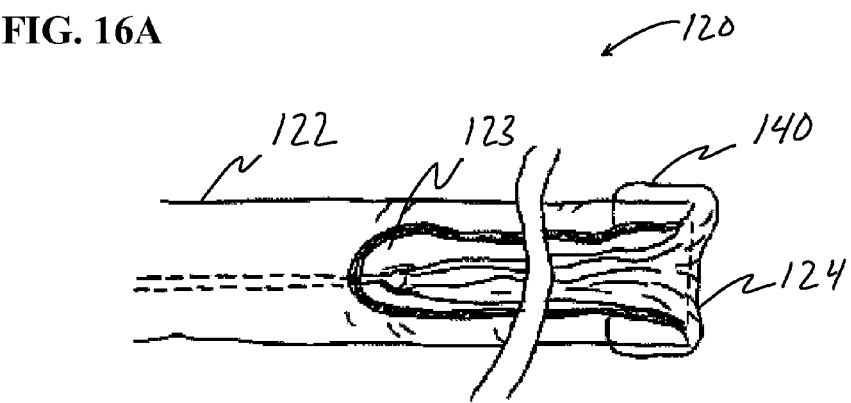
FIGS. 16A through 16C are partial cross-sectional views showing a sequence of expanding the distal end of a submucosal tunneling instrument of a submucosal medical procedure system in accordance with an embodiment of the present invention.
Figure 16B:
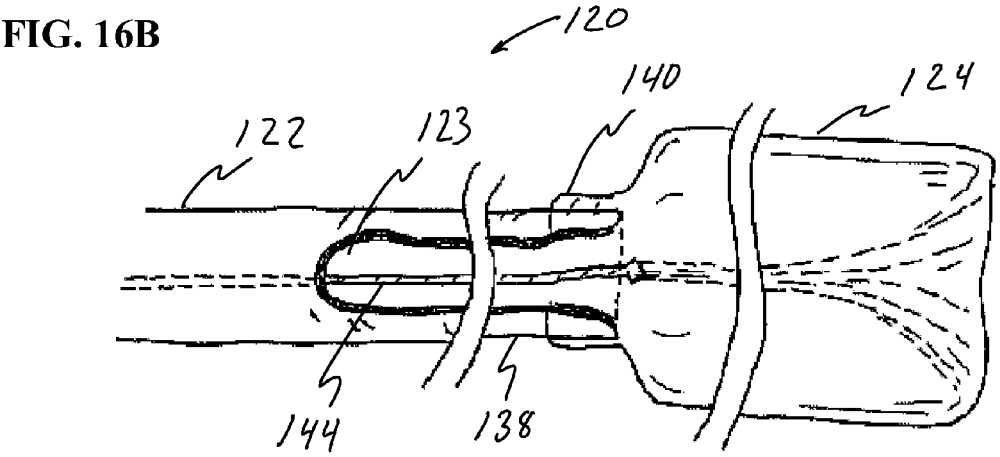
Figure 16C:
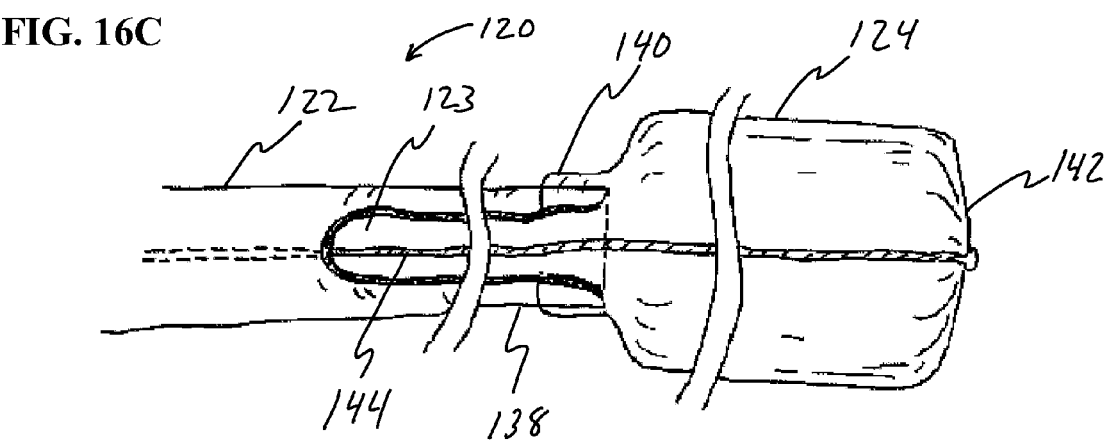

FIGS. 16A through 16C illustrate various stages of deployment of balloon member 124 from the lumen 123 of catheter 122. To deploy balloon member 124 a fluid filled syringe or other source is connected to inflation port 128. As pressurized fluid enters the lumen 123 of catheter 122, the proximal end of balloon member 124 exits the lumen expands. Balloon member 124 has an expanded diameter range of about 1 mm to about 30 mm and is preferably in the range of 2 mm to 20 mm. The length of balloon member 124 is a long as necessary to perform a desired submucosal medical procedure. This length can be in the range of 5 mm to 50 cm and preferably in the range of 7 mm to about 10 cm. As balloon member 124 expands it extends in a linear fashion moving the distal end 142 of balloon member 124 towards the distal end 138 of catheter 122. As long as pressurized fluid is applied to catheter lumen 123, balloon 124 will extend to its full length. Alternatively, since the distal end 142 of balloon 124 is connected to tether member 144, the amount of linear extension balloon 124 takes may be controlled by the tether slide 132 to define an extension length shorter than the full length of the balloon.

Figure 17:
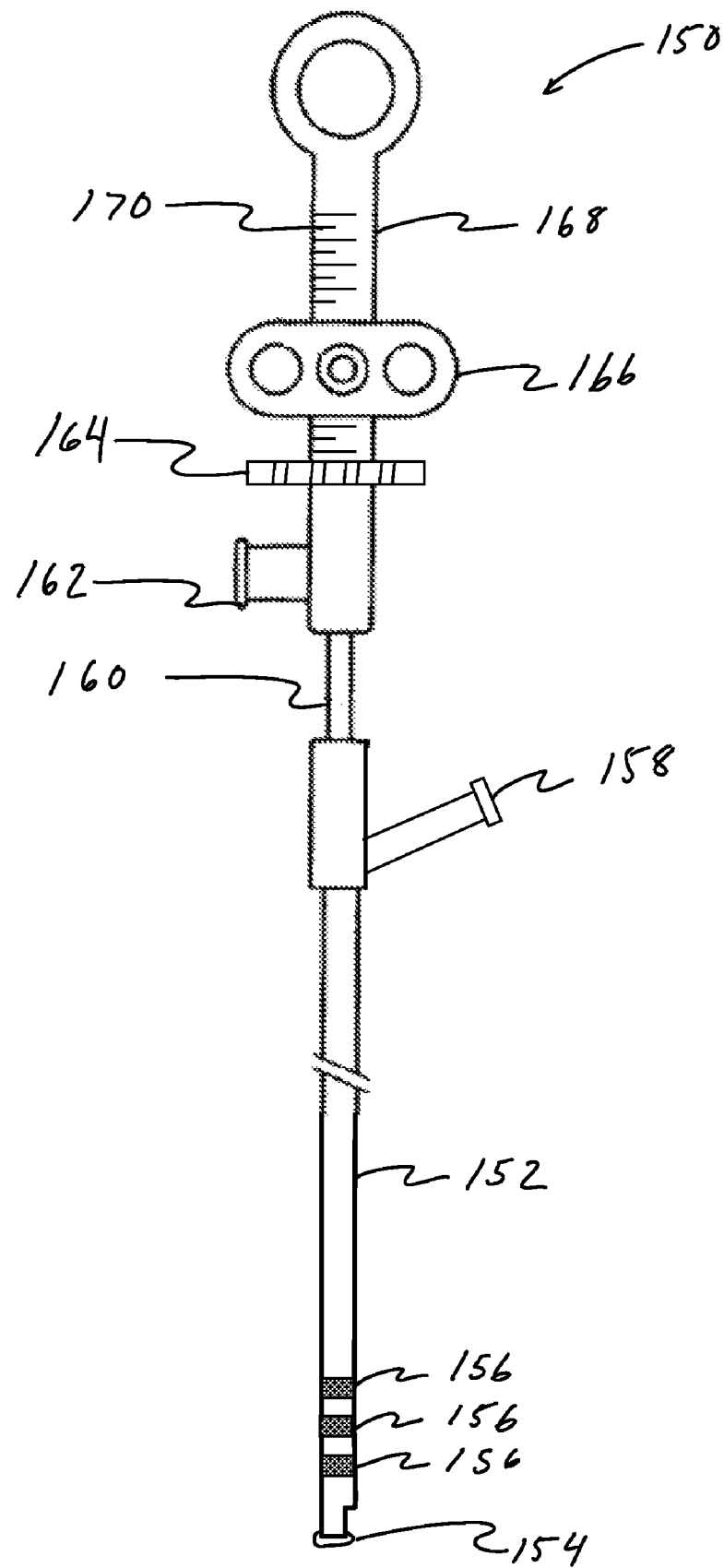
FIG. 17 is a side view showing a variation of a submucosal tunneling instrument of a submucosal medical procedure system in accordance with an embodiment of the present invention.

FIG. 17 illustrates a submucosal tunneling instrument 150 for performing a submucosal medical procedure of the present invention. The submucosal tunneling instrument 150 includes a catheter 152 having proximal and distal ends and a balloon member 154 located adjacent the distal end. Positioned on the exterior of catheter 152 adjacent the distal end is a series of markers 156. These markers may be visible under direct visualization of the endoscope and may be additionally visible under fluoroscopy. Adjacent the proximal end of catheter 152 is an auxiliary device port 158. The proximal end of catheter 152 is attached to connector tubing 160 to access inflation port 162. Valve assembly 164 provides a seal for fluid introduced into inflation port 162. Tether slide 166 is slidably positioned on handle body 168. Handle body 168 includes distance markers 170 to gauge the movement of tether slide 166.

Figure 18:
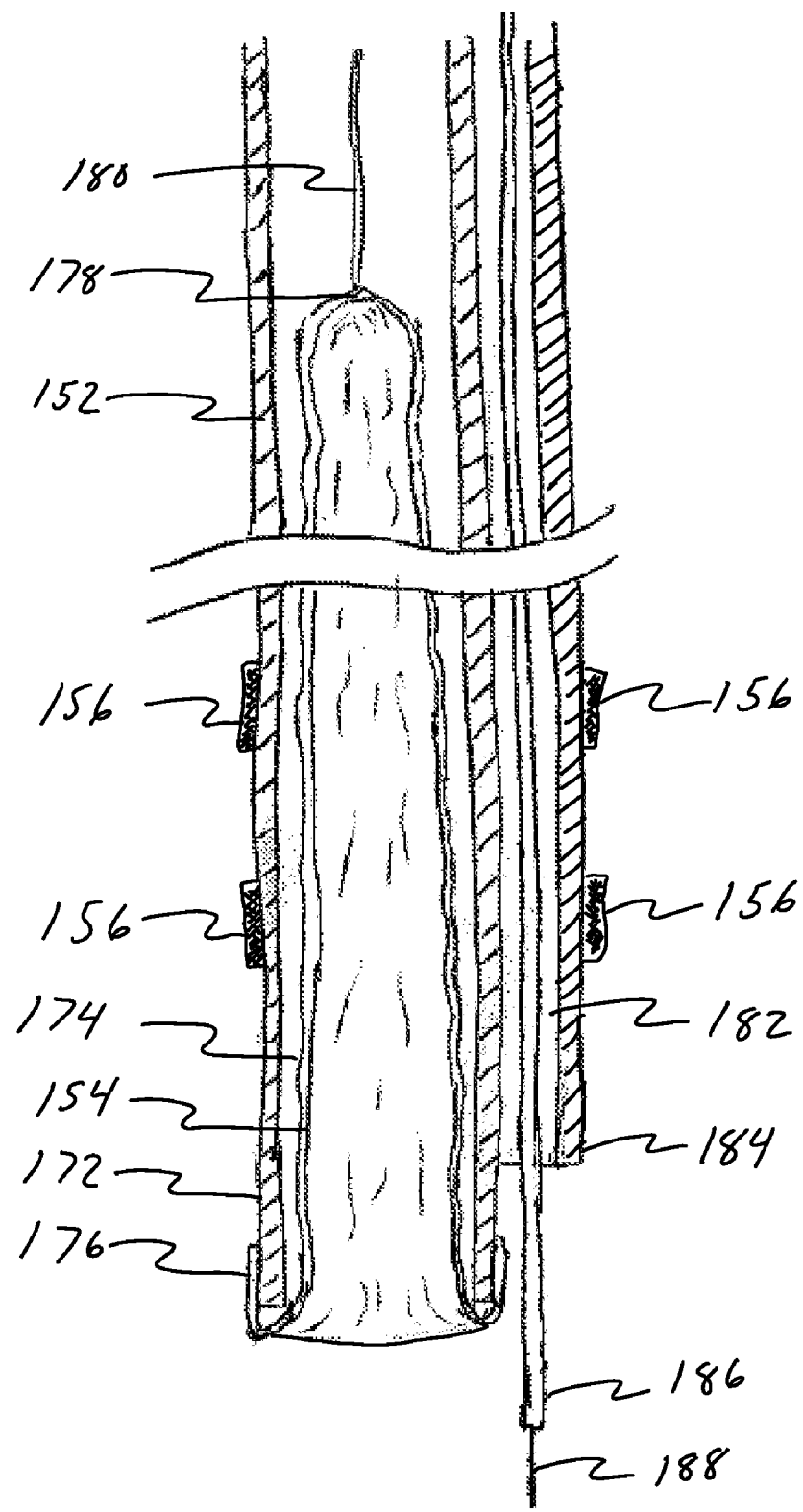
FIG. 18 is a cross-sectional view showing a sequence of expanding the distal end of another variation a submucosal tunneling instrument of a submucosal medical procedure system in accordance with an embodiment of the present invention.

A cross sectioned view of the distal end of the submucosal tunneling instrument 150 is shown in more detail in FIG. 18. Catheter 152 has a distal end 172 and a first lumen 174. Located within first lumen 174 is balloon member 154. The balloon member 154 is preferably non-compliant of the type generally known in the art, however, balloon member 154 may be of the compliant or semi-compliant type. The balloon member 154 may be formed from biocompatible polymer types such as olefins, elastomers, thermoplastic elastomers, vinyls, polyamides, polyimides, polyesters, fluropolymers, copolymers and blends of any of the aforementioned. The proximal end 176 of balloon member 154 is attached to the distal end 172 of catheter 152. The distal end 178 of balloon member 154 is positioned within the first lumen 174 in an everted configuration. A tether member 180 is connected to the distal end 178 of balloon member 154. Tether member 180 is flexible and preferably takes the form of a filament, as shown, however tether member 180 may take the form of a tube. The proximal end of tether member 180 is connected to tether slide 166 through valve assembly 164. Tether member 180 aids in initially positioning balloon member 154 within the first lumen 174 of catheter 152. Catheter 152 has a second lumen 182 that extends from auxiliary device port 158 to distal end 184. Distal end 184 is located proximal to distal end 172 of catheter 152. Slidably disposed within second lumen 182 is a needle knife 184 that has a knife tip 188. Needle knife 184 is preferably of the endoscopic electrosurgical type however any form of incision device that may be operated to form an incision in tissue such as mechanical cutters, water jets or lasers may be suitable.

Figure 19A:
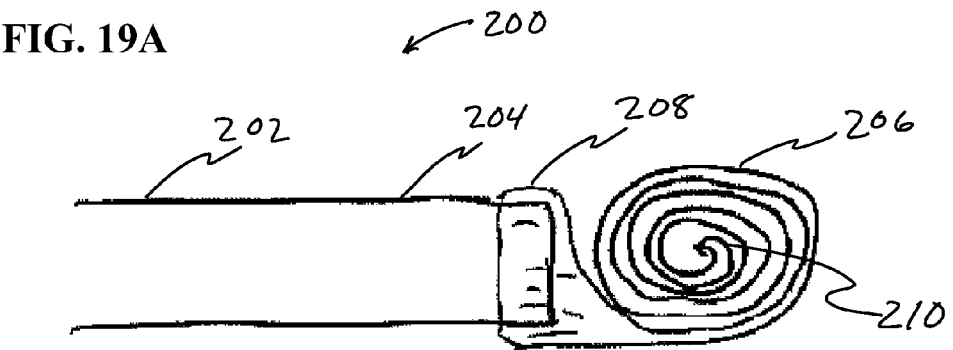
FIGS. 19A through 19C are a side views showing another variation of a submucosal tunneling instrument of a submucosal medical procedure system in accordance with an embodiment of the present invention.
Figure 19B:
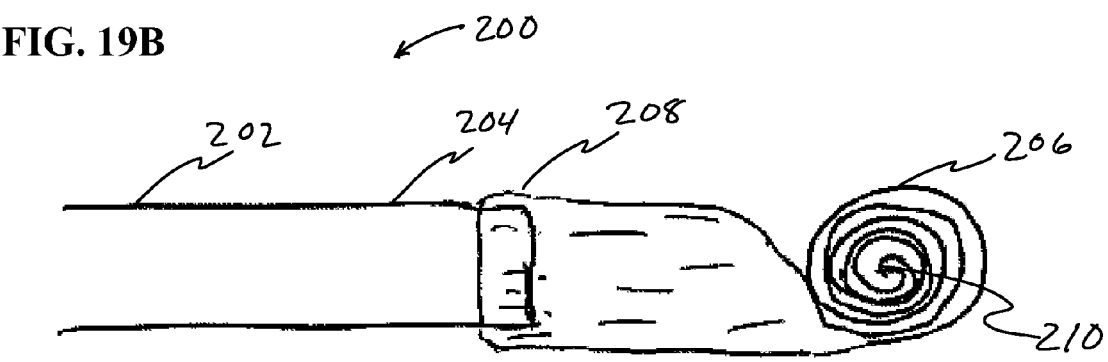
Figure 19C:
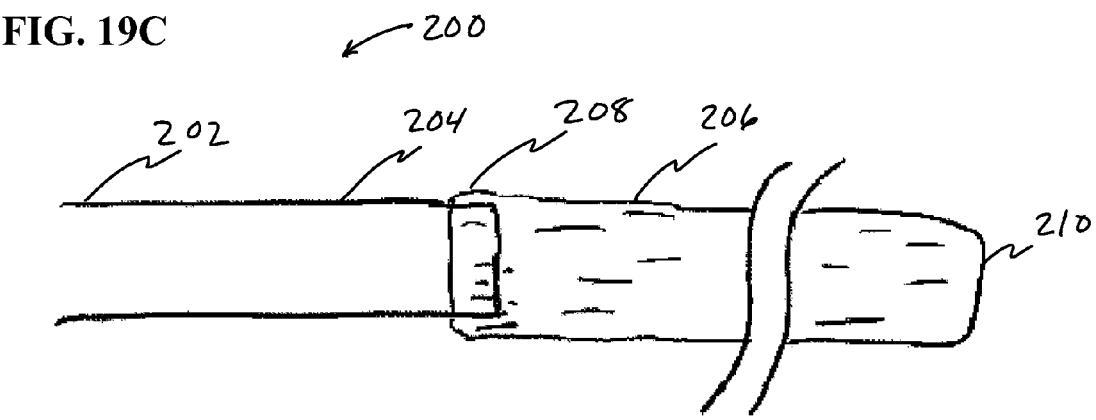
Figure 20A:
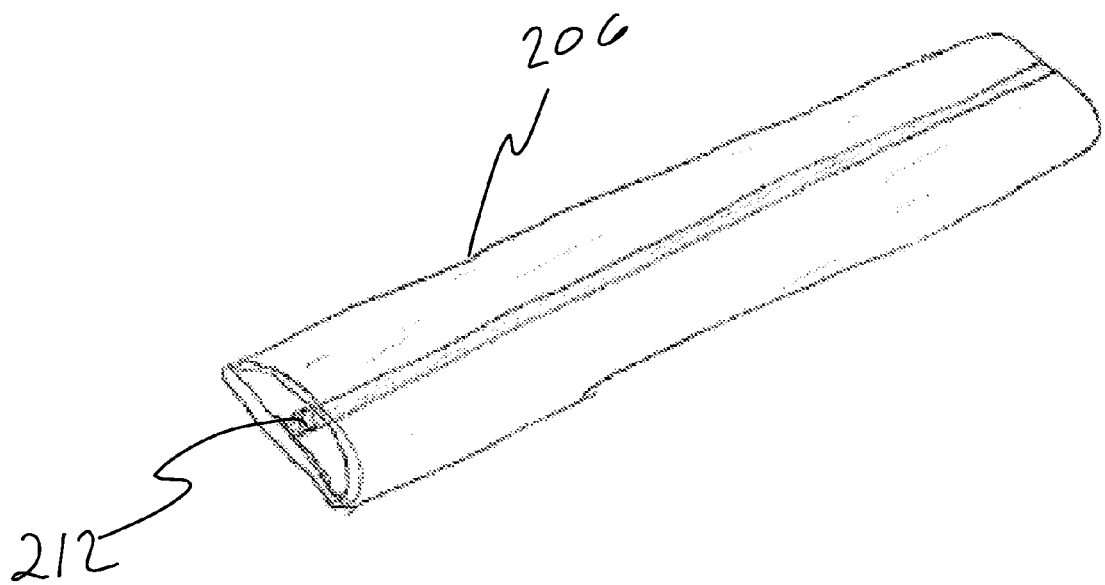
FIGS. 20A and 20B are perspective views showing a variation of the distal end of a submucosal tunneling instrument of a submucosal medical procedure system in accordance with an embodiment of the present invention.
Figure 20B:
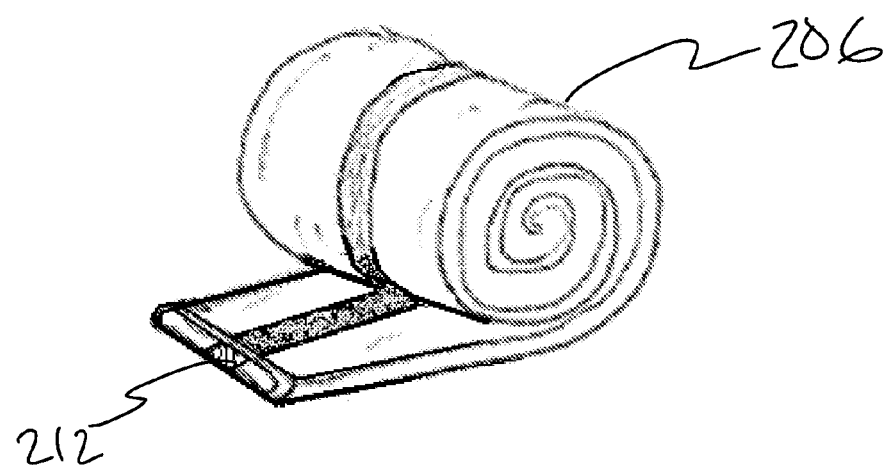

FIGS. 19A through 19C illustrate a submucosal tunneling instrument 200, according to another embodiment of the present invention. Catheter 202 has a distal end 204 which is connected to balloon member 206. The proximal end 208 of balloon 206 is connected to distal end 204 of catheter 202. Balloon member 206 is rolled into a spiral configuration in which the distal end 210 is located in the center of the spiral. As the lumen of catheter 202 which is connected to balloon member 206 is pressurized, balloon member 206 inflates. The inflation of balloon member 206 causes the balloon to unroll from a spiral configuration extending linearly. The balloon member 206 may be thermally treated to retain the spiral configuration for delivery through the working channel of an endoscope. Alternatively the balloon member 206 may incorporate a spiral shaped member 212 attached the wall of balloon member 206 as shown in FIGS. 20A and 20B. The spiral shaped member may be formed from a resilient filament as shown in an outstretched configuration in FIG. 20A. The spiral shaped member being formed of a resilient filament and incorporated into the wall of the balloon preferably takes its spiral shape and in doing so forms the balloon member into a spiral shape as shown in FIG. 20B.

Figure 21A:
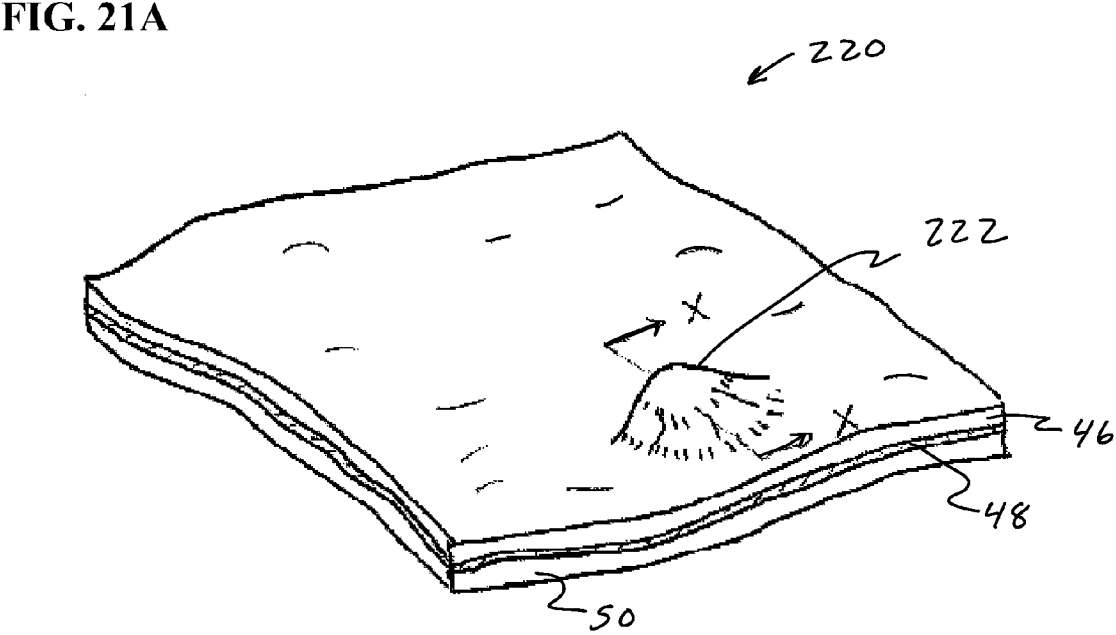
FIGS. 21A and 21B are perspective and cross sectional views of an area of tissue in the digestive tract having a submucosal saline bleb in accordance with an embodiment of the present invention.
Figure 21B:
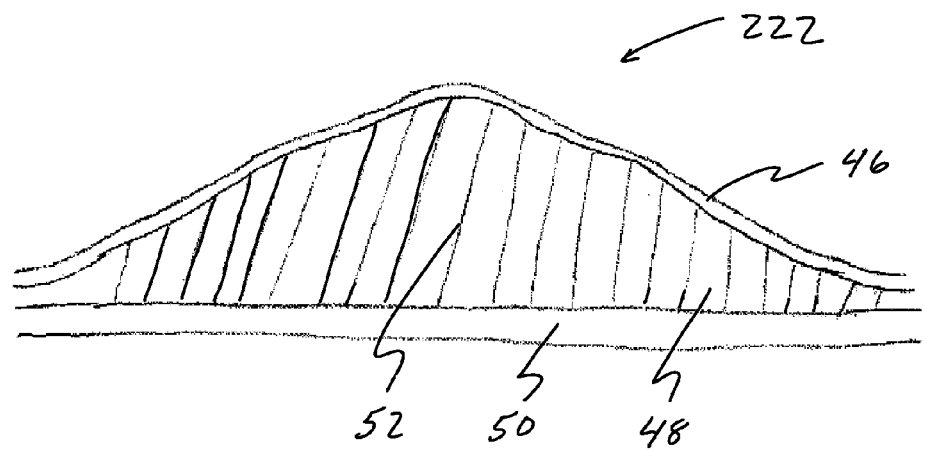
Figure 22A:
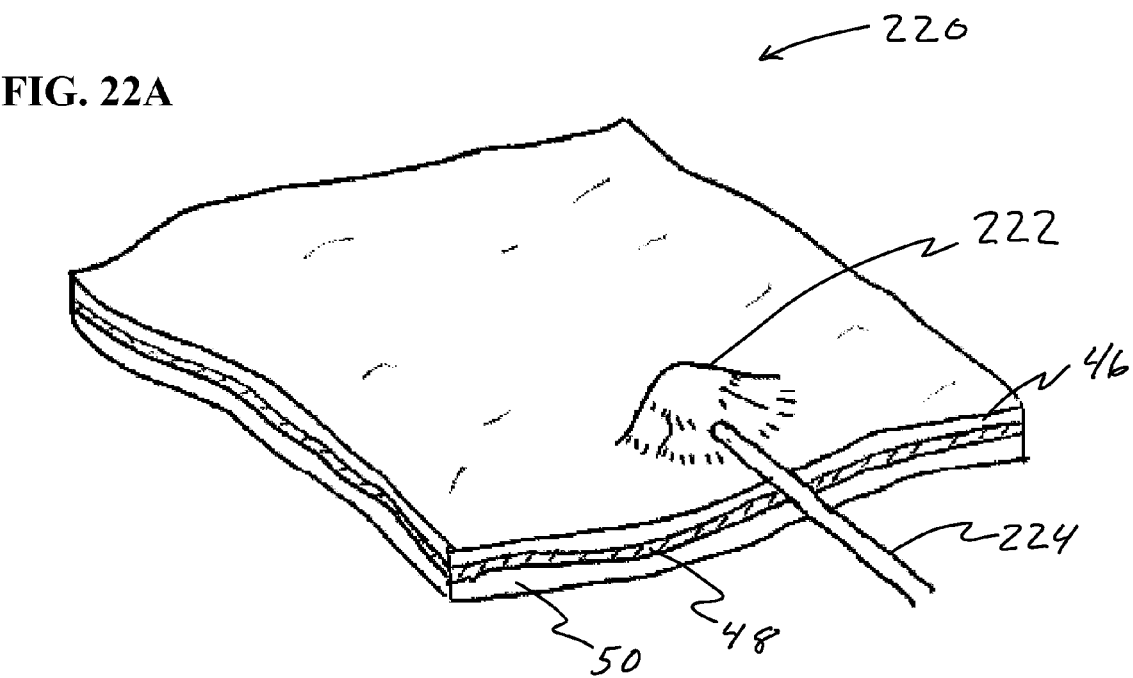
FIGS. 22A and 22B are perspective and cross sectional views of an area of tissue in the digestive tract having a submucosal saline bleb in which an opening through the mucosal layer is made in accordance with an embodiment of the present invention.
Figure 22B:
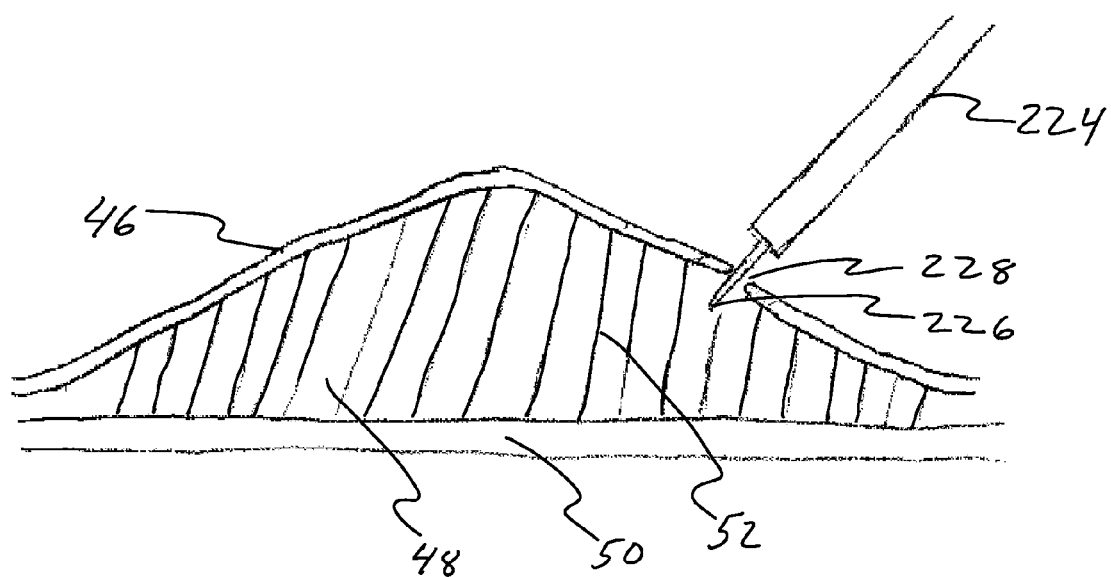
Figure 23A:
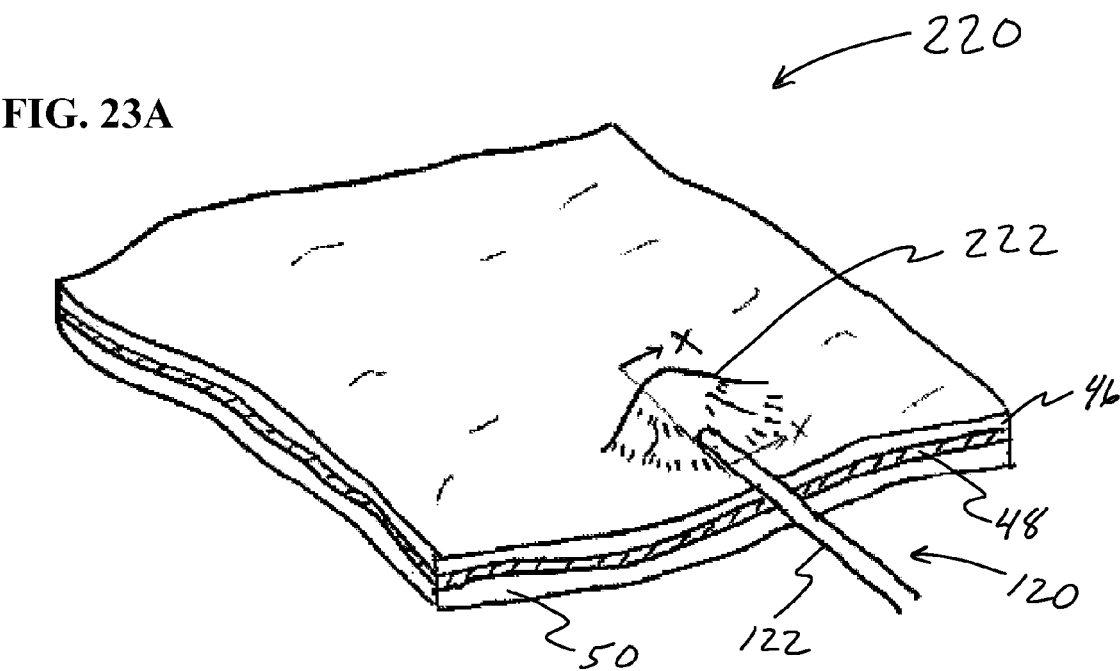
FIGS. 23A through 23D are perspective and cross sectional views showing a method of forming a submucosal tunnel using a submucosal tunneling instrument according to an embodiment of a submucosal medical procedure system of the present invention.
Figure 23B:
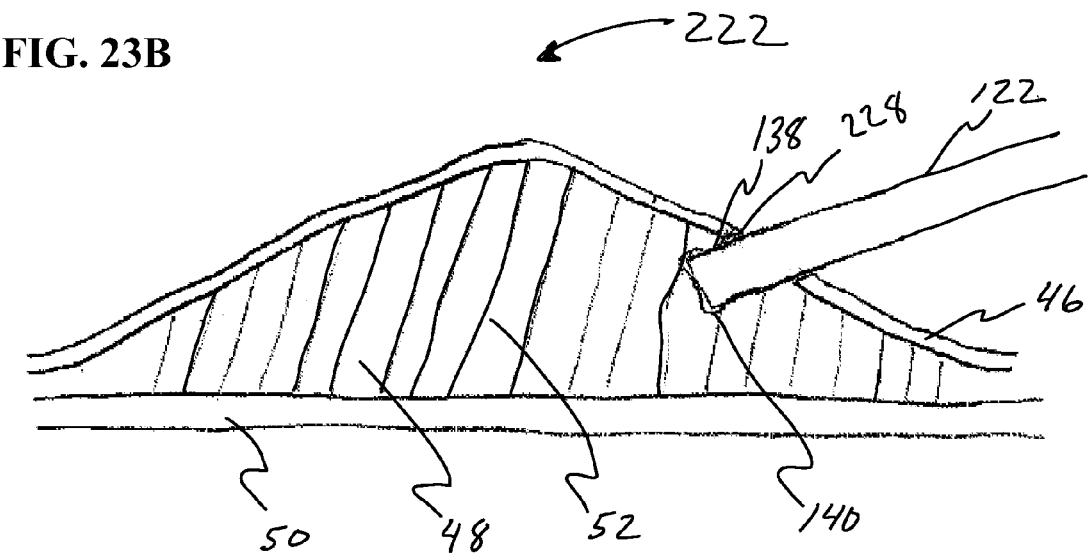
Figure 23C:
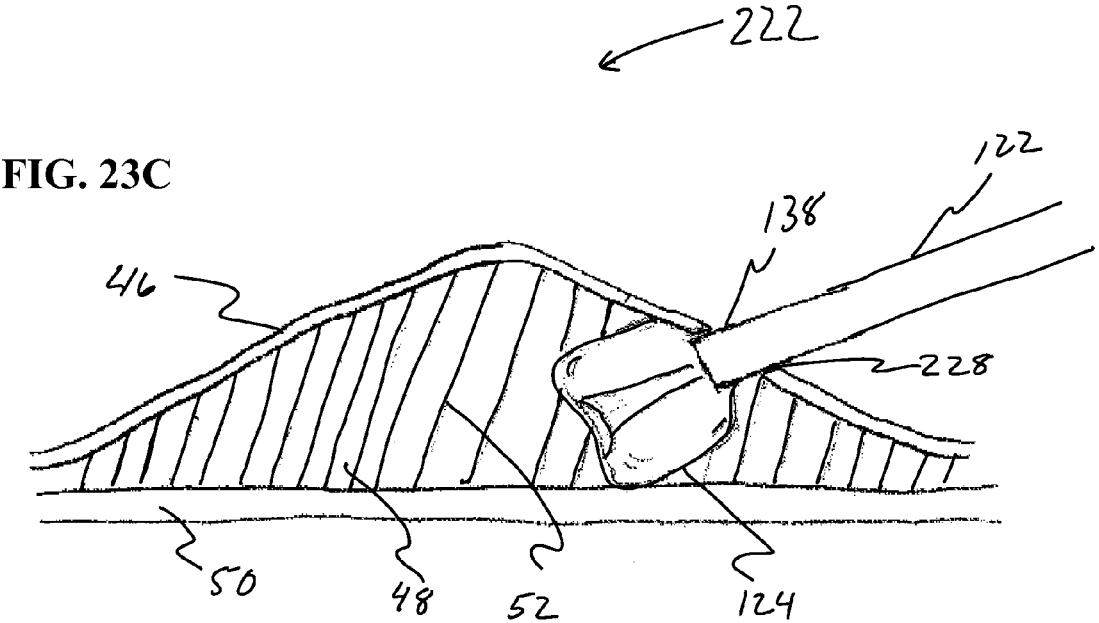
Figure 23D:
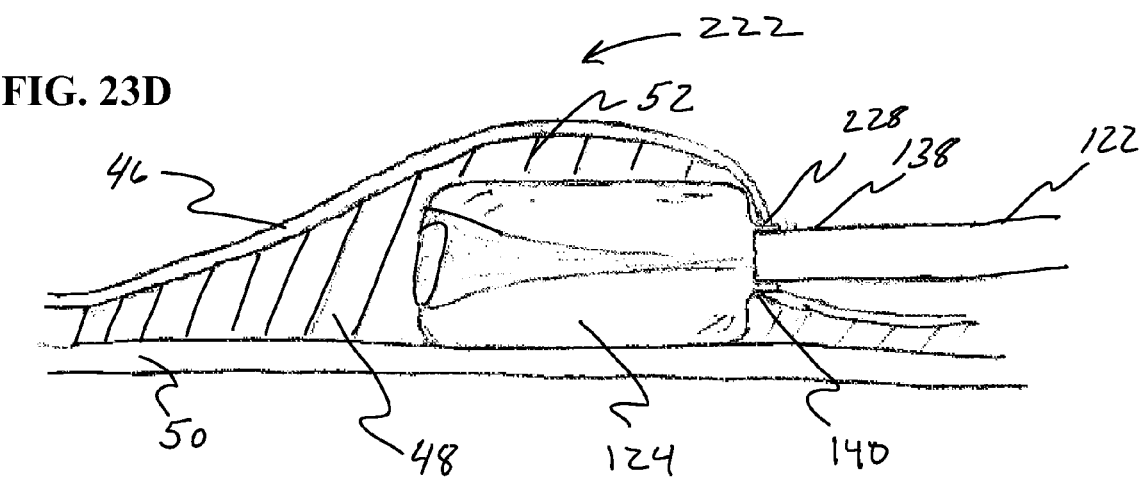
Figure 24A:
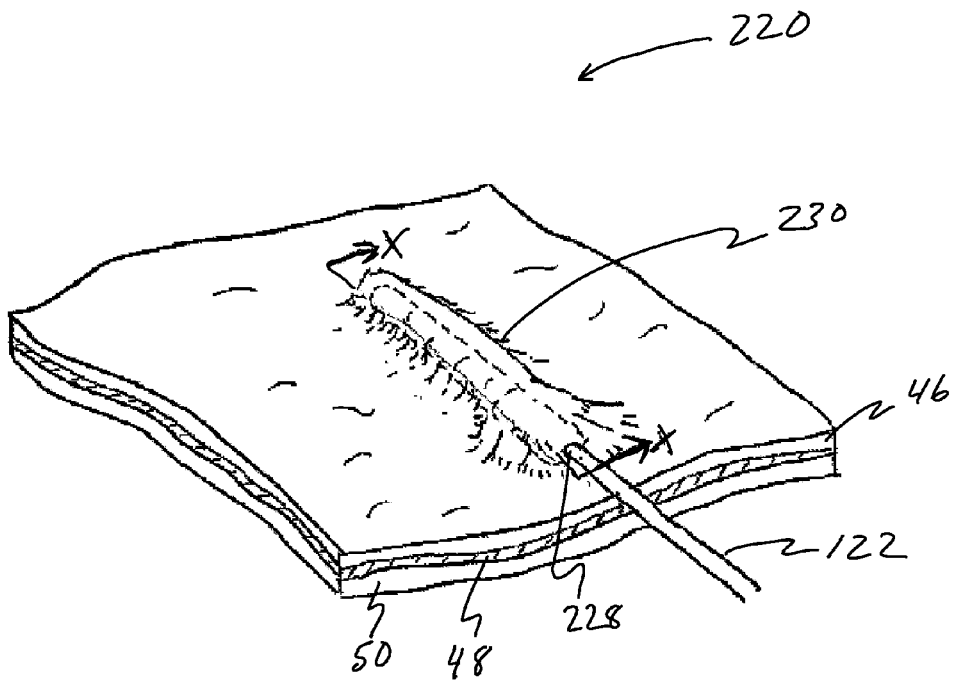
FIGS. 24A through 24D are perspective and cross sectional views showing a method of using a submucosal tunneling instrument according to an embodiment of a submucosal medical procedure system of the present invention.
Figure 24B:
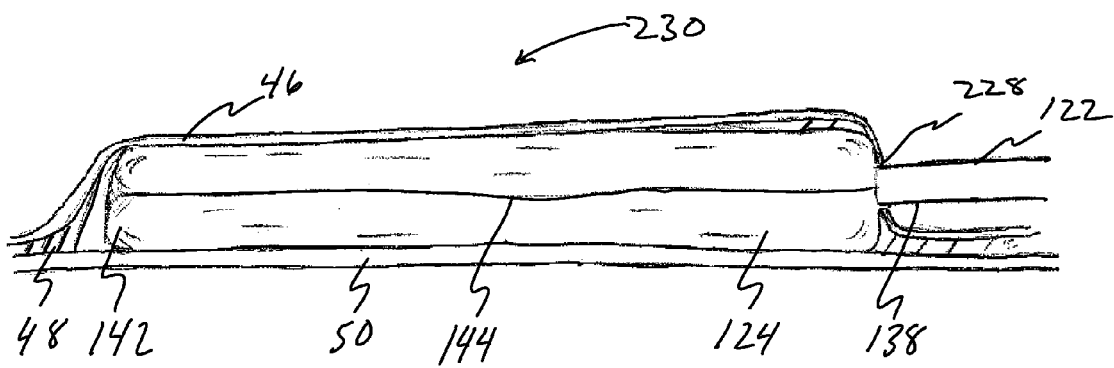
Figure 24C:
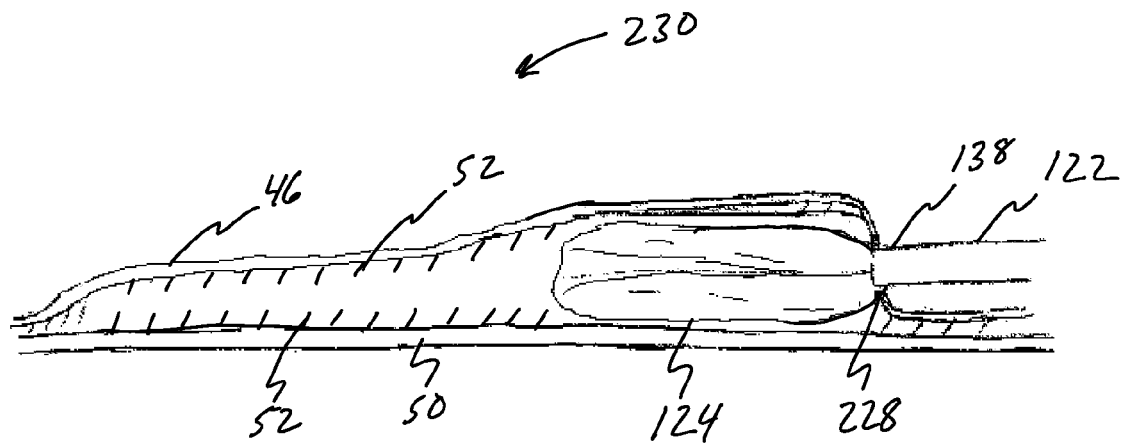
Figure 24D:
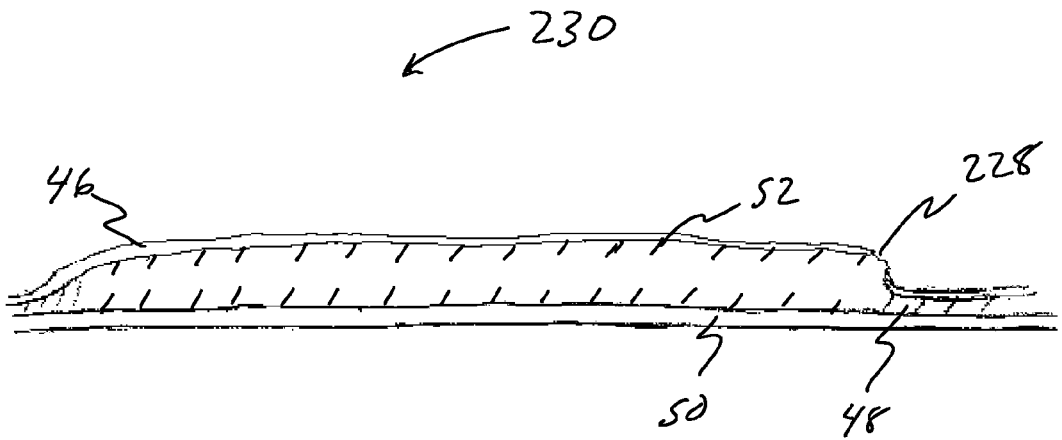

In order to perform a submucosal medical procedure, the target area in the digestive tract must be prepared to gain access to the submucosal space. FIGS. 21A and 21B illustrate a desired region 220 of the digestive tract of a mammal. A safe access needle injection instrument according to any of the embodiments previously described may be used to form a safety bleb 222 beneath the mucosal layer 46. The safety bleb contains the submucosal connective tissue 52 generally in a stretched condition attached to both the mucosal layer 46 and the muscular layer 50. As shown in FIGS. 22A and 22B, an endoscopic incision tool 224 is positioned adjacent to the safety bleb 222. An incision tool tip 226 of the endoscopic incision tool 224 is used to create a small mucosal opening 228 in the mucosal layer 46 of the safety bleb. The elevated mucosal layer 46 reduces the likelihood that the incision tool tip 226 will damage the underlying muscular layer 50. FIGS. 23A through 24D illustrate the introduction and operation of a submucosal tunneling instrument into submucosal layer 48. The distal end 138 of the submucosal tunneling instrument 120 is positioned through the mucosal opening 228. Once the proximal end 140 of balloon 124 is through the mucosal opening 228 the submucosal tunneling instrument 120 may be operated. By delivering pressurized fluid through the lumen of catheter 122, the proximal end 140 of balloon 124 inflates to its expanded diameter as depicted in FIG. 23C. Generally the expanded diameter of the proximal end 140 of balloon 124 is larger than the diameter of the mucosal opening 228. The larger diameter prevents balloon 124 from pushing the distal end 138 of catheter 122 backwards out of the submucosal layer 48 through mucosal opening 228. As shown in FIG. 23D, further inflation extends balloon 124 in a linear fashion within the submucosal layer 48 causing the submucosal connective tissue 52 to break in regions adjacent to the balloon. The balloon 124 can only expand by increasing the volume of the surrounding area between the mucosal layer 46 and the muscular layer 50. The application of force during expansion of balloon 124 is concentrated on the submucosal connective tissue 52, thereby causing the submucosal connective tissue 52 to break, whereas the force applied to the mucosal layer 46 or the muscular layer 50 by balloon 124 is diluted over a larger portion of balloon 124. The force required to break the submucosal connective tissue 52 as applied by balloon 124 is less than the force required to perforate the mucosal layer 46 or muscular layer 50 by balloon 124 thereby minimizing trauma to surrounding tissue. FIG. 24A illustrates a perspective view of region 220 in the digestive tract having a submucosal tunnel 230 formed by submucosal tunneling instrument 120. As shown in FIG. 24B, balloon 124 is fully expanded and generally occupies the majority of the space of submucosal tunnel 230. Balloon 124 is then deflated by applying a negative pressure to catheter 122 and retracting tether member 144. The distal end 138 of catheter 122 is then removed from mucosal opening 228, leaving submucosal tunnel 230 generally deflated. The submucosal connective tissue 52 within the tunnel is broken. For some submucosal medical procedures the submucosal tunnel 230 may provide suitable access to the muscular wall or the placement of an implant device. However to perform other submucosal medical procedures an area larger than the submucosal tunnel 230 may be desired.

Figure 25A:
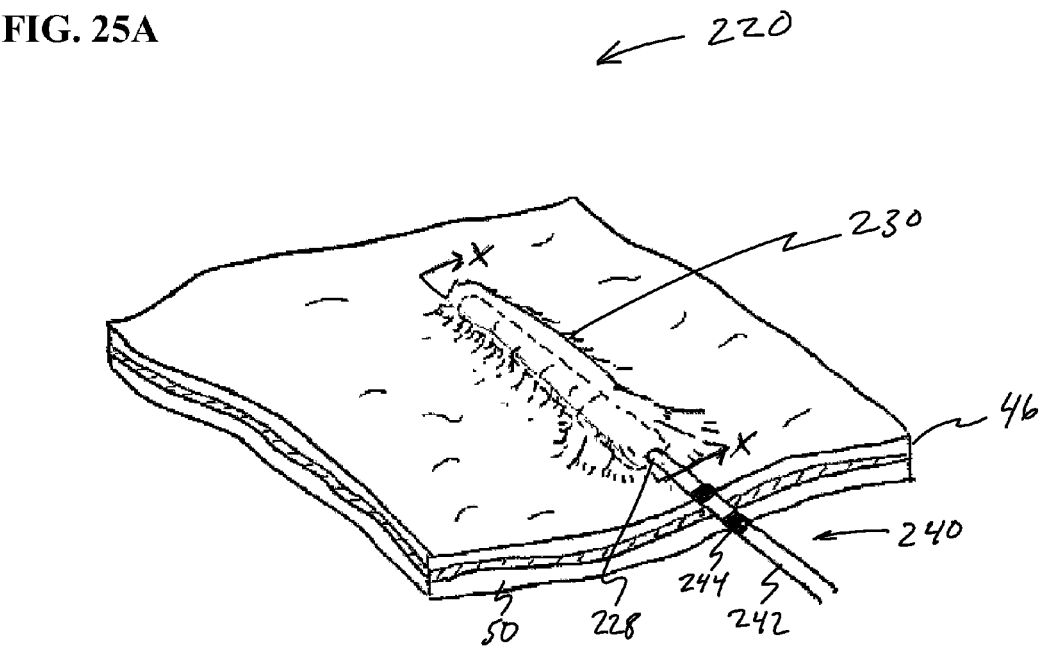
FIGS. 25A through 25D are perspective and cross sectional views showing a method of using a submucosal dissection instrument in a submucosal tunnel according to an embodiment of a submucosal medical procedure system of the present invention.
Figure 25B:
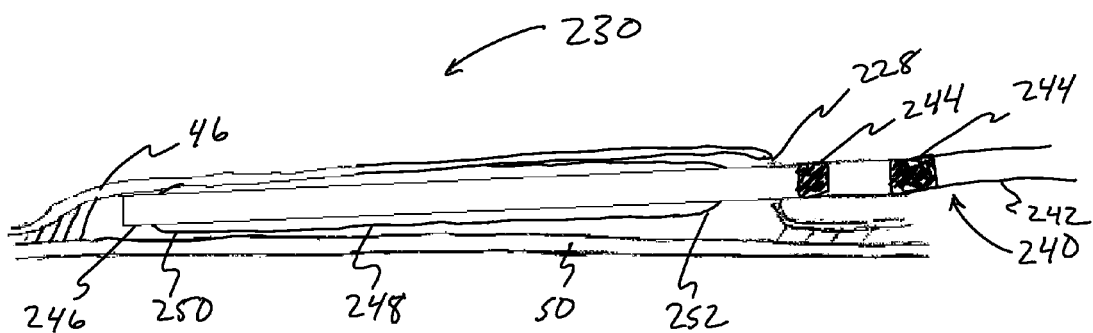
Figure 25C:
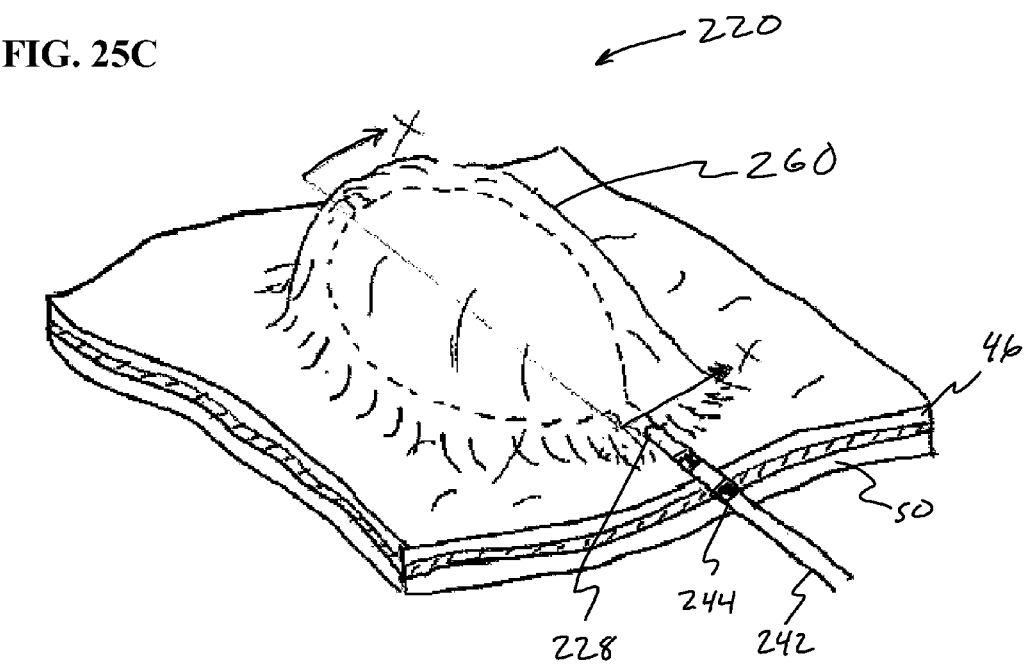
Figure 25D:
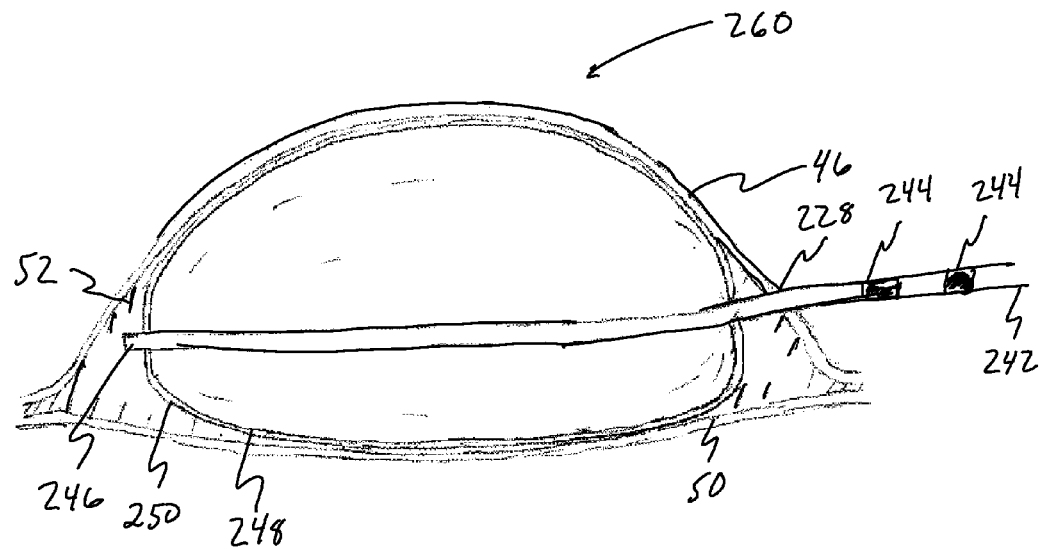

FIGS. 25A through 25D illustrate the formation of an area larger than a submucosal tunnel for performing a submucosal medical procedure according to an embodiment of the present invention. A region 220 in the digestive tract is prepared by forming a submucosal tunnel 230. A submucosal dissection instrument 240 having a catheter 242 is positioned through mucosal opening 228 into submucosal tunnel 230. Located on catheter 242 are markers 244 that indicate the insertion depth of catheter distal end 246 within submucosal tunnel 230. The submucosal dissection instrument 240 is in a proper position for operation when balloon member 248 including distal end 250 and proximal end 252 are sufficiently located within submucosal tunnel 230, as shown in FIG. 25B. As pressurized fluid is applied to a lumen in catheter 242 that is in fluid communication with balloon member 248, balloon member 248 inflates. During the expansion of balloon member 248, the submucosal connective tissue 52 is broken in the area of the expanded balloon member 248 and the mucosal layer 46 is elevated. The elevated mucosal layer 46 forms a large mucosal dissected area 260. After full expansion the balloon member 248 may be deflated and submucosal dissecting instrument 240 removed from the large mucosal dissected area 260. The dissected region beneath mucosal layer 46 has transformed in geometry from a high aspect ratio tunnel to a low aspect ratio chamber suitable for performing some submucosal medical procedures.

Figure 26:
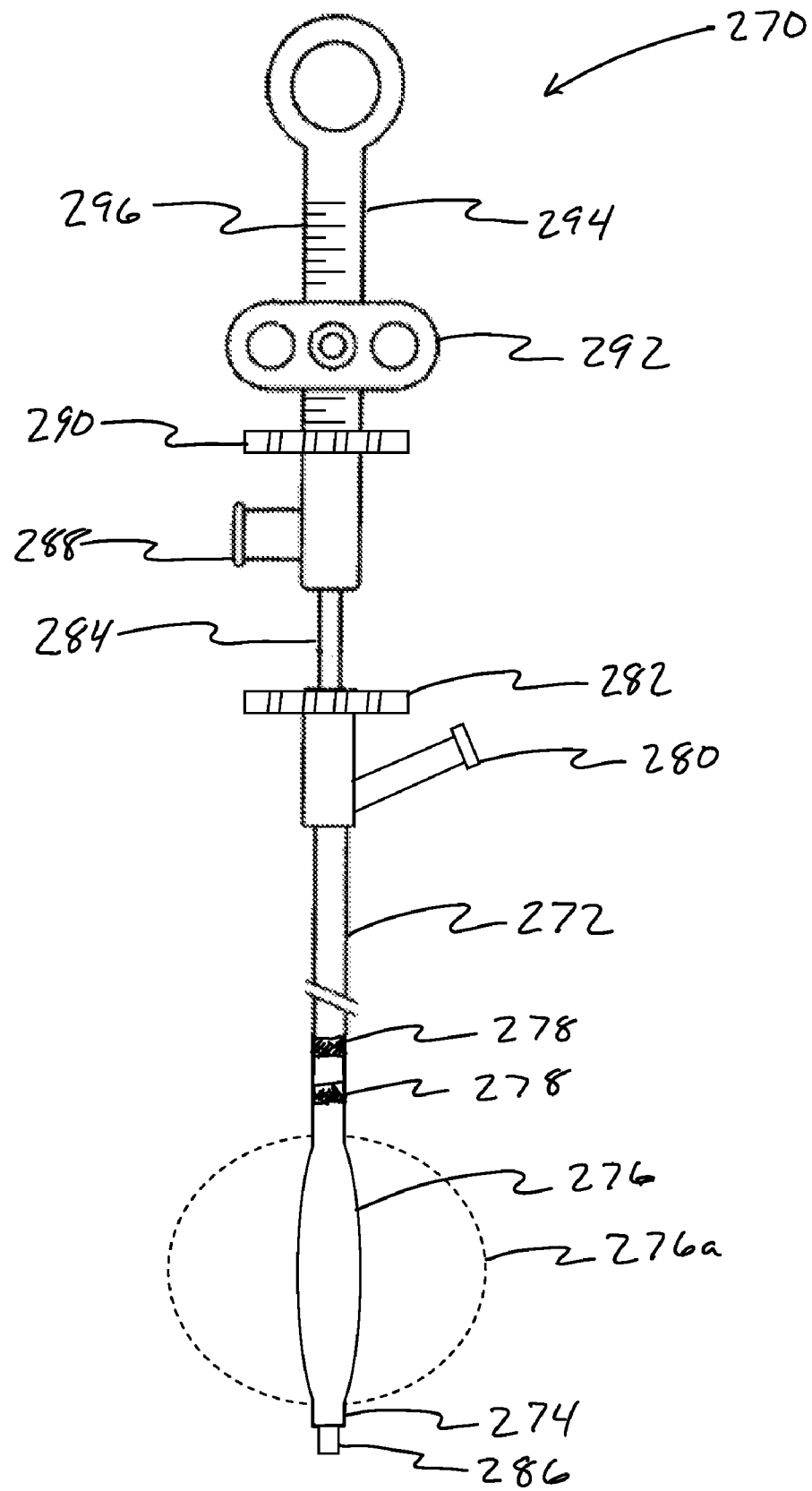
FIG. 26 is a side view showing a combined submucosal tunneling and dissection instrument according to an embodiment of a submucosal medical procedure system of the present invention.
Figure 27:
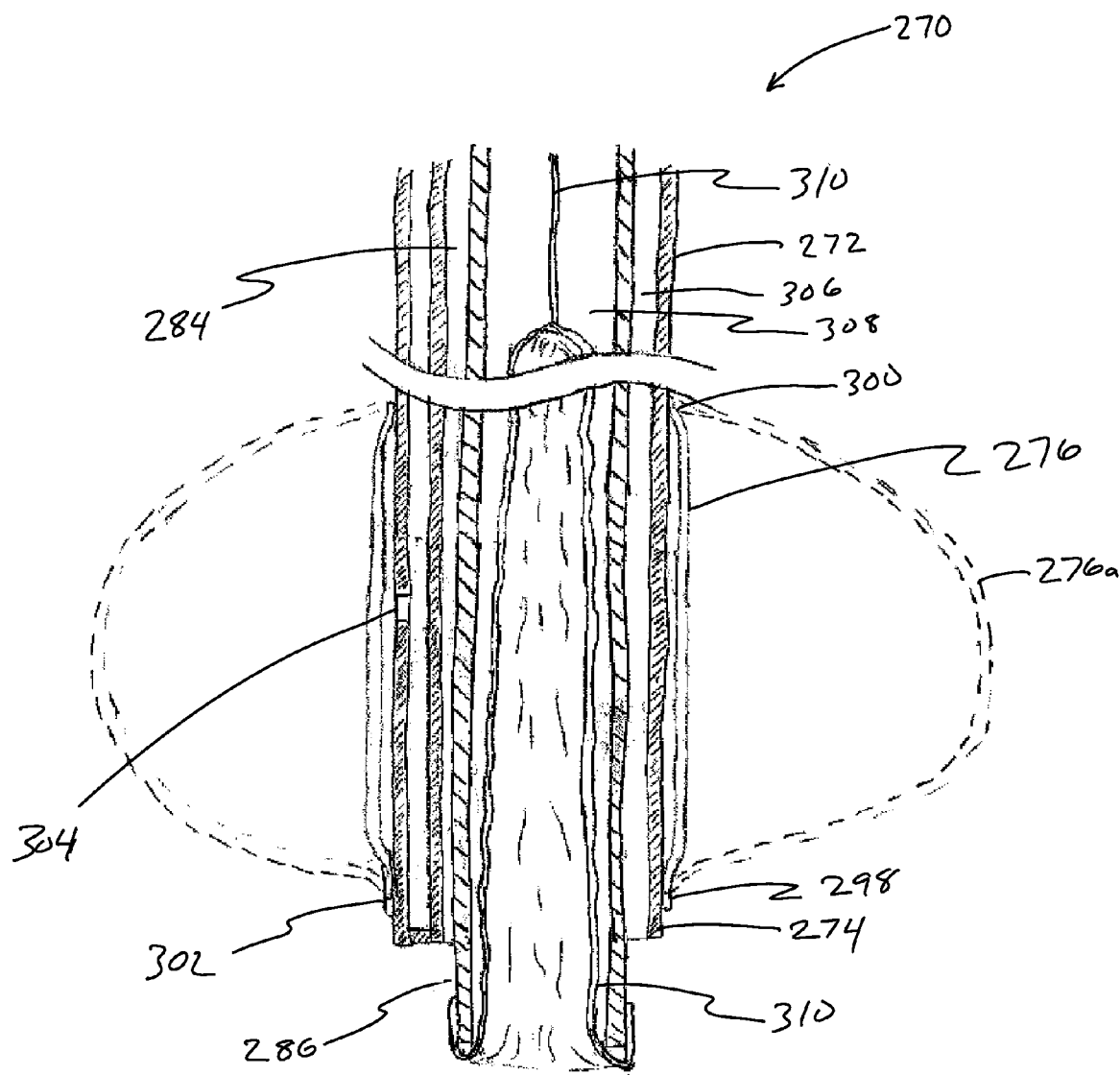
FIG. 27 is a broken cross-sectional view of a combined submucosal tunneling and dissection instrument according to an embodiment of a submucosal medical procedure system of the present invention.

Aforementioned descriptions of submucosal tunneling instruments and submucosal dissecting instruments have shown separate instruments to create a submucosal tunnel or large mucosal dissected area however the two types of instruments may be combined to form a submucosal tunneling dissecting instrument 270 as illustrated in FIG. 26. The submucosal tunneling dissecting instrument 270 includes a dissection catheter 272 having a distal end 274 and a dissection balloon 276 having an expanded dissection balloon 276a configuration. The dissection balloon 276 can be non-compliant of the type generally known in the art or dissection balloon 276 may be of the compliant or semi-compliant type. The dissection balloon 276 may be formed from biocompatible polymer types such as olefins, elastomers, thermoplastic elastomers, vinyls, polyamides, polyimides, polyesters, fluropolymers, copolymers and blends of any of the aforementioned. The dissection catheter 272 has insertion markers 278 positioned along its shaft. The proximal end of dissection catheter 272 includes both an inflation port 280 that is in fluid communication with dissection balloon 276, and a valve assembly 282. Tunneling catheter 284 is slidably disposed through valve assembly 282 extending within a lumen of dissection catheter 272. The tunneling catheter distal end 286 may extend beyond the dissection catheter distal end 274. Tunneling catheter 284 includes an inflation port 288 and valve assembly 290. A tether slide member 292 is slidably disposed on handle body 294 with distance markers 296. FIG. 27 illustrates a detailed cross section of the distal portion of the submucosal tunneling dissecting instrument 270. The distal end 298 and proximal end 300 of dissection balloon 276 are connected to the exterior of dissection catheter 272. Inflation lumen 302 connects inflation port 280 with the interior of dissection balloon 276 through inflation aperture 304. Tunneling catheter 284 is slidably disposed within the lumen 306 of dissection catheter 272. Positioned within the lumen 308 of tunneling catheter 284 there is an everted expandable tunneling balloon 310. The tunneling balloon 310 is preferably non-compliant of the type generally known in the art, however, tunneling balloon 310 may be of the compliant or semi-compliant type. The tunneling balloon 310 may be formed from biocompatible polymer types such as olefins, elastomers, thermoplastic elastomers, vinyls, polyamides, polyimides, polyesters, fluropolymers, copolymers and blends of any of the aforementioned. The distal end of tunneling balloon 310 is connected to a tether member 312 which has a proximal end that is connected to tether slide 292.

The operation of the submucosal tunneling dissecting instrument 270 to form a submucosal tunnel and large mucosal dissected area is similar to the operation of the separate instruments. In general, the distal end 286 of tunneling catheter 284 is positioned through a mucosal opening formed in a safety bleb. The tunneling catheter 284 is pressurized with fluid to linearly expand tunneling balloon 310. Once a submucosal tunnel has been formed tunneling balloon 310 may be deflated and dissection catheter 272 may be advanced through the mucosal opening into the submucosal tunnel. The markers 278 may be used to determine the depth in which the dissection catheter 272 has been advanced into the submucosal tunnel. Once the dissection catheter 272 has been properly positioned within the submucosal tunnel it may be operated. By applying pressurized fluid to inflation port 280, dissection balloon 276 is dilated to an expanded dissection balloon 276a configuration. During the expansion a large mucosal dissected area is created which is accessible for performing a subsequent submucosal medical procedure.

Figure 28:
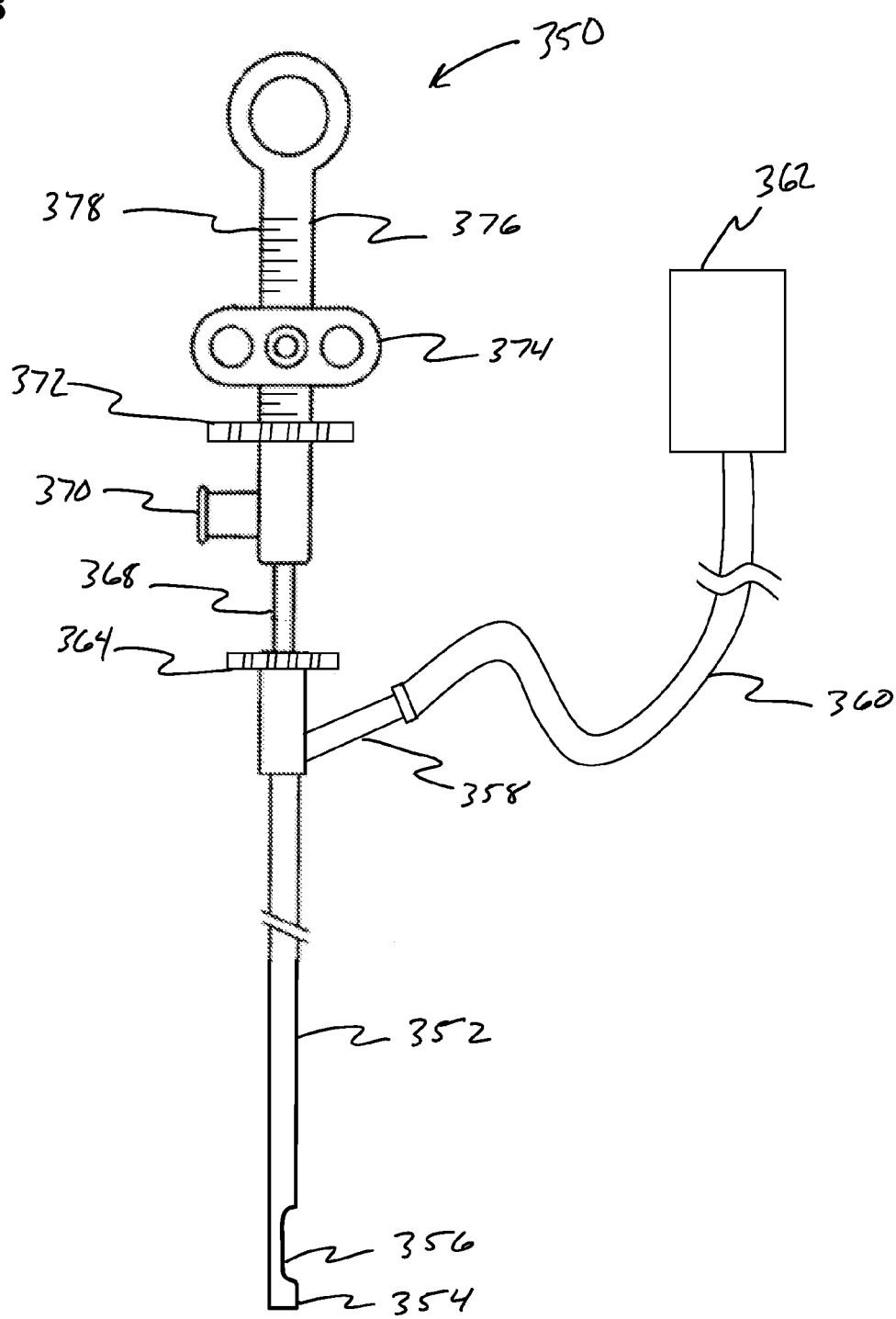
FIG. 28 is a side view showing a submucosal biopsy instrument according to an embodiment of a submucosal medical procedure system of the present invention.

A submucosal medical procedure according to an embodiment of the present invention which is partly or wholly enabled by the use of any of the foregoing instruments is the taking of a biopsy specimen from the muscular wall of the digestive tract. In another embodiment of the present invention, a submucosal biopsy instrument 350 is illustrated in FIG. 28. The submucosal biopsy instrument 350 includes a catheter 352 having a distal end 354. Located adjacent the distal end 354 of catheter 352 is a window member 356. Window member 356 is formed by removing a portion of the wall of catheter 352. Generally window member 356 has a length in the range of 2 mm and 100 mm and a preferred length of between 5 mm and 30 mm. The diameter of window member 356 is generally equal to or less than the diameter of catheter 352 in the range of 1 mm to 20 mm and preferably in the range of 2 mm to 10 mm. A suction port 358 is connected to catheter 352 and communicates with window member 356. A vacuum connector 360 facilitates the communication of a vacuum source 362 with suction port 358. Located at the proximal end of catheter 352 is valve assembly 364. Connector tubing 368 connects hydraulic fill port 370 with a lumen of catheter 352. The hydraulic fill port 370 is also connected to valve assembly 372. A pressure slide 374 is slidably positioned on handle body 376 along with distance markers 378.

FIGS. 29A and 29B illustrate a detailed cross section of the distal end of submucosal biopsy instrument 350. Catheter lumen 380 connects window member 356 with the vacuum source 362. Located within catheter lumen 380 and slidably positioned distal to window member 356 is tissue cutter 384. Tissue cutter 384 has a generally angled tubular shape with a diameter slightly less than the diameter of lumen 380. The tissue cutter is connected to bellows member 384. The proximal end 386 of bellows member 384 is in fluid tight engagement with tissue cutter 384. Bellows member 384 includes a distal end 388 and a lumen 390 where the distal end 388 is fixedly connected to catheter 352 by bellows securing member 392. The lumen 390 of bellows member 384 is in fluid connection with hydraulic lumen 394 of catheter 352. Hydraulic lumen 394 is in fluid communication with hydraulic fill port 370. Fluid may be inserted through hydraulic fill port 370 to fill bellows lumen 390 and hydraulic lumen 394. Once these lumens are filled with fluid hydraulic fill port 370 may be capped or sealed. Actuation of pressure slide 374 connected to a simple piston (not shown) generates hydraulic pressure which is transmitted to bellows member 384. This hydraulic pressure causes bellows member 384 to move from a first contracted configuration to a second extended configuration. Since the proximal end 386 of bellows member 384 is connected to tissue cutter 382, the hydraulic pressure generated by pressure slide 374 causes tissue cutter 382 to move in a proximal direction within lumen 380 from first position distal to window member 356 to a second position proximal to window member 356.

Figure 30:
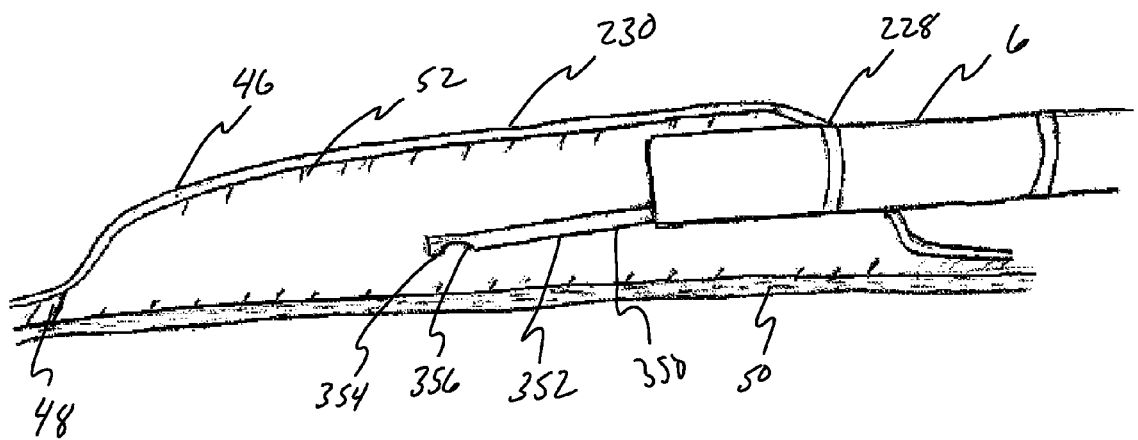
FIG. 30 is a partial cross-sectional view showing a submucosal biopsy instrument and endoscope positioned within a submucosal tunnel according to an embodiment of the submucosal medical procedure system of the present invention.
Figure 31A:
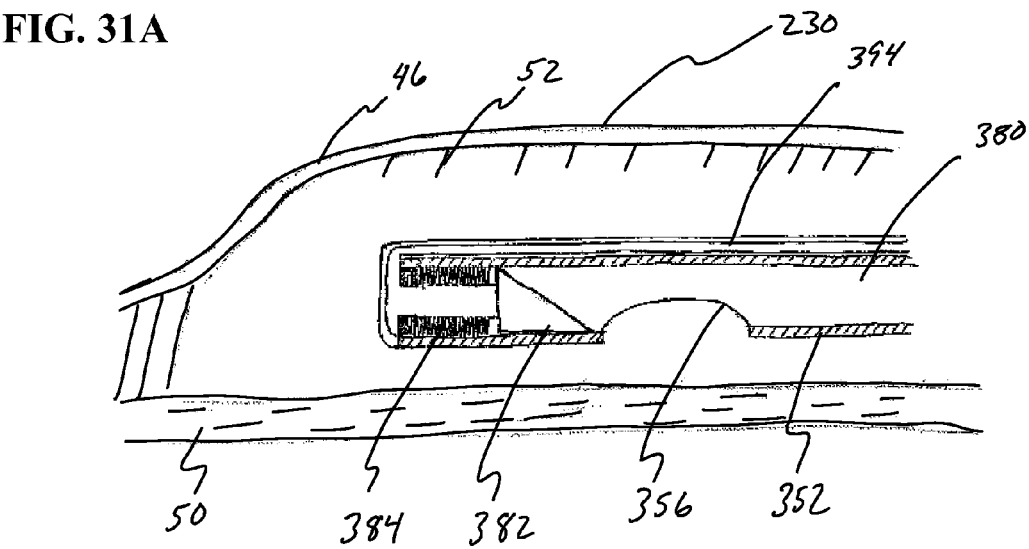
FIGS. 31A through 31E are cross-sectional views showing method of using a submucosal biopsy instrument according to an embodiment of a submucosal medical procedure system of the present invention.
Figure 31B:
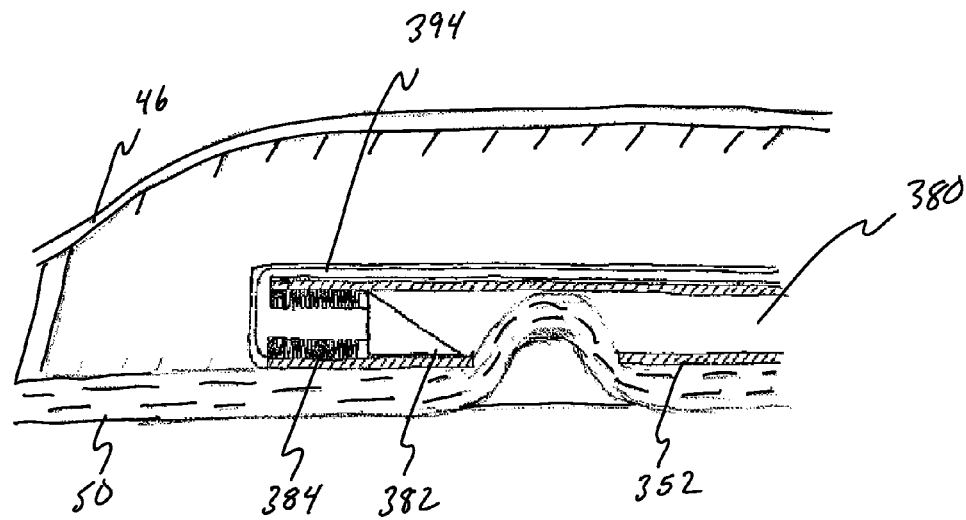
Figure 31C:
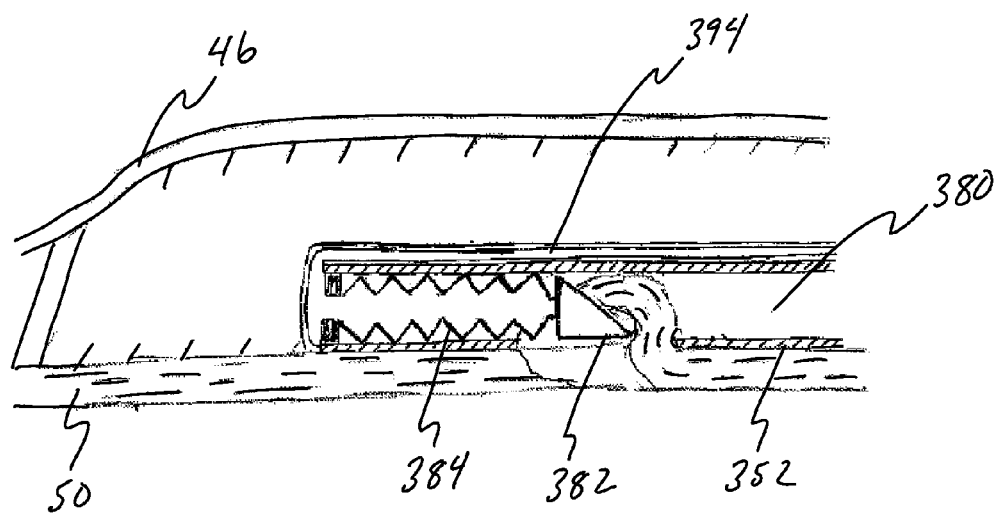
Figure 31D:
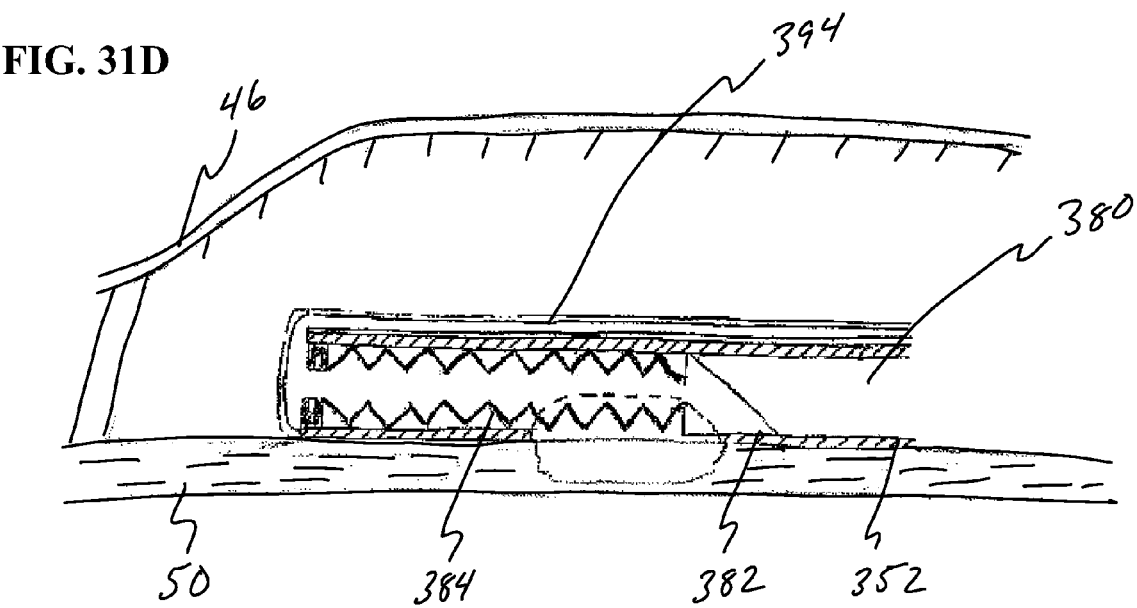
Figure 31E:
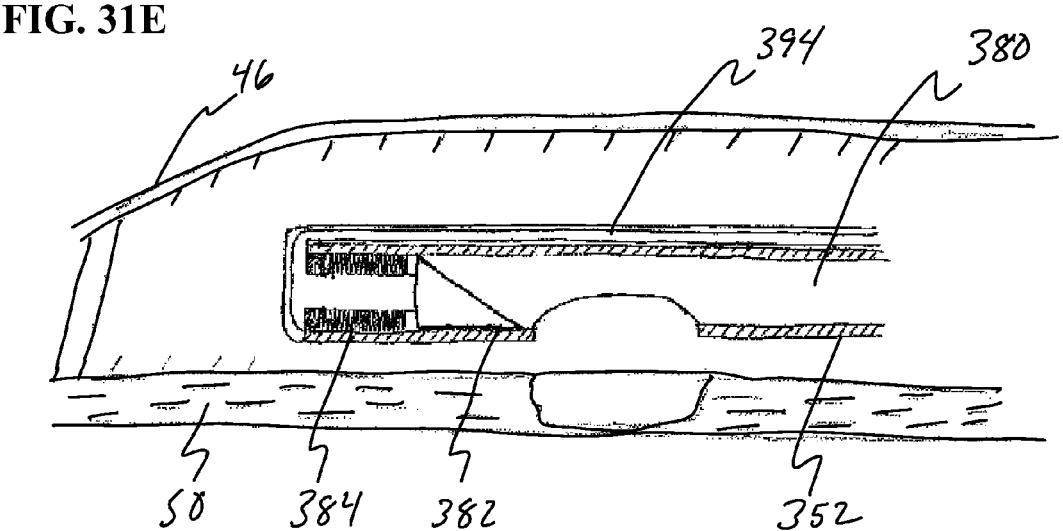
Figure 32A:
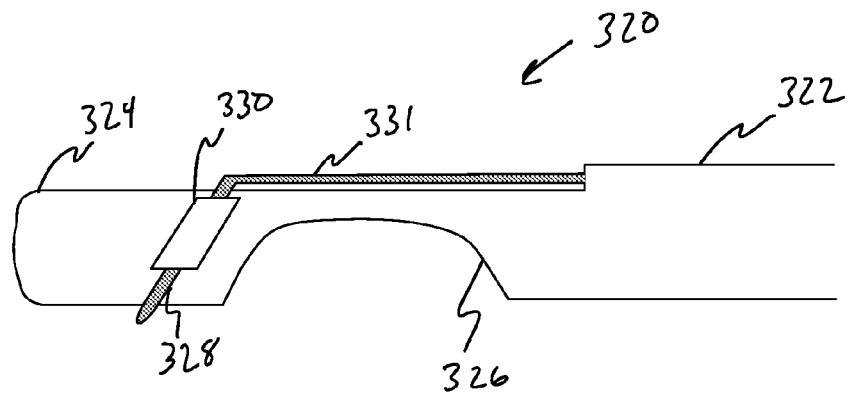
FIGS. 32A through 32D are side and cross-sectional views showing the actuation of a variation of a submucosal biopsy instrument according to an embodiment of a submucosal medical procedure system of the present invention.
Figure 32B:
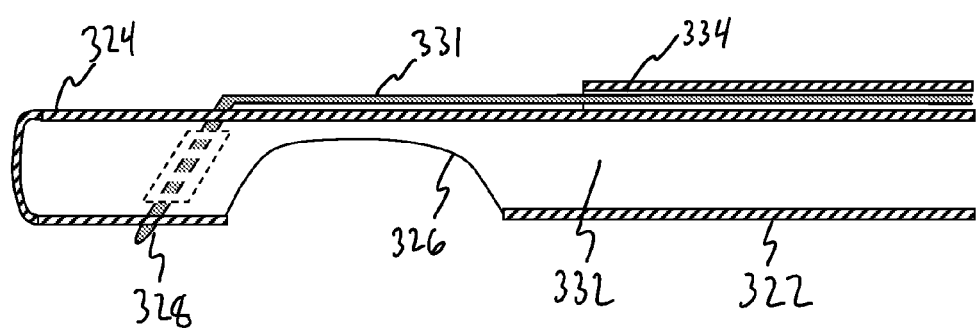
Figure 32C:
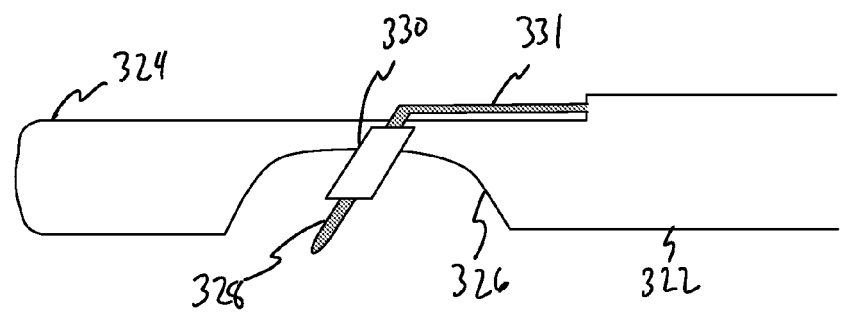
Figure 32D:
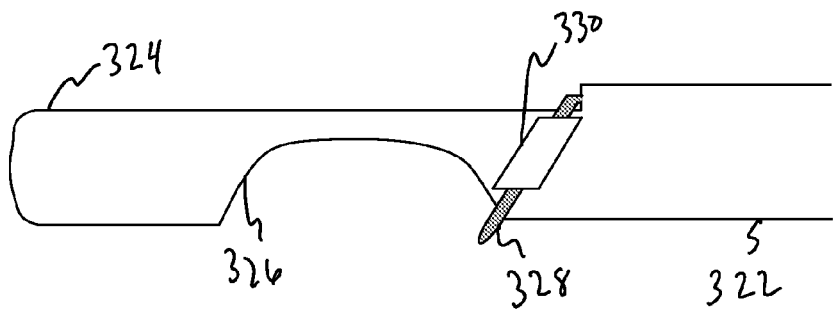
Figure 33A:
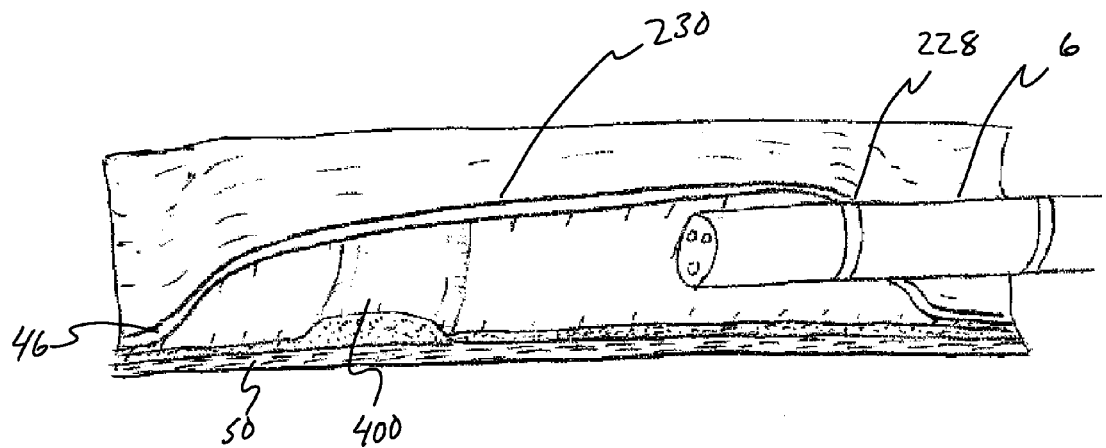
FIGS. 33A through 33D are partial cross-sectional perspective views showing a method of performing a submucosal myotomy according to an embodiment of a submucosal medical procedure system of the present invention.
Figure 33B:
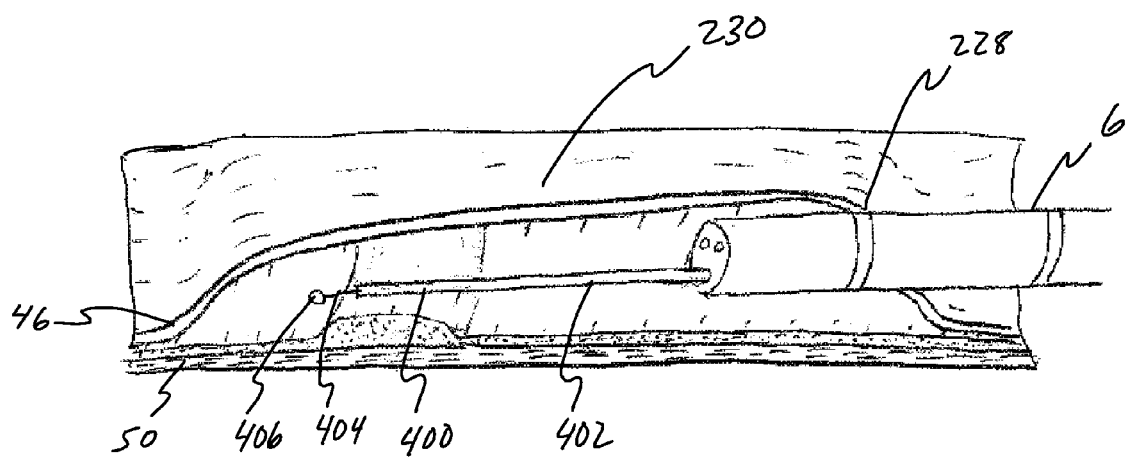
Figure 33C:
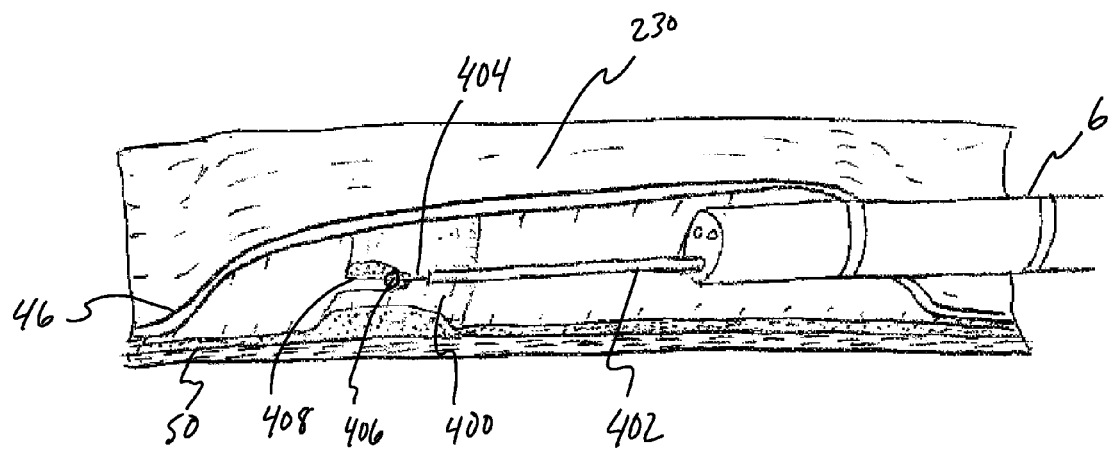
Figure 33D:
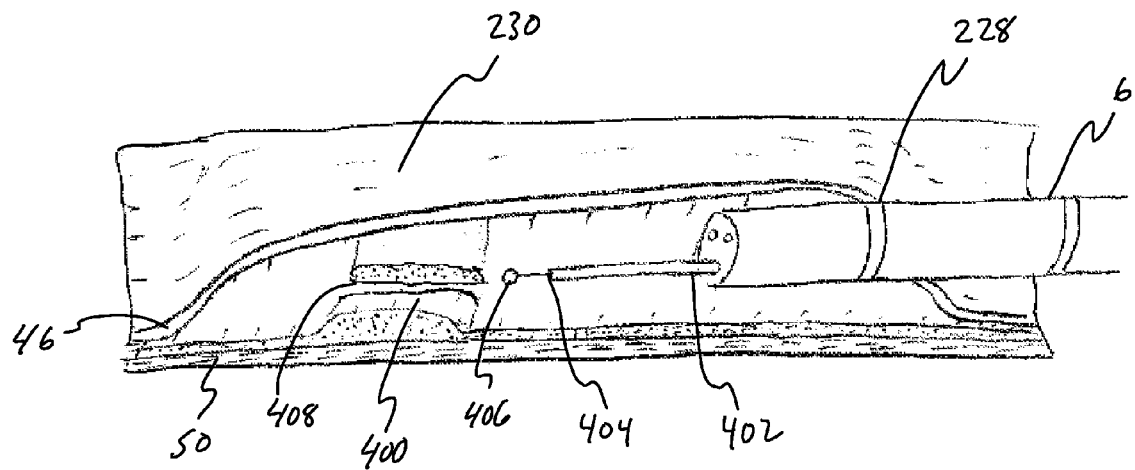

To perform a submucosal medical procedure according to an embodiment of the present invention an endoscope is advanced through a natural orifice and positioned within the digestive tract of a mammal. As illustrated in FIG. 30, the insertion section 6 of an endoscope 2 is positioned through an enlarged mucosal opening 228 into a submucosal tunnel 230 or alternatively, a large mucosal dissected area formed according to any of the previously described techniques. Submucosal biopsy instrument 350 is advanced through the natural orifice of the patient, preferably through a working channel of the endoscope, into the submucosal tunnel. FIGS. 31A through 31E illustrate the operation of submucosal biopsy instrument 350 to perform a submucosal medical procedure to obtain a tissue specimen. The distal end 354 of catheter 352 is positioned within submucosal tunnel 230 so that window member 356 is adjacent the muscular layer 50 of the digestive tract. Tissue cutter 382 and bellows member 384 are in their first positions distal to window member 356. Vacuum is applied to catheter lumen 380 and a portion of muscular layer 50 is suctioned within window member 356. Hydraulic pressure is then generated within bellows member 384 causing bellows member 384 and tissue cutter 382 to move to their second position proximal to window member 356. As tissue cutter 382 moves from its first to second positions it severs the tissue suctioned within window member 356. The biopsy specimen may be suction through the catheter lumen 380 to a collection jar adjacent the vacuum source. The negative hydraulic pressure is generated to return bellows member 384 and tissue cutter 382 from their second positions back to their first positions. The operation of submucosal biopsy instrument 350 may be repeated to obtain additional biopsy samples.

FIGS. 32A through 32D illustrate a submucosal biopsy instrument 320 in accordance with another embodiment of the present invention. Catheter 322 has a distal end 324 and a window member 326. Window member 326 is formed by removing a portion of the wall of catheter 322. A tissue cutter 328 is configured to encircle the distal end 324 of catheter 322. An insulator member 330 is disposed about at least a portion of tissue cutter 328. The insulator member 330 prevents damage to surrounding tissue when tissue cutter 328 is operated. Insulator member 330 is preferably formed of non-conductive polymers or ceramics. Tissue cutter 328 is connected to the distal end of an elongate shaft member 331. Catheter 322 includes a first lumen 332 and a second lumen 334. First lumen 332 connects the proximal end of catheter 322 to the window member 326. The elongate shaft member 331 is slidably disposed within the second lumen 334. The distal end of the second lumen 334 is positioned proximal to the proximal end of the window member 326. Movement of the proximal end of the elongate member 331 in a proximal direction relative to the proximal end of the tubular member causes the tissue cutter 328 to move from a first position distal to the window member 326 to a second position proximal to the window member 326. The tissue cutter 328 preferably takes the form of an electrosurgical cutter in which tissue suctioned into the window member 326 by applying a vacuum to lumen 332, may be severed, when high frequency energy is supplied to the tissue cutter 328 and the tissue cutter 328 is moved from the first position to the second position. The tissue cutter 328 may also take the form of a mechanical blade in which electrical energy need not be applied.

FIGS. 33A through 33D illustrate a method of performing a submucosal medical procedure according to an embodiment of the present invention for the treatment of Achalasia in a mammal. A submucosal tunnel 230 or large mucosal dissected area is formed beneath the mucosal layer 46 of the esophagus encompassing the lower esophageal sphincter. The distal end of the insertion section 6 of an endoscope is positioned through an enlarged mucosal opening 228 into the area beneath the mucosal layer 46. The endoscope is used to visualize the submucosal space and identify the circular muscle 400 of the lower esophageal sphincter. An endoscopic cutting instrument 402 is delivered through the mucosal opening 228, preferably through a working channel of the endoscope. While the cutting instrument 402 may take the form of an optical or mechanical cutter such as a laser, scalpel, scissors, or water jet but preferably of the electrosurgical type known in the art. The electrosurgical type cutting instrument 402 includes an electrode tip 404 and a nonconductive distal end 406. The electrode tip 404 of cutting instrument 402 is positioned adjacent to the distal portion of circular muscle 400. As cutting instrument 402 is moved proximally, electrode tip 404 is activated forming a generally perpendicular incision 408 in circular muscle 400. Nonconductive distal end 406 is adjacent the muscular layer 50 and prevents the cutting instrument 402 from cutting or perforating the wall of the esophagus. The nonconductive distal end 406 may be formed of polymers, ceramics or composites that do not conduct electrical energy. The shape of the nonconductive distal end 406 is preferably spherical, but may also take other geometrical forms such as triangles, pyramids parallelepipeds, trapezoids or more complex shapes. Once the incision 408 has completely traversed circular muscle 400 the myotomy is complete. The endoscope and cutting instrument 402 may then be removed from the submucosal space. After closing mucosal opening 228 by using any suitable means such as suturing, stapling or clips, the endoscope may be removed from the patient.

Figure 34A:
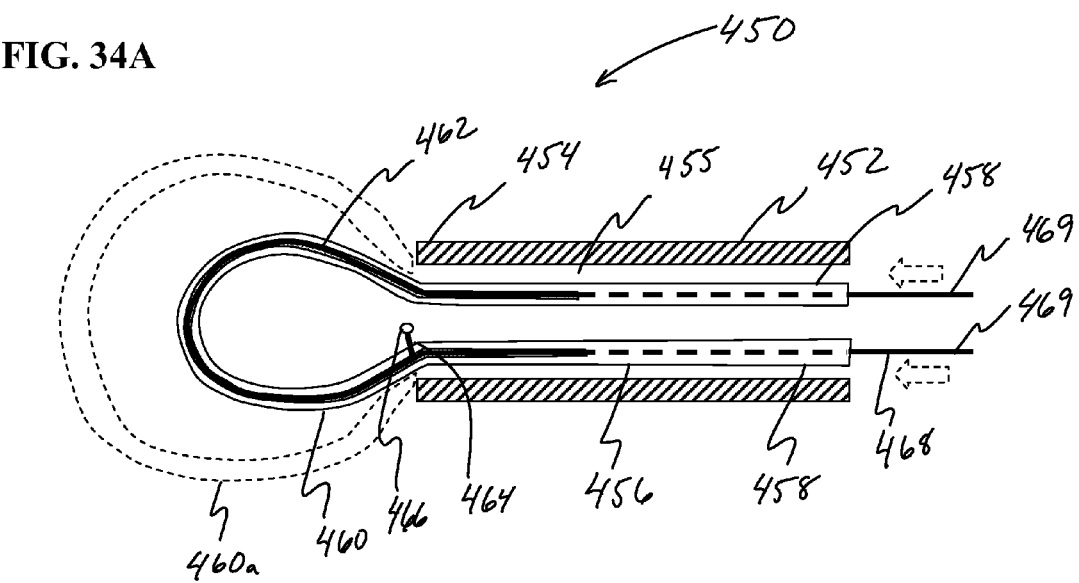
FIGS. 34A and 34B are cross-sectional views showing a mucosal resection device according to an embodiment of a submucosal medical procedure system of the present invention.
Figure 34B:
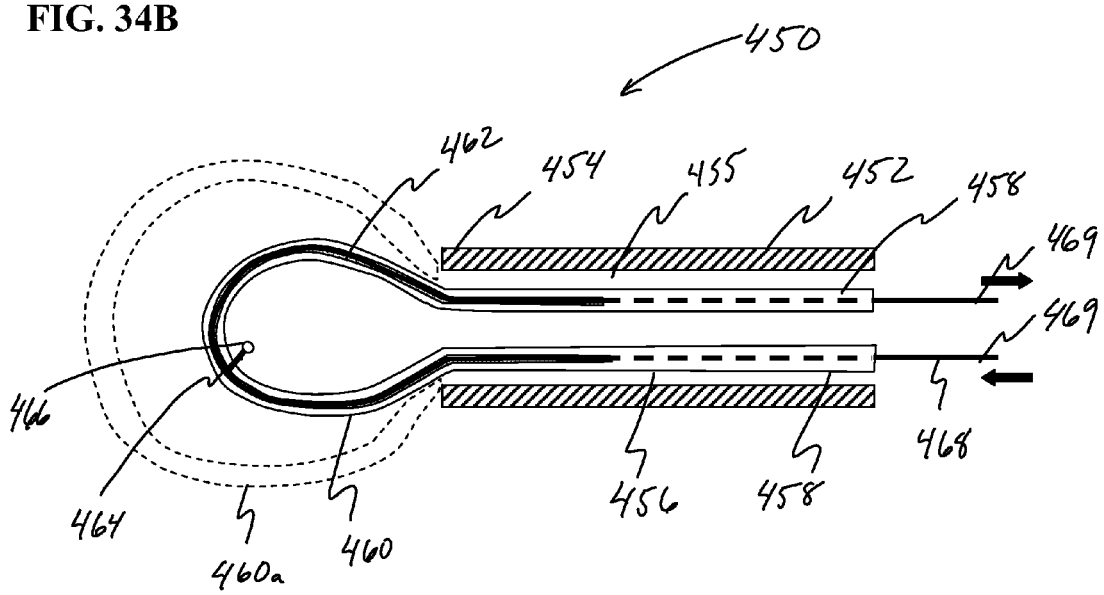

FIGS. 34A and 34B illustrate a mucosal resection device for performing a submucosal medical procedure to resect a portion of the mucosal layer in the digestive tract of a mammal according to another embodiment of the present invention. The mucosal resection device 450 includes a catheter 452 having a distal end 454, a proximal end and a lumen 455. Slidably disposed within the lumen 455 is a track member 456. Track member 456 is preferably formed of an elongate tube having a through lumen including two proximal ends 458 and a distal loop 460. Distal loop 460 has a first delivery configuration in which the diameter of the loop is small and a second deployed configuration expanded distal loop 460a in which the diameter of the loop is large. The diameter of distal loop 460 is adjustable by moving one or both of proximal ends 458 in a distal direction relative to catheter 452. Distal loop 460 is positioned adjacent the distal end 454 of catheter 452 and includes an elongate slot 462 through the wall of track member 456. Cutting tip 464 is positioned adjacent distal loop 460 extending from the lumen of track member 456 through slot 462. Cutting tip 464 includes an insulator tip 466 at its distal end and is connected to wire member 468 which is slidably disposed within the lumen of track member 456 and has ends 469 that extend through proximal ends 458. By moving one of the ends 469 of wire member 468 in a relatively proximal direction relative to track member 456, the cutting tip 464 slides along distal loop 460 of track member 456 following the path of slot 462. Cutting tip 464 may be moved in the opposite direction along distal loop 460 by moving the other end 469 in a relatively proximal direction. Preferably, cutting tip 464 is of the electrosurgical type; however, it may also be configured to cut tissue by mechanical or optical means such as a blade, water jet or laser.

Figure 35A:
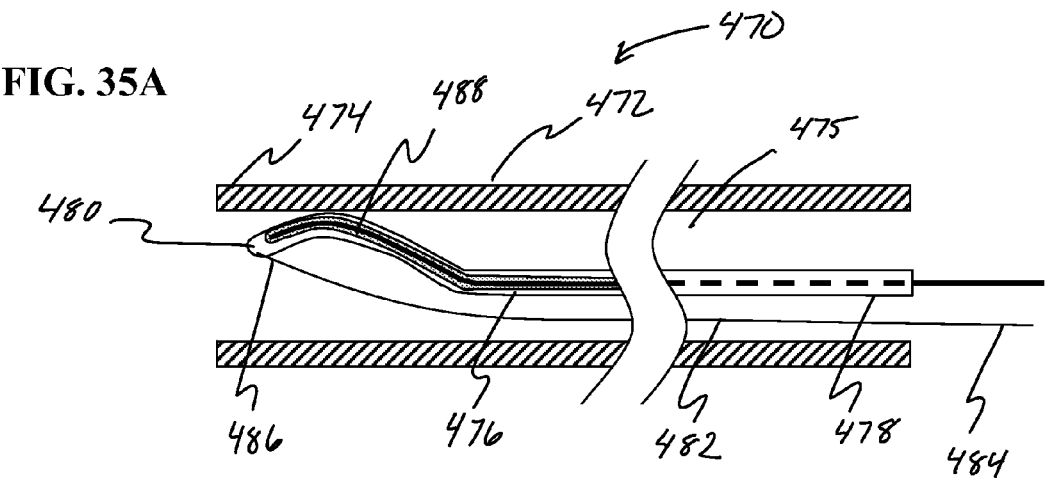
FIGS. 35A through 35C are cross-sectional views showing a variation of a mucosal resection device according to an embodiment of a submucosal medical procedure system of the present invention.
Figure 35B:
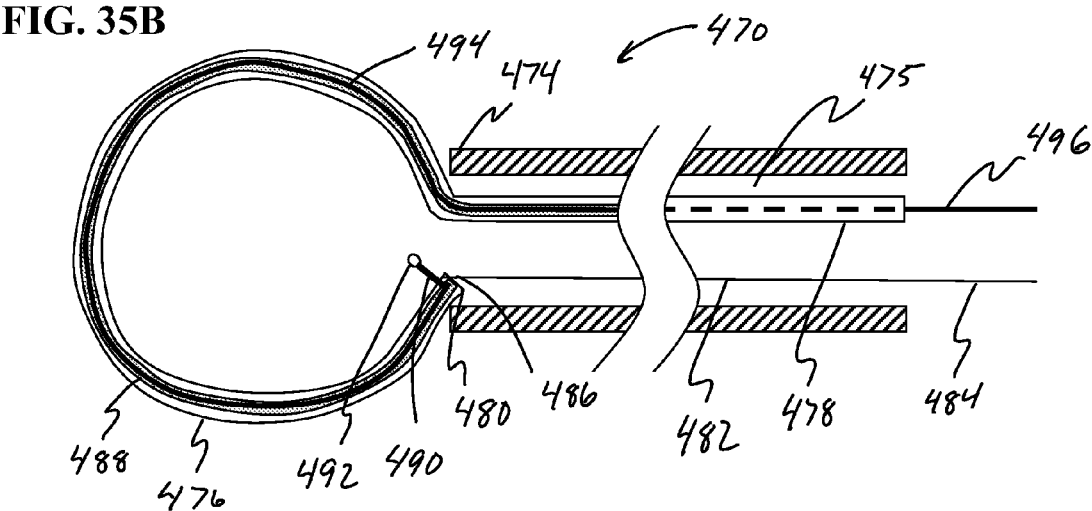
Figure 35C:
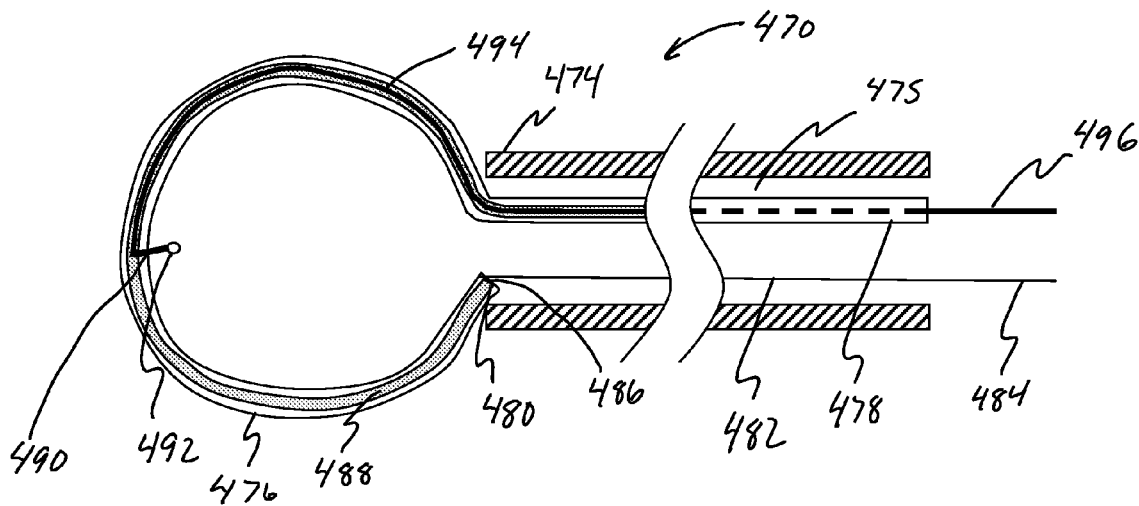

FIGS. 35A through 35C illustrate another mucosal resection device for performing a submucosal medical procedure to resect a portion of the mucosal layer in the digestive tract of a mammal according to another embodiment of the present invention. The mucosal resection device 470 includes a catheter 472 having a distal section 474, a proximal section and a lumen 475. Slidably disposed within the lumen 475 of catheter 472 is a track member 476. Track member 476 is preferably formed of an elongate tube having a proximal section 478, and a distal section 480 and a lumen. Also slidable within the lumen 475 of catheter 472 is a flexible member 482 having a proximal end 484 and a distal end 486. The distal end 486 of flexible member 482 is connected to the distal section 480 of track member 476. Track member 476 has a first configuration in which the distal section 480 is in a generally linear configuration for delivery through the lumen 475 of catheter 472 and a second configuration in which distal section 480 is in a generally shaped configuration for deployment. The track member 476 is operable between the first and second configurations by extending the distal section 480 from the lumen 475. As the distal section 480 of track member 476 extends from the lumen 475 it begins to take its second shaped configuration. The distal section 480 is preferably formed into a loop having a desired diameter by advancing track member 476 and retracting flexible member. The distal section 480 of track member 476 also includes an elongate slot 488 through the wall of track member 476 to the lumen. Cutting tip 490 is positioned adjacent distal end 480 extending from the lumen of track member 476 through slot 488. Cutting tip 490 includes an insulator tip 492 at its distal end and is connected to wire member 494 which is slidably disposed within the lumen of track 476. Wire member 494 has a proximal end that extends beyond the proximal end 478 of track member 476. By moving the proximal end 496 of wire member 494 in a proximal direction relative to track member 476, the cutting tip 490 slides along the distal section 480 of track member 476 following the path of slot 488. Cutting tip 490 may be moved in the opposite direction along distal section 480 by moving the proximal end 496 in a distal direction relative to track 476. Preferably, cutting tip 464 is of the electrosurgical type however, it may also be configured to cut tissue by mechanical or optical means such as a blade, water jet or laser.

Figure 36A:
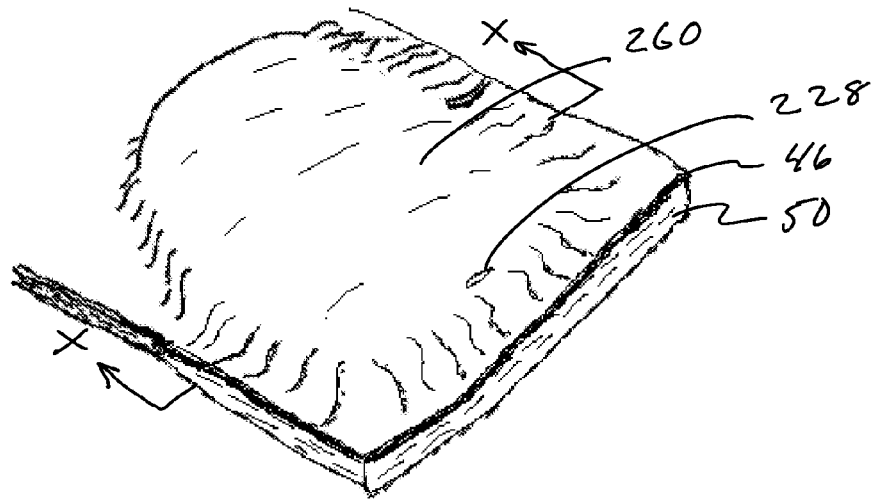
FIGS. 36A through 36I are cross-sectional views showing a method of resecting a desired region of mucosal tissue using a mucosal resection device according to an embodiment of a submucosal medical procedure system of the present invention.
Figure 36B:
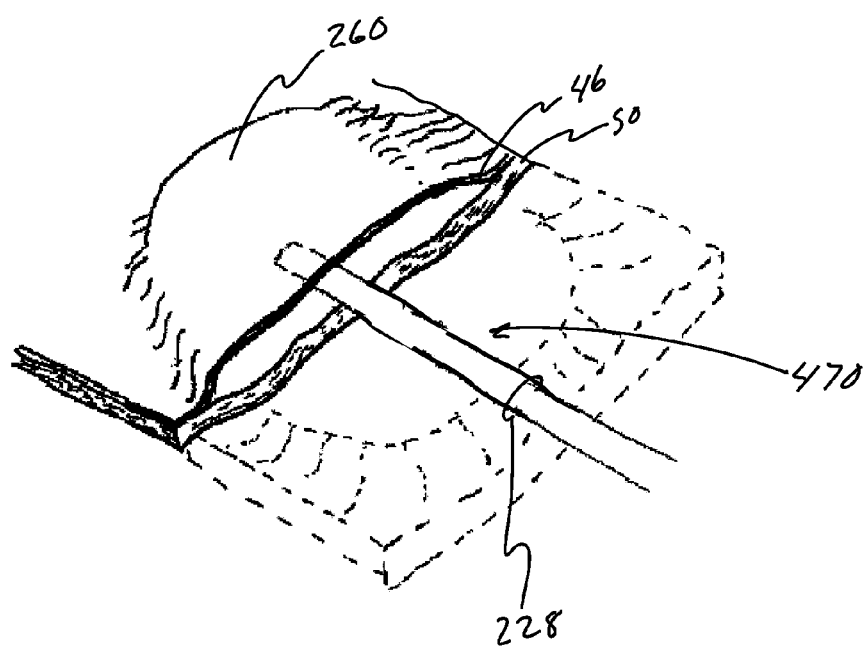
Figure 36C:
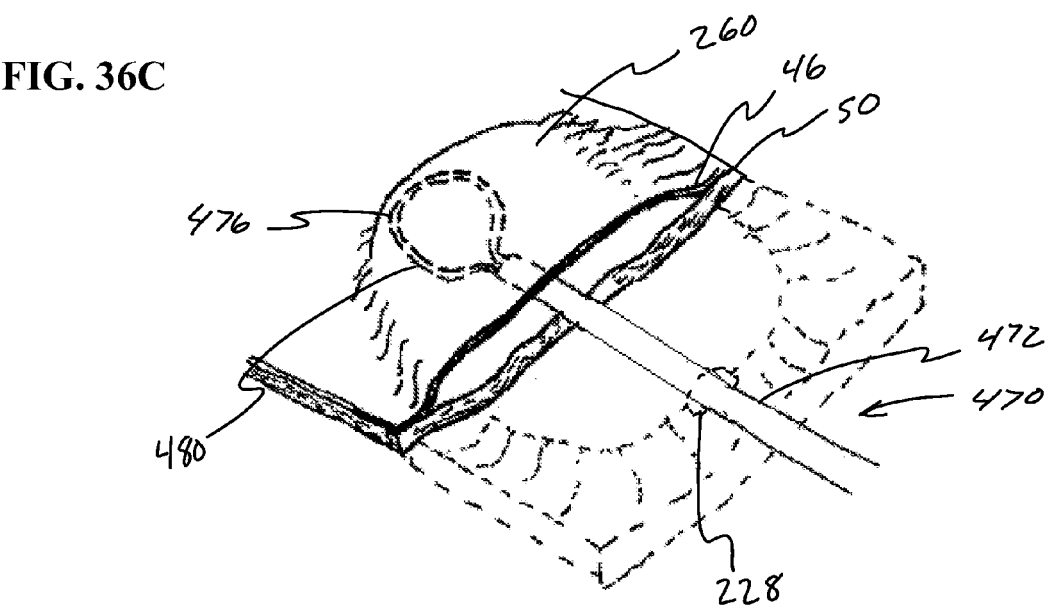
Figure 36D:
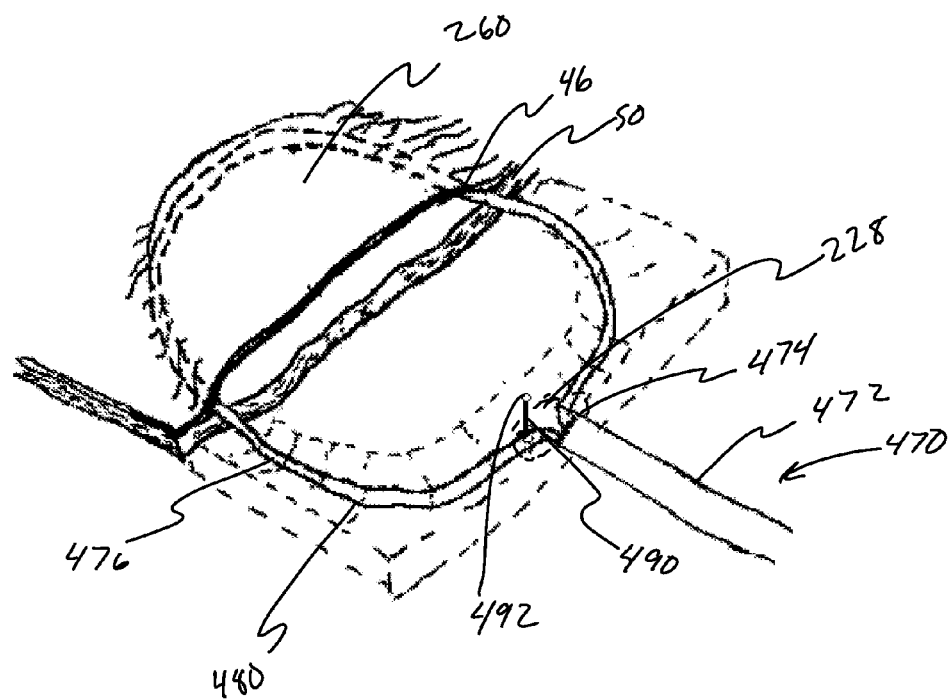
Figure 36E:
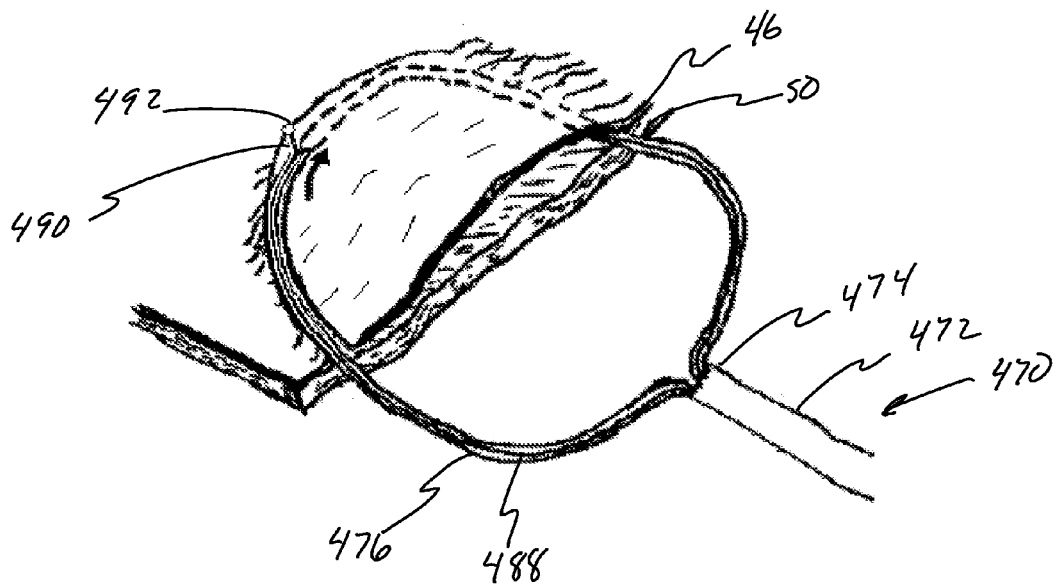
Figure 36F:
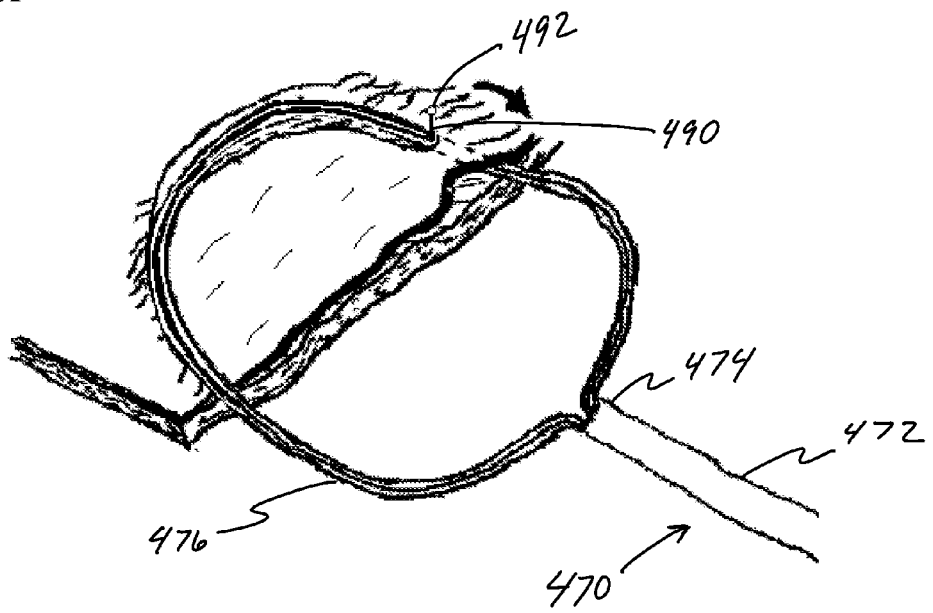
Figure 36G:
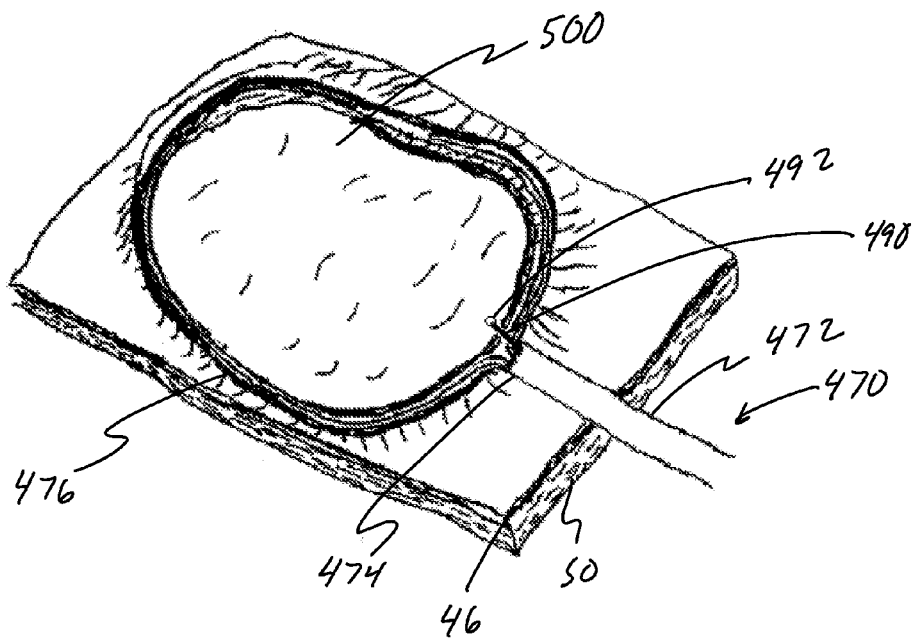
Figure 36H:
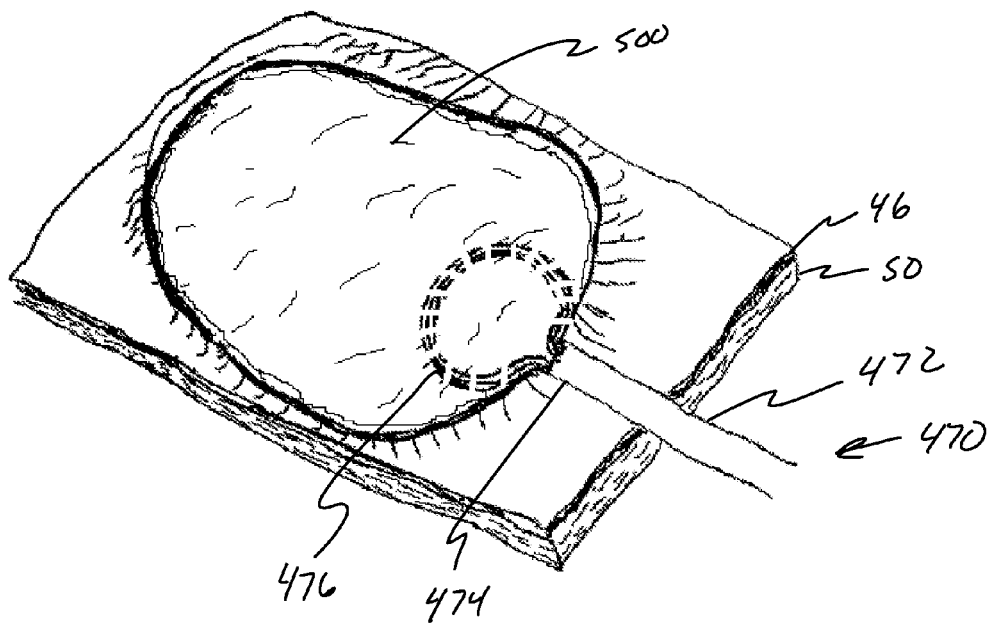
Figure 36I:
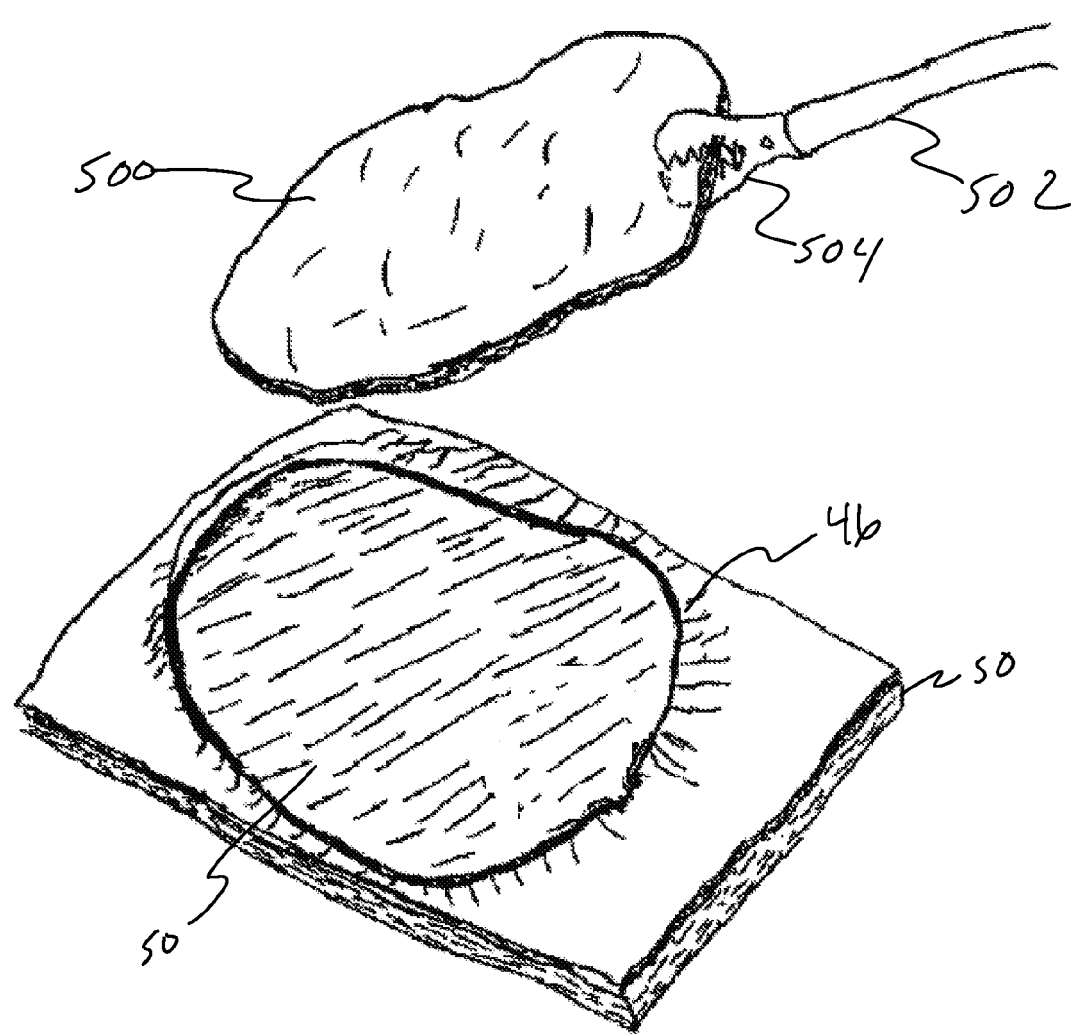

FIGS. 36A through 36I illustrate a method of operating a mucosal resection device to perform a submucosal medical procedure to remove a desired region of the mucosal layer in a mammal according to an embodiment of the present invention. A large mucosal dissected area 260 is created in the digestive tract preferably according to any of the aforementioned procedures. A mucosal resection device 470 is positioned through an enlarged mucosal opening 228 through the mucosal layer 46 of large mucosal dissected area 260. As depicted in FIG. 36C, track member 476 is advanced from the lumen of catheter 472 beneath mucosal layer 46 to form a loop in the distal section 480 of track member 476. The catheter distal end 474 is positioned adjacent the mucosal opening and the loop formed by distal section 480 is enlarged to the diameter of the large mucosal dissected area by advancing the track member 476 from catheter 472 as shown in FIG. 36D. When the distal section 480 is formed in the expanded loop configuration, cutting tip 490 and insulator tip 492 are extended through the mucosal layer 46 preferably through mucosal opening 228. With the cutting tip 490 extending through the mucosal layer 46, the cutting tip 490 may be activated and wire member 496 moved in a proximal direction relative to track member 476 to cause the cutting tip 490 to move along the distal section 480 of track member 476. As the cutting tip 490 moves along the distal section 480 following the loop path of slot 488, the cutting tip 490 cuts the mucosal layer 46 as shown in FIGS. 36E and 36F. Once the cutting tip 490 reaches the distal end 474 of catheter 472, the cutting tip 490 may be deactivated leaving a mucosal layer swath 500 that is severed from the surrounding mucosal layer 46 as illustrated in FIG. 36G. Track member 476 may be withdrawn into catheter 472 and mucosal resection device 470 removed from the patient. A tissue removal device 502 preferably having jaws 504 may be inserted into the digestive tract and used to retrieve the en bloc mucosal layer swath 500, as depicted in FIG. 36I.

Novel instruments, systems and methods have been disclosed to perform submucosal medical procedures in the digestive tract of a mammal. Although preferred embodiments of the invention have been described, it should be understood that various modifications including the substitution of elements or components which perform substantially the same function in the same way to achieve substantially the same result may be made by those skilled in the art without departing from the scope of the claims which follow.

What is claimed is:

1. A submucosal dissection system for use in a patient having a mucosal layer of tissue and an underlying connected submucosal layer of tissue, said system comprising:
a safe access needle injection instrument having a needle portion having a lumen wherein said needle portion is adapted to pierce a desired region of the mucosal layer of tissue and enter the underlying connected submucosal layer such that delivery of a fluid through said lumen of said needle portion enters the submucosal layer to thereby elevate the desired region of the mucosal layer;
a submucosal tunneling instrument for tunneling between the connected mucosal and submucosal layers, said tunneling instrument being a distinct and separate instrument from said needle injection instrument such that said tunneling instrument can be inserted into the patient separately from said needle injection instrument, said submucosal tunneling instrument comprising an elongate tubular member having proximal and distal ends and a lumen extending therethrough, said distal end having a first outer diameter, and a first expandable member having proximal and distal ends wherein said proximal end of said first expandable member is attached to said distal end of said tubular member and said distal end of said first expandable member is everted and positioned within said lumen of said tubular member, said first expandable member closing said lumen to prevent fluid communication between the said lumen of said elongate tubular member of said tunneling instrument and the tissue of the patient, wherein upon expansion of said expandable member, said first expandable member expands in a longitudinal direction and a transverse diametric direction, such that said expanded outer diameter of said first expandable member is greater than said first outer diameter of said distal end, and a length of said expanded first expandable member is several times greater than said expanded outer diameter, said first expandable member adapted to be expanded with sufficient force to form an elongate tunnel between two layers of connected tissue; and
a submucosal dissection instrument comprising an elongate tubular member having proximal and distal sections and second expandable member disposed at said distal section of said tubular member, said distal section having a distal end, said second expandable member expandable greater in a diametric direction than in a longitudinal direction such that when said second expandable member is inserted into the elongate tunnel formed in the tissue by said tunneling instrument and is operated to expand said second expandable member, said second expandable member expands diametrically and not ahead of said distal end of said distal section and is adapted to dissect the layers of tissue above and below the tunnel.

2. A submucosal dissection system according to claim 1, wherein said submucosal tunneling instrument comprises an elongate tether member having proximal and distal ends and being slidably disposed within the lumen of said elongate tubular member wherein the distal end of said tether member engages the distal end of said first expandable member.

3. A submucosal dissection system according to claim 1, wherein said first expandable member is an evertable balloon, said evertable balloon enclosing the distal end of said tubular member of said tunneling instrument such that fluid communication between said tubular member of said tunneling instrument and the tissue of the patient is prevented.

4. A submucosal dissection system for use in a patient having a mucosal layer of tissue and an underlying connected submucosal layer of tissue, said system comprising:
a safe access needle injection instrument having a needle portion having a lumen wherein said needle portion is adapted to pierce a desired region of the mucosal layer of the tissue and enter the submucosal layer such that delivery of a fluid through said lumen of said needle portion enters the submucosal layer to thereby elevate the desired region of the mucosal layer;
a submucosal tunneling instrument comprising an elongate tubular member having proximal and distal ends and a lumen extending therethrough, and a first expandable member having proximal and distal ends wherein said proximal end of said first expandable member is attached to said distal end of said tubular member and said distal end of said first expandable member is everted and positioned within said lumen of said tubular member, and said first expandable member closes said lumen to prevent fluid communication between the said lumen of said elongate tubular member of said tunneling instrument and the tissue of the patient, and whereupon expansion of said tubular member, said first expandable member expands both axially in length and radially in diameter, said expanded length being multiple times greater in dimension than said expanded diameter; and
a submucosal dissection instrument comprising an elongate tubular member having proximal and distal sections and a second expandable member disposed at said distal section of said tubular member.

5. A submucosal dissection system according to claim 4, wherein said tunneling instrument and said dissection instrument are each distinct instruments.

6. A dissection method to dissection a mucosal layer of tissue from a submucosal layer of tissue, the mucosal and submucosal layers connected with connective tissue, said method comprising the steps of:
elevating a mucosal layer by injecting a fluid into a submucosal layer using a needle assembly to form a bleb;
locating a submucosal tunneling instrument into the bleb, said tunneling instrument having a first expandable member that is expandable greater in a longitudinal direction than in a diametric direction;
without first cutting the connective tissue to form a pilot hole in the bleb for receiving the first expandable member, operating said submucosal tunneling instrument to expand the first expandable member in the longitudinal direction to break apart connective tissue and create an elongate tunnel in the submucosal layer, said tunnel having a first length and a first diameter;

locating a submucosal dissecting instrument within the elongate tunnel formed by said tunneling instrument, said submucosal dissecting instrument having a second expandable member that has an outer diameter when in an non-expanded state that is smaller than said first diameter, and which is expandable to a dimension in the diametric direction that is larger than said first expandable member is capable of being expanded in the diametric direction; and operating said submucosal dissecting instrument within the elongate tunnel to thereby expand said second expandable member in said diametric direction to dissect an area having a diameter larger than the diameter of said elongate tunnel.

7. A submucosal layer dissection method according to claim 6, wherein said submucosal tunneling instrument comprises an elongate tubular member having proximal and distal ends and a lumen extending therethrough and said first expandable member having proximal and distal ends wherein the proximal end of said expandable member is attached to the distal end of said tubular member and the distal end of said first expandable member is everted and positioned within the lumen of said tubular member.

8. A submucosal layer dissection method according to claim 7, wherein said first expandable member of said submucosal tunneling instrument comprises a balloon.

9. A submucosal layer dissection method according to claim 7, wherein once operation of said tunneling instrument is initiated, said submucosal tunneling instrument creates said tunnel without moving said elongate tubular member of said tunneling instrument relative to said bleb.

10. A submucosal layer dissection method according to claim 9, wherein said bleb has a diameter, said first length of said tunnel corresponds in dimension to said diameter of said bleb, and once located within said tunnel, operation of said submucosal dissection system dissects the tissue along an entirety of said first length of said tunnel.

11. A submucosal layer dissection method according to claim 6, wherein said submucosal tunneling instrument is withdrawn from the elongate tunnel prior to positioning said submucosal dissecting instrument within the elongate tunnel.

* * * * *